United States Patent [19]

Hayashi et al.

[11] 4,393,225
[45] Jul. 12, 1983

[54] AI-77 COMPOUNDS AND PHARMACEUTICALLY ACCEPTABLE SALTS THEREOF

[75] Inventors: Hiroshi Hayashi; Yukiji Shimojima; Takashi Shirai; Torao Ishida, all of Fuji; Mitsuru Shibukawa, Yokohama, all of Japan

[73] Assignee: Asahi Kasei Kogyo Kabushiki Kaisha, Osaka, Japan

[21] Appl. No.: 167,581

[22] Filed: Jul. 11, 1980

[30] Foreign Application Priority Data

Jul. 11, 1979 [JP] Japan .................................. 54-86892
May 12, 1980 [JP] Japan .................................. 55-61685

[51] Int. Cl.³ .......................................... C07D 311/76
[52] U.S. Cl. .................................... 549/289; 424/279;
424/317; 562/471; 549/60; 549/70; 548/253;
548/525; 548/530; 546/168
[58] Field of Search ...................... 260/343.45, 343.21;
549/289

[56] References Cited
U.S. PATENT DOCUMENTS 4,183,954  1/1980  Bertelli .............................. 562/433

Primary Examiner—Jane T. Fan
Attorney, Agent, or Firm—Sughrue, Mion, Zinn, Macpeak and Seas

[57] ABSTRACT

AI-77 compounds, pharmaceutically acceptable salts thereof, and a process for the preparation thereof are described, said compounds having the formulae

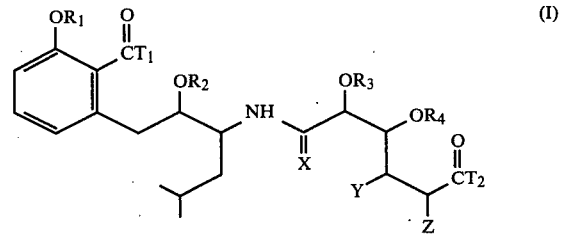

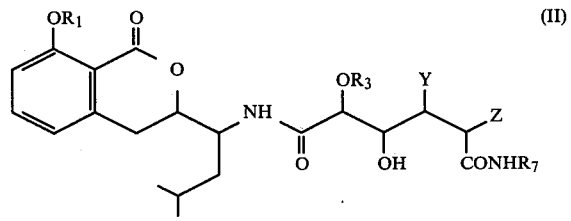

wherein: X is $NR_6$ or O; Y is $NHR_5$ or combine with Z to provide a link for bonding C and C; Z is H or combines with Y to provide a link for bonding C and C; $R_1$, $R_3$ and $R_5$ are each H, R', —$CH_2R$, or —COR; $R_6$ is H or R; $R_7$ is H, R or $CH_2R$; R is a hydrocarbon group consisting of a saturated or unsaturated straight or branched aliphatic group of $C_1$ to $C_{17}$, an aromatic group of $C_6$ to $C_{10}$, a cage type group of $C_7$ to $C_{10}$, a monocyclic aliphatic group of $C_3$ to $C_8$, an aromatic-aliphatic group of $C_7$ to $C_{15}$, a heterocyclic hydrocarbon of $C_1$ to $C_9$, wherein the above hydrocarbons can be substituted with one or more groups selected from halogen, oxo, carboxyl, hydroxyl, a saturated or unsaturated straight or branched aliphatic group of $C_1$ to $C_5$, an aromatic group of $C_6$ to $C_{10}$, a monocyclic aliphatic group of $C_3$ to $C_8$, an aromatic-aliphatic group of $C_7$ to $C_{11}$, alkoxy of $C_1$ to $C_5$, thioalkoxyl of $C_1$ to $C_5$, carboalkoxyl of $C_1$ to $C_6$, acyl of $C_1$ to $C_5$, acyloxy of $C_2$ to $C_6$ and a heterocyclic group of $C_1$ to $C_9$; R' is the same as R exclusive of those groups wherein unsaturated carbon or tertiary carbon is directly bonded to O or N; $R_2$ is H, or combines with $T_1$ to provide a link for bonding C and O in a lactone ring; $T_1$ is OH or combines with $R_2$ to provide a link for bonding C and O in a lactone ring; $R_4$ is H or combines with $T_2$ to provide a link for bonding C and O in a lactone ring; and $T_2$ is OH or combines with $R_4$ to provide a link for bonding C and O in a lactone ring; and pharmaceutically acceptable salts thereof.

5 Claims, No Drawings

AI-77 COMPOUNDS AND PHARMACEUTICALLY ACCEPTABLE SALTS THEREOF

SUMMARY OF THE INVENTION

According to the invention, novel AI-77 compounds and pharmaceutically acceptable, salts thereof, useful as anti-ulcer agents, are provided. The AI-77 compounds of this invention are represented by formulae (I) and (II)

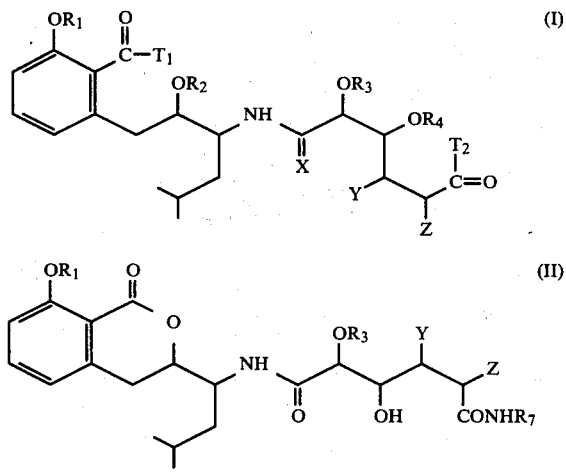

wherein: X is $NR_6$ or O; Y is $NHR_5$ or combines with Z to provide a link for bonding C and C; Z is H or combines with Y to provide a link for bonding C and C; $R_1$, $R_3$ and $R_5$ are each H, R', $-CH_2R$, or $-COR$; $R_6$ is H or R; $R_7$ is H, R or $CH_2R$; R is selected from the group consisting of a saturated or unsaturated straight or branched aliphatic group of $C_1$ to $C_{17}$, an aromatic group of $C_6$ to $C_{10}$, a bridged hydrocarbon group of $C_7$ to $C_{10}$, a monocyclic aliphatic group of $C_3$ to $C_8$, an aromatic-aliphatic (also sometimes referred to as "araliphatic") group of $C_7$ to $C_{15}$, a heterocyclic group containing 1 to 9 carbon atoms and a hetero atom selected from O, S and N and those which can be substituted with one or more groups selected from halogen, oxo, carboxyl, hydroxyl, a saturated or unsaturated straight or branched aliphatic group of $C_1$ to $C_5$, an aromatic group of $C_6$ to $C_{10}$, a monocyclic aliphatic group of $C_3$ to $C_8$, an aromatic-aliphatic group of $C_7$ to $C_{11}$, alkoxyl of $C_1$ to $C_5$, thioalkoxyl of $C_1$ to $C_5$, carboalkoxyl of $C_1$ to $C_6$, acyl of $C_1$ to $C_5$, acyloxy of $C_2$ to $C_6$ and a heterocyclic group containing 1 to 9 carbon atoms and a hetero atom selected from O, S and N; R' is the same as R exclusive of those groups wherein unsaturated carbon or tertiary carbon is directly bonded to O or N; $R_2$ is H, or combines with $T_1$ to provide a link for bonding C and O in a lactone ring; $T_1$ is OH or combines with $R_2$ to provide a link for bonding C and O in a lactone ring; $R_4$ is H or combines with $T_2$ to provide a link for bonding C and O in a lactone ring, and $T_2$ is OH or combines with $R_4$ to provide a link for bonding C and O in a lactone ring.

As a result of investigation of many microorganism cultures in search of novel anti-ulcer agents, it has been found that when strain AI-77, newly separated by us from soil and identified to belong to *Bacillus pumilus*, was cultivated aerobically on a medium, a substance having strong anti-ulcer activity was accumulated in the culture. Further studies have revealed that the substance comprises seven compounds, A, B, C, D, E, F and G which will be described hereinafter, forming the basis of the present invention.

BRIEF DESCRIPTION OF THE DRAWINGS

FIGS. 1 and 2 are the $^1H$ nuclear magnetic resonance spectrum and infrared absorption spectrum, respectively, of Compound A.

FIGS. 3 and 4 are the $^1H$ nuclear magnetic resonance spectrum and infrared absorption spectrum, respectively, of Compound B.

FIGS. 5 and 6 are the $^1H$ nuclear magnetic resonance spectrum and infrared absorption spectrum, respectively, of Compound C.

FIGS. 7 and 8 are the $^1H$ nuclear magnetic resonance spectrum and infrared absorption spectrum, respectively, of Compound D.

FIGS. 9 and 10 are the $^1H$ nuclear magnetic resonance spectrum and infrared absorption spectrum, respectively, of Compound F.

FIGS. 11 and 12 are the $^1H$ nuclear magnetic resonance spectrum and infrared absorption spectrum, respectively, of Compound G.

FIG. 13 is an infrared absorption spectrum of Compound E.

DETAILED DESCRIPTION OF THE INVENTION

The novel AI-77 compounds of this invention are represented by the formulae (I) and (II) are set forth above; R is a saturated straight alkyl of $C_1$ to $C_{17}$ such as methyl, ethyl, n-propyl, n-butyl, n-pentyl, n-hexyl, n-heptyl, n-octyl, n-undecyl, or n-heptadecyl; a branched saturated aliphatic group of $C_3$ to $C_{17}$ such as isopropyl, 2-methyl-propyl, 2-methylbutyl, 2-propylpentyl, 4-ethylheptyl, or 2,6,10-trimethyltetradecanyl; an unsaturated alkyl of $C_2$ to $C_{17}$ such as vinyl, allyl-1-propenyl, 2-propenyl, 2-butenyl, 1,3-butadienyl, 2-pentenyl, 8-heptadecenyl, 2-methylallyl, 2,6-dimethyl-2,6-heptadienyl, or 2,6,9-trimethyl-2,6,9-tridecatrienyl; an aromatic of $C_6$ to $C_{10}$ such as phenyl, naphthyl or azulenyl; a bridged hydrocarbon group of $C_7$ to $C_{10}$ such as norbornene, norbornane, camphor, or adamantoyl; a monocyclic aliphatic of $C_3$ to $C_8$ such as cyclopropyl, cyclobutyl, cyclopentyl, cyclohexyl, cycloheptyl or cyclooctyl; an aromatic-aliphatic of $C_{11}$ to $C_{15}$ such as benzyl, phenetyl, 2-phenylpropyl, naphthylmethyl, naphthylethyl, or 2,4-dimethyl-isopropyl-azulenyl; a heterocyclic group containing 1 to 9 carbon atoms and a hetero atom selected from O, S and N such as furyl, dihydrofuryl, tetrahydrofuryl, pyranyl, dihydropyranyl, thienyl, tetrazolyl, pyrrolyl, pyrrolidinyl, quinolyl, indolyl, indolinyl, piperidyl, morpholinyl, pyridyl, oxazolyl, oxazolidinyl, thiazolyl or thiazolydinyl, in which N-heterocyclic groups having a tertiary nitrogen atom substituted by carbon atoms are preferred among the N-heterocyclic groups. The groups mentioned above may have one or more substituents. Illustrative substituents are a halogen such as chlorine, bromine or fluorine; oxo; carboxyl; hydroxyl; a saturated or unsaturated straight or branched aliphatic of $C_1$ to $C_5$ such as methyl, ethyl, propyl, butyl, pentyl, isopropyl, 3-methylbutyl, isobutylene, propylene or acetylene; an aromatic of $C_6$ to $C_{10}$ such as phenyl, naphthyl, azulenyl or tropoyl; a monocyclic aliphatic of $C_3$ to $C_8$ such as cyclopropyl, cyclobutyl, cyclopentyl, cyclohexyl, cycloheptyl or cyclooctyl; an aromatic-aliphatic of $C_7$ to $C_{11}$ such as benzyl, phenetyl, 2-phenylpropyl, naphthylmethyl or p-(3-methyl)butylphenyl; an alkoxyl of $C_1$ to $C_5$ such as methoxy, ethoxy, pentoxy, 3-methylbutoxy or 3-methyl-2-butenoxy; a thioalkoxyl of $C_1$ to $C_5$ such as methylthio, ethylthio, 3-methylbutylthio or pentylthio; a carboalkoxyl of $C_1$ to $C_6$ such as methoxycarbonyl, pentoxycarbonyl or isobutoxycarbonyl; an acyloxy of $C_2$ to $C_6$ such as acetyloxy, propionyloxy, pentanoyloxy, hexanonyloxy, or crotonoyloxy; an acyl of $C_1$ to $C_5$ such as acetyl, propionyl, hexanoyl, or 3-methylbutanoyl; and a heterocyclic group containing 1 to 9 carbon atoms and a hetero atom selected from O, S and N such as furyl, dihydrofuryl, tetrahydrofuryl, pyranyl, dihydropyranyl, thienyl, tetrazolyl, pyrrolyl, pyrrolidinyl, quinolyl, indolyl, indolinyl, piperidino, morpholino, pyridyl, oxazolyl, oxazolydinyl, thiazolyl or thiazolydinyl. Preferred substituents on the straight alkyl are halogen, oxo, carboxy, alkoxy, thioalkoxy, carboalkoxy, acyloxy, monocyclic aliphatic, aromatic-aliphatic, aromatic and heterocyclic groups. Preferred substituents for the branched alkyl are halogen, alkoxy and thioalkoxy groups. Preferred substituents for the aromatic are alkyl, alkoxy, thioalkoxy, hydroxy, acyloxy and carboalkoxy, and these groups are also preferred as the substituent for the aromatic group of the aromatic-aliphatic. Preferred substituents for the monocyclic aliphatic are oxo, carboxyl, alkyl, alkoxyl, carboalkoxyl and acyloxyl. Preferred substituents for the heterocyclic group are alkyl, alkoxyl, acyl and carboxyl.

The AI-77 compounds defined above may also be used in the form of a pharmaceutically acceptable salts, such as salts of hydrohalogenic acid, phosphoric acid, sulfuric acid, oxalic acid, maleic acid, and organic sulfonic acids, such as dodecylsulfuric acid.

It has been found that the novel compound of this invention is useful as an anti-ulcer agent, anti-inflammatory agent, cholesterol lowering drug, anti-arrhythmic agent, vasodilator and as an intermediate for these medicines.

Typical AI-77 compounds can be represented by the following formulae, and can be obtained as a product of a fermentation process:

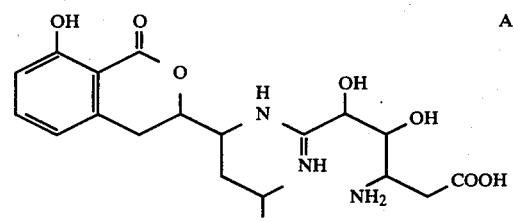

AI-77-A:

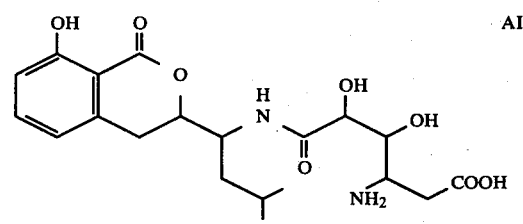

AI-77-B:

AI-77-C:

AI-77-D:

AI-77-F:

AI-77-G:

Like the compounds A, B, C, D, F and G, compound E is available as a fermentation product and its characteristics are as follows: Rf=0.55 in thin layer chromatography (TLC) on silica gel (e.g. D 5714 of Merck & Co., Inc.) using ethyl acetate as a developing system; maximum UV absorption in methanol=246 nm and 314 nm; IR absorption characteristics in KBr tab.=1755 $cm^{-1}$, 1645 $cm^{-1}$, and 1540 $cm^{-1}$.

Other compounds of the formulae (I) and (II) can be derived from the compounds A to G described above as a semi-synthetic product.

The physicochemical properties of the compounds A to G are set forth in the following tables. Table 1 shows the mass spectrum data, UV absorption, IR absorption, NMR and other characteristics of the hydrochloride of compound A. The compound is freely soluble in water, methanol, dimethylformamide, and dimethyl sulfoxide, sparingly soluble in a lower alcohol of $C_2$ to $C_3$ and dioxane, and substantially insoluble in ethyl acetate, chloroform, ether, hexane and benzene. The compound is very labile to heat and alkali.

TABLE 1

A - 77 - A.HCl

TABLE 1-continued

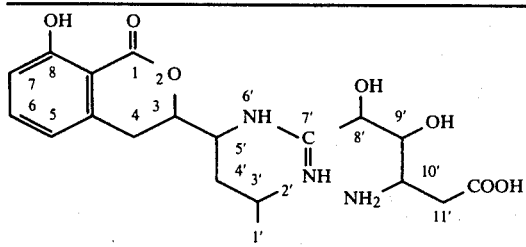

Mass: FD mass $(M + 1)^+ = 424$
Molecular formula $C_{20}H_{27}N_3O_7 \cdot HCl$ U.V. $\lambda_{max}^{MeOH}$: 246 nm ($\epsilon = 5.77 \cdot 10^3$) 314nm ($\epsilon = 4.11 \times 10^3$)

I.R. $\nu_{max}^{KBr}$: 1674 cm$^{-1}$, 1643 cm$^{-1}$, 1540 cm$^{-1}$, [See FIG. 2].

$^1$H N.M.R. (in CD$_3$OD (TMS)): [See FIG. 1.]
δ ppm and J (Hz)

| | | |
|---|---|---|
| H-1' | } | 0.92 (3H, d), $J_{1' \, or \, 2', \, 3'} = 6$ |
| H-2' | | 0.96 (3H, d), $J_{1' \, or \, 2', \, 3'} = 6.5$ |
| H-3' | } | 1.14 ~ 2.0 (3H, m) |
| H-4' | | |
| H-5' | | 4.36 (1H, m) |
| H-8' | | 4.19 (1H, d) $J_{8', \, 7'} = 7$ |
| H-9' | | 4.01 (1H, dd) $J_{9', \, 10'} = 4$ |
| H-10' | | 3.70 (1H, m) |
| H-11' | | 2.4 ~ 2.9 (2H, m) |
| H-3 | | 4.70 (1H, m) |
| H-4 | | 3.04 (2H, m) |
| H-5 | } | 6.77 (1H, d) 6.85 (1H, d) $J_{5,6} \, J_{6,7} = 8$ |
| H-7 | | |
| H-6 | | 7.47 (1H dd) |
| NH | | 7.74 d J = 8 (in d$_6$—DMSO) |
| NH | | 7.82 d J = 9 (in d$_6$=DMSO) |

$^{13}$C NMR (in d$_6$—DMSO):
δ ppm

| | | | |
|---|---|---|---|
| 21.4 | 39.0 | 81.0 | 140.8 |
| 23.3 | 48.2 | 108.4 | 161.0 |
| 24.0 | 49.8 | 115.4 | 169.2 |
| 29.0 | 71.2 | 118.7 | 177.5 |
| 32.1 | 71.6 | 136.6 | 177.7 |

Table 2 shows the mass spectrum data, UV absorption, IR absorption, NMR and other characteristics of the compound B. The compound is freely soluble in water, methanol, dimethylformamide and dimethyl sulfoxide, sparingly soluble in other lower alcohols, dioxane and tetrahydrofuran, and substantially insoluble in ethyl acetate, chloroform, ether, hexane and benzene. An aqueous solution of the compound is labile to alkali in which the hydrolysis of lactone proceeds gradually even at room temperature, by which AI-77 G is formed.

TABLE 2

AI - 77 - B

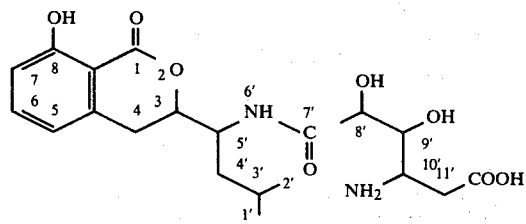

Mass: FD high mass $(M + 1)^+ = 425.1938$
Molecular formula $C_{20}H_{28}N_2O_8$ U.V. $\lambda_{max}^{MeOH}$: 246nm ($\epsilon = 6.25 \times 10^3$) 314nm ($\epsilon = 4.45 \times 10^3$)

C.D. MeOH: $\Delta\epsilon_{325} = -0.42$, $\Delta\epsilon_{306} = -0.67$, $\Delta\epsilon_{257} = -3.3$ I.R. $\nu_{max}^{KBr}$: 1660 cm$^{-1}$, 1640 cm$^{-1}$, 1520 cm$^{-1}$ [See FIG. 4]

$^1$H N.M.R. (in CD$_3$OD (TMS)): [See FIG. 3]
δ ppm and J (Hz)

| | | |
|---|---|---|
| H-1' | } | 0.90 (3H, d) 0.95 (3H, d) $J_{1' \, or \, 3'} = 6$ $J_{1' \, or \, 2', \, 3'} = 6.5$ |
| H-2' | | |
| H-3' | } | 1.1 ~ 2.0 (3H, m) |
| H-4' | | |
| H-5' | | 4.30 (1H, m) |
| H-8' | | 4.14 (1H, d) $J_{8', \, 9'} = 7$ |
| H-9' | | 3.92 (1H, dd) $J_{9', \, 10'} = 4$ |
| H-10' | | 3.62 (1H, m) |
| H-11' | | 2.55 (1H, m) $J_{11', \, 11''} = 16$ |
| H-3 | | 4.62 (1H, m) |
| H-4 | | 3.0 (2H, m) |
| H-5 | } | 6.75 (1H, d) 6.81 (1H, d) $J_{5,6}, J_{6,7} = 8$ |
| H-7 | | |
| H-6 | | 7.42 (1H, dd) |
| —NH— | | 8.07 d J = 8 (in d$_6$—DMSO) |

$^{13}$C N.M.R:
δ ppm

| in d$_6$ — DMS0 | | | | in CD$_3$OD | | | |
|---|---|---|---|---|---|---|---|
| 22.6 | 39.6 | 82.0 | 141.7 | 21.3 | 40.0 | 81.8 | 140.4 |
| 24.4 | 49.7 | 109.1 | 161.9 | 23.0 | 49.3 | 108.5 | 162.3 |
| 25.1 | 51.5 | 116.3 | 170.1 | 25.1 | 51.5 | 116.0 | 170.2 |
| 30.1 | 72.5 | 119.5 | 173.8 | 30.0 | 71.7 | 118.8 | 174.0 |
| 34.5 | 72.5 | 137.3 | 175.7 | 32.4 | 73.0 | 136.8 | 174.0 |

Table 3 shows the mass spectrum data, UV absorption, IR absorption, NMR and other characteristics of the compound C. The compound is freely soluble in lower alcohols, dimethylformamide, dimethyl sulfoxide and dioxane, sparingly soluble in chloroform and ethyl acetate, and substanitally insoluble in water, ether, hexane and benzene. It is also as labile to alkali is AI-77-B.

TABLE 3

AI - 77 - C

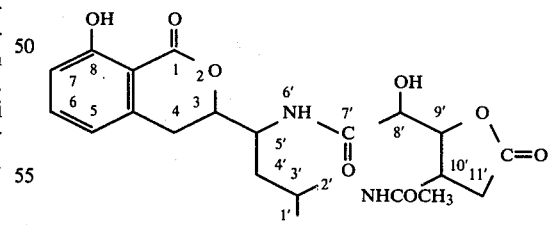

Molecular formula: $C_{22}H_{28}N_2O_8$

U.V. $\lambda_{max}^{MeOH}$: 246nm 314nm

I.R. $\nu_{max}^{KBr}$: 1765 cm$^{-1}$, 1653 cm$^{-1}$, 1535 cm$^{-1}$ [See FIG. 6]

$^1$H N.M.R. (in d$_6$—DMSO (TMS)): [See FIG. 5]
δ ppm and J (Hz)

| | | |
|---|---|---|
| H-1' | } | 0.82 (3H, d) $J_{1' \, or \, 2', \, 3'} = 7$ |

TABLE 3-continued

| | |
|---|---|
| H-2' | 0.82 (3H, d) $J_{1'\ or\ 2',\ 3'} = 7$ |
| H-3' H-4' | 1.0 ~ 1.90 (3H, m) |
| H-5' | 4.18 (1H, m) |
| H-8' | 4.28 (1H, d) $J_{8',\ 9'} = 3$ |
| H-9' | 4.61 (1H, ) |
| H-10' | 4.32 (1H, m) |
| H-11' | 2.23 (1H, dd) $J_{11',\ 10'} = 2\ J_{11',\ 11''} = 18$ |
| H-11''' | 2.90 (1H, dd) $J_{11'',\ 10'} = 9$ |
| H-3 | 4.66 (1H, m) |
| H-4 | 2.90 (2H, d) $J_{4,\ 3} = 8$ |
| H-5 | 6.77 (1H, d) $J_{5\ or\ 7,\ 6} = 8$ |
| H-7 | 6.81 (1H, d) $J_{5\ or\ 7,\ 6} = 9$ |
| H-6 | 7.44 (1H, dd) |
| OH—C8' | 6.18 d $J_{8',\ OH} = 6$ |
| NH—C10' | 7.85 d $J = 8$ |
| NH-6' | 8.36 d $J = 7$ |
| OH—C8 | 10.74 s |
| CH3CONH—C10' | 1.69 (3H, s) |

Table 4 shows the mass spectrum data, UV absorption, IR absorption, NMR and other characteristics of the compound D. The compound is soluble in lower alcohol, dimethylformamide, dimethyl sulfoxide, dioxane, chloroform, and ethyl acetate, and substantially insoluble in water, ether, hexane and benzene. It is also as labile to alkali as AI-77-B.

TABLE 4

AI - 77 - D

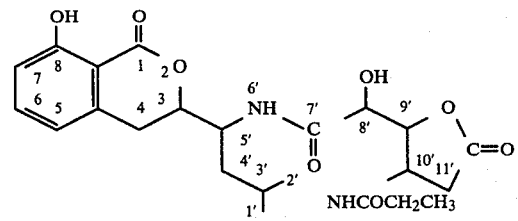

Molecular formula: $C_{23}H_{30}N_2O_8$

U.V. $\lambda_{max}^{MeOH}$: 246nm, 314nm

I.R. $\nu_{max}^{KBr}$: 1790 cm$^{-1}$, 1645 cm$^{-1}$, 1540 cm$^{-1}$ [See FIG. 7]

$^1$H N.M.R (in d$_6$—DMSO (TMS)): [See FIG. 7]
ppm and J (Hz)

| | |
|---|---|
| H-1' | 0.82 (3H, d) $J_{1'\ or\ 2',\ 3'} = 7$ |
| H-2' | 0.82 (3H, d) $J_{1'\ or\ 2',\ 3} = 7$ |
| H-3' H-4' | 1.0 ~ 1.90 (3H, m) (3H, m) |
| H-5' | 4.18 (1H, m) |
| H-8' | 4.28 (1H, d) $J_{8',\ 9'} = 3$ |
| H-9' | 4.6 (1H ) |
| H-10' | 4.32 (1H, m) |
| H-11' | 2.23 (1H, dd) $J_{11',\ 10'} = 2\ J_{11',\ 11''} = 18$ |
| H-11''' | 2.90 (1H, dd) $J_{11'',\ 10'} = 9$ |
| H-3 | 4.66 (1H, m) |
| H-4 | 2.90 (2H, d) $J_{4,3} = 8$ |
| H-5 | 6.77 (1H, d) $J_{5\ or\ 7,6} = 8$ |
| H-7 | 6.81 (1H,d) $J_{5\ or\ 7,\ 6} = 9$ |
| H-6 | 7.44 )1H, dd) |
| OH—C8' | 6.18 d $J_{8',\ OH} = 6$ |
| NH—C10' | 7.85 d $J = 8$ |

TABLE 4-continued

| | |
|---|---|
| NH-6' | 8.36 d $J = 7$ |
| OH—C8 | 10.74 s |
| CH3CH2CONH— | 1.94 (2H, q) J 32  8 |
| CH3CH2CONH | 0.88 (3H, t) |

Table 5 shows the UV absorption and IR absorption of the compound E. The compound is freely soluble in ethyl acetate, chloroform, dimethylformamide and dimethyl sulfoxide, sparingly soluble in lower alcohol and dioxane, and substantially insoluble in water, hexane and benzene.

TABLE 5

| | | | |
|---|---|---|---|
| U.V. $\lambda_{max}^{MeOH}$: | 246 nm | 314 nm | |
| I.R. $\nu_{max}^{CHCl_3}$: | 1790 cm$^{-1}$, | 1765 cm$^{-1}$, | 1730 cm$^{-1}$, |
| | 1680 cm$^{-1}$, | 1525 cm$^{-1}$ | [See FIG. 13] |

Table 6 shows the mass spectrum, UV absorption, IR absorption, and NMR of the compound F. The compound is freely soluble in ethyl acetate, chloroform, dimethylformamide and dimethyl sulfoxide, sparingly soluble in lower alcohols and dioxane, and substantially insoluble in water, hexane and benzene. The compound is as labile to alkali as AI-77-B.

TABLE 6

AI - 77 - F

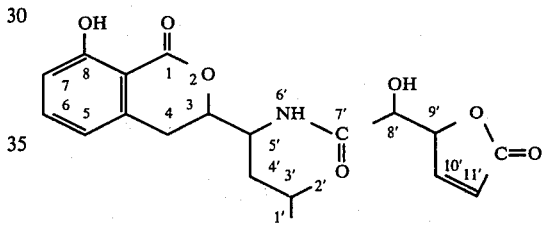

Mass: hight mass M$^+$ 389.1474
Molecular formula $C_{20}H_{23}N_1O_7$

U.V. $\lambda_{max}^{MeOH}$: 243nm, 312nm

C.D. dioxane: $\Delta\epsilon_{327} = -0.31\ \Delta\epsilon_{303} = -0.47\ \Delta\epsilon_{258} = -4.5$ I.R. $\nu_{max}^{MeOH}$: 1790 cm$^{-1}$, 1755 cm$^{-1}$, 1670 cm$^{-1}$, 1535 cm$^{-1}$ [See FIG. 10]

$^1$H N.M.R. (in d$_6$—DMSO (TMS)): [See FIG. 9]
δ (ppm) and J (Hz)

| | |
|---|---|
| H-1' H-2' | 0.85 (3H, d) 0.91 (3H, d) |
| H-3' H-4' | 1.11 ~ 1.90 (3H, m) |
| H-5' | 4.18 (1H, m) |
| H-8' | 4.40 (1H, dd) $J_{8',\ 9'} = 3\ J_{8'}$, —OH = 6 |
| H-9' | 5.35 (1H, dd) $J_{9',\ 10'} = 2$ |
| H-10' | 6.24 (1H, dd) $J_{10',\ 11'} = 6$ |
| H-11' | 7.55 (1H, d) |
| H-3 | 4.68 (1H, dd) $J_{3,\ 4} = 8$ |
| H-4 | 2.97 (2H, d) |
| H-5 H-7 | 6.80 (2H, d) $J_{5,\ 6},\ J_{6,\ 7} = 8$ |
| H-6 | 7.50 (1H, dd) |
| NH | 7.78 d $J_{NH,5'} =: 10.5$ |
| OH—C'8 | 617 d |
| OH—C8 | 10.75 s |

$^{13}$C NMR (in d$_6$—DMSO):

TABLE 6-continued

| | δ ppm | | |
|---|---|---|---|
| 21.16 | 48.48 | 115.56 | 154.73 |
| 23.24 | 70.81 | 118.76 | 161.09 |
| 24.02 | 80.91 | 121.87 | 169.10 |
| 29.07 | 84.26 | 136.67 | 170.12 |
| 38.77 | 108.43 | 140.32 | 173.22 |

Table 7 shows the molecular formula, UV absorption, IR absorption and other characteristics of compound G. The compound is freely soluble in water and slightly soluble in organic solvents. It is relatively stable in aqueous solution.

TABLE 7
AI-77-G

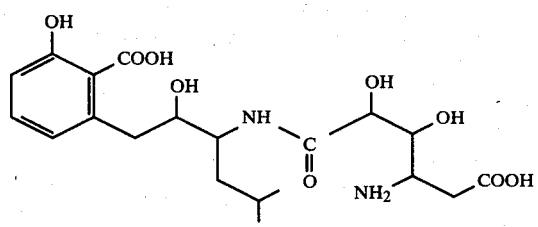

| Molecular weight: | $C_{20}H_{30}N_2O_9$ |
|---|---|
| $U.V._{\lambda max}^{KBr}$: | 245 nm (sh) 300 nm |
| $I.R._{\nu max}^{KBr}$: | 1650 cm$^{-1}$, 1583 cm$^{-1}$ [See FIG. 12] |
| $^1H$ N.M.R.: | [See FIG. 11] |

All measured values in Tables 1 to 7 are before correction. The Rfs of compounds A to G on TLC are indicated in Table 8 below.

TABLE 8

TLC analysis of AI-77-A, B, C, D, F, G and E
developing plate: silica gelplate (5714 of Merck & Co., Inc.)
Developing system: (1) ether:ethyl acetate = 7:3 v/v
(2) ethyl acetate
(3) chloroform:methanol = 1:1 v/v
(4) n-butanol:acetone:water = 4:5:1 v/v

| Compound | Developing system* | | | |
|---|---|---|---|---|
| | (1) | (2) | (3) | (4) |
| A | none | placing point | 0.11 | 0.52 |
| B | none | placing point | 0.43 | 0.27 |
| C | 0.09 | 0.28 | 0.85 | 0.94 |
| D | 0.22 | 0.47 | 0.85 | 0.94 |
| E | 0.26 | 0.55 | 0.85 | 0.94 |
| F | 0.48 | 0.68 | 0.92 | 0.96 |
| G | none | placing point | 0.35 | 0.39 |

*(migration of solvent = 1.00)

A novel A-77 compound of this invention is advantageously produced by cultivating the strain AI-77 mentioned above, but it can also be obtained as an isolate from the culture of other A-77 compound-producing microorganisms that belong to Bacillus. Common knowledge about the cultivation of microorganisms of Bacillus can be relied upon in the cultivation of the strain AI-77 and other A-77 compound-producing microorganisms of Bacillus. To be more specific, these microorganisms are cultivated aerobically about at 25° to 40° C. on a medium containing a nitrogen source, carbon source, inorganic salt, vitamin, amino acid, nucleic acid related substance and any other substance that is necessary for the growth of such microorganisms. Large-scale cultivation is advantageously performed under aeration agitation.

The mycological properties of strain AI-77 (FERM. P No. 4066, ATCC No. 31650) are indicated below:

Mycological Properties (a) Nature of growth on the following various media:

(1) Bouillon: The medium becomes practically turbid throughout and forms no film.

(2) Bouillon agar plate culture: The colony is generally smooth, and sometimes a rough flat colony is formed. Opaque to translucent. First ivory, then white, finally cream-colored. No pigment is formed.

(3) Glucose bouillon agar medium: The microorganism grows better on this medium than on bouillon agar medium. The appearance of the colony is the same as on bouillon agar medium.

(4) Gelatin medium: Gelatin liquefies gradually.

(5) Peptone water: The growth of microorganism is slightly inhibited and the medium becomes slightly turbid.

(6) Litmus milk: The microorganism does not coagulates or peptonize milk. There is observed no change in litmus.

(7) Potato medium: The microorganism spreads in a tawny colony with small wrinkles.

The morphological properties of the microorganism on a glucose bouillon agar medium are such that the cell is a short rod 0.5~0.9×0.5~2.0μ in size, Gram variable, and forms elliptical to cylindrical shaped spores which are generally positioned in the center of the cell and whose sides do not appreciably bulge outward.

(b) Physiological properties (1) Optimum growth conditions: pH 5 to 8, 27° to 35° C., aerobic (2) Growth conditions: pH 5.0 to 10.0, 10° to 55° C.

(3) Gram staining: variable (4) Acid resistance: none (5) Methyl Red test: positive (6) Voges-Proskauer reaction: positive (7) Formation of indole not observed (8) Formation of hydrogen sulfide little observed.

(9) Formation of ammonia not observed.

(10) Reduction of nitrate salt not observed.

(11) Formation of catalase is active.

(12) Gradually liquefies gelatin.

(13) Does not hydrolyze starch.

(14) Utilizes citric acid.

(15) Grows on 7% NaCl medium.

(16) Does not reduce methylene blue.

(17) Utilizes urea very slightly.

(c) Utilization of carbon sources

The microorganism forms an acid by utilizing fructose, saccharose, glucose and mannitol. It slightly utilizes mannose and trehalose to form an acid. It does not utilize arabinose, xylose, galactose, lactose, maltose, raffinose, sorbitol, inositol, glycerol, α-methylglycoside, inulin, dextrin, starch or cellulose. Neither carbon source generates a detectable gas.

Checking the above described properties against Bergey's *Manual of Determinative Bacteriology*, 7th and 8th Eds. shows that the microorganism under discussion has properties that generally agree with those of *Bacillus pumilus* in spite of a few differences (e.g. it does not form an acid from arabinose or xylose, or it does not peptonize or coagulate milk). Therefore the microorganism has been identified as a strain that belongs to *Bacillus pumilus*, and named it *Bacillus pumilus* AI-77 in the absence of a known strain indentical with it. The microorgansim has been deposited with the Fermentation Research Institute, Agency of Industrial Science and Technology, Japan, under FERM P No. 4066 on May 20, 1977, and also has been deposited with American Type Culture Collection, U.S.A., as ATCC No. 31650 on June 16, 1980. All natural and artificial variants of *Bacillus pumilus* AI-77 that have the ability to produce AI-77 compounds can be used in this invention.

The production of Compounds A to G by cultivation and their recovery from the culture are performed with the specific means that will be described hereunder. When A- to G-producing microorganisms are cultivated aerobically for a period of time on a liquid medium containing nutrient sources required by the microorganisms, compounds A to G are accumulated in the culture. The compounds are recovered from the culture with combinations of purifying means that utilize the physicochemical properties of the compounds. Nutrient sources used in the fermentation are carbon sources, nitrogen sources, inorganic salts, as well as vitamins and amino acids (optional) and other nutrient elements necessary for the growth of the microorganism used. Examples of the carbon source are glucose, sucrose, fructose, mannitol, organic acid, molasses, starch and glycerin. Examples of the nitrogen source are corn steep liquor, soybean meal, pharmamedia, yeast extract, meat extract, protein hydrolyzates such as peptone and Casamino acid, amino acid and ammonium salt. Examples of the inorganic salt are those that contain metal ions such as sodium, potassium, calcium, magnesium and iron, as well as ion-containing salts of ammonia, phosphoric acid, sulfuric acid, hydrochloric acid, carboxylic acid, etc. The medium must also contain essential nutrient elements necessary for the growth of the microorganism concerned. Vitamins, amino acids and nucleic acid related elements are incorporated in the medium as required. AI-77 compound-producing microorganisms grow under various conditions. For example, they are capable of growing on a variety of media having a wide range of initial pHs. However, the medium on which a fermentation starts has a pH of 6 to 8, preferably from 6 to 7, and the pH of the medium generally varies over a narrow range as the microorganism grows. Cultivation is performed aerobically at 25° to 40° C. for a period of 12 to 168 hours. The incubation period is set suitably according to which compound is to be produced. For the incubation period suitable to a specific compound, see below. The AI-77 compound-producing microorganism can be incubated on a slant agar, in a shake flask, or within a medium- to large-size fermentation tank. Fermentation under aeration-agitation is preferred for large-scale production. For incubation with aeration-agitation under aerobic conditions, a defoaming agent such as silicone or polypropylene glycol derivative may be added to the medium with advantage, and this is effective for achieving a greater accumulation of compounds A to G. The total accumulation of compounds A to G can be monitored by the increase in the UV absorption of the culture filtrate at 314 mµ. The production of each of the compounds A to G can be monitored by performing TLC or HPLC (high pressure liquid chromatography) on the culture filtrate or the organic extract thereof.

The compounds A to G produced under aerobic fermentation conditions can be substantially isolated from the fermentation broth by combining proper means such as ion exchange resin, macro-reticulate resin, gel filtration agent, chromatography on adsorbent and solvent extraction, using the respective physicochemical properties of the compounds. Compound A is isolated as follows: the filtrate of the culture obtained by a 12- to 48-hr incubation under aerobic conditions is adsorbed on a weak acidic cation exchange resin, e.g., IRC-50 (H type) produced by Rohm and Haas, eluted with a dilute acid, and the eluate is adsorbed on a macro-reticulate resin, e.g., Amberlite XAD-2 or XAD-4 of Rohm and Haas or Dia-ion HP resins of Mitsubishi Chemical Industries Limited, and eluted with water or an organic solvent or a mixture thereof. Suitable organic solvents are those having affinity for water such as alcohols of $C_1$ to $C_4$, acetone, dioxane and tetrahydrofuran. Compound A can be desorbed from the macro-reticulate resin with water containing more than 10% of methanol. Hence, by concentrating the eluate in vacuum and freeze-drying the concentrate, compound A can be obtained as a white powder of a salt of the acid used in the elution of the ion exchange resin. Repeated purification with the macro-reticulate resin gives compound A of higher purity. Compounds B to G are isolated as follows: the filtrate of the culture obtained by a 24- to 168-hr incubation under aerobic conditions is adsorbed on a macro-reticulate resin and subjected to gradient elution with a mixture of water and increasing concentrations of organic solvent. The macro-reticulate resin and organic solvent used may be the same as those used in the recovery of compound A. Compound G is most easily desorbed from the macro-reticulate resin, then comes B followed by C, D, E and F in that order. Therefore, the respective compounds can be isolated and purified by properly selecting the polarity of the macro-reticulate resin and the eluting solvent. To be more specific, Compound G is desorbed with water containing 0 to 10% of an organic solvent; B is desorbed with water continuing 20 to 40% of an organic solvent; and C to F are sequentially eluted with higher concentrations of the solvent. The eluates containing G and B are again chromatographed to obtain the respective compounds separately. Another effective method for isolating compounds C to F is to first elute them all together from a macro-reticulate resin with at least 80% of an organic solvent, concentrate the eluate into a powder which is then chromatographed on a column of adsorbent such as silica gel or magnesium silicate. Illustrative eluting solvents are ethyl ether, acetate ester, chloroform and alcohols; they are mixed in suitable proportions and by gradually increasing the polarity of the solvent system, independent elution fractions of F, E, D and C are obtained. Concentating the respective fractions gives compounds F to C. It is to be understood that these compounds can be isolated separately by preparative TLC or preparative HPLC on the same theory of operation.

Next, methods of synthesizing compounds of (I) other than compounds A, B, C, D, F and G are described. First, methods (1) to (23) for producing compounds of (I) wherein X is O are described. Methods (1) to (21) produce compounds of the formula (IIIa) wherein $R_1$, $R_3$ and $R_5$ are the same as defined above.

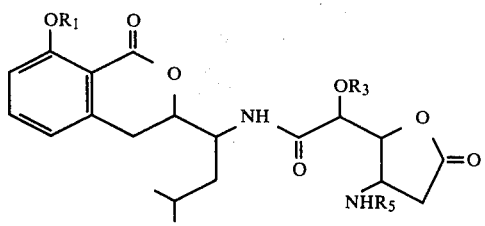

[IIIa]

(1) A compound of (IIIa-1) wherein $R_1$ and $R_3$ of the formula (IIIa) are each H and $R_5$ is RCO— is obtained by acylating the above described AI-77-B according to the conventional acylating technique. The product can be typically identified by comparing the UV absorption, IR absorption, NMR and mass spectrum data of the starting material with that of the product. This identification technique is also employed in the methods of synthesis to be described hereunder. A typical method of acylation uses an acid anhydride [(RCO)$_2$O] or an acid chloride (RCOCl) or both acid (RCOOH) and a dehydration-condensation agent (e.g. dicyclohexyl carboimide). Reaction at 0° to 25° C. using 1- to 2-fold mols of an acylating agent permits an acyl group to be introduced in $R_5$ with high selectivity.

(2) A compound of (IIIa-2) wherein $R_1$ of the formula (IIIa) is H, $R_3$ is RCO— and $R_5$ is RCO— is obtained by reaction at 25° to 80° C. in a pyridine solvent containing an excess [3 to 20 mol of (IIIa-1)] of an acid anhydride [(RCO)$_2$O] in the presence of a Lewis acid. If an acid chloride is used as an acylating agent, the reaction is performed at a temperature in the range of from room temperature to 40° C. using 1 to 5 mols of the chloride per mol of (IIIa-1) in a pyridine solvent.

(3) A compound of (IIIa-3) wherein $R_1$, $R_3$ and $R_5$ of the formula (IIIa) are each RCO— is obtained by acylating the compound (IIIa-2) under more regorous conditions than in the method (2). To be more specific, the compound (IIIa-2) is reacted with 1- to 30-fold mols of an acid anhydride [(RCO)$_2$O] or acid chloride (RCOCl) at 40° to 100° C. in a solvent system comprising a mixture of pyridine or tertiary amine with a non-protonic solvent.

As shown in the description of methods (1) to (3), an acyl group is introduced in $R_5$ of the compound (IIIa) faster than in $R_3$, and is introduced in $R_3$ faster than in $R_1$, and in each case, the selectivity of introduction of the acyl group is high.

(4) A compound of (IIIa-4) wherein $R_1$, $R_3$ and $R_5$ of the formula (IIIa) are RCO—, H and RCO—, respectively, is produced as follows: the compound (IIIa-1) is dissolved in an inert solvent, preferably a mixture of a non-protonic polar solvent and pyridine or tertiary amine, 1.5 to 15 mols of carbobenzoxychloride is added to the solution, and the mixture is heated at a temperature in the range of from room temperature to 80° C. By so doing, a carbobenzoxy group is introduced in the alcoholic OH group with high selectivity. The product is then acylated in a conventional manner, for example, it is reacted with an excess (1- to 30-times mols) of an acid anhydride [(RCO)$_2$O] at 40° to 100° C. in pyridine or tertiary amine and a non-protonic solvent. The acylated product is subjected to the conventional catalytic reduction to remove the carbobenzoxy group, thereby obtaining the compound (IIIa-4).

(5) A compound (IIIa-5) wherein $R_1$, $R_3$ and $R_5$ of the formula (IIIa) are R' or —CH$_2$R, H and RCO—, respectively, is produced as follows: the compound (IIIa-1) is dissolved in an inert solvent which optionally contains a small amount of alcohol and reacted with an excess of a diazo compound (R'N$_2$) or (RCH$_2$N$_2$) to introduce with high selectivity a group R' or RCH$_2$ in a phenolic OH group in the absence of a catalyst. Applicable diazo compounds are described in *Organic Functional Group Preparations*, edit. Alfred T. Blomquist Academic Press, New York and London, 1968, pp. 383-407. The compound R'N$_2$ or RCH$_2$N$_2$ can also be prepared by a known method.

(6) A compound of (IIIa-6) wherein $R_1$ of the formula (IIIa) is R' or —CH$_2$R, $R_3$ is RCO, and $R_5$ is RCO— is obtained by reacting the compound of (IIIa-2) with a diazo compound (R'N$_2$) in the manner described for method (5) or acylating the compound of (IIIa-5).

(7) A compound of (IIIa-7) wherein $R_1$ of the formula (IIIa) is R' or —CH$_2$R, $R_3$ is R' or CH$_2$R, and $R_5$ is RCO— is synthesized by introducing an alkyl group in the alcoholic OH group of the compound of (IIIa-5) by means of reaction with a diazo compound (R'N$_2$ or RCH$_2$N$_2$) in the presence of a catalyst (boron fluoride etherate).

As shown by the description of the methods (5) and (7), the diazo compound (R'N$_2$ or RCH$_2$N$_2$) is used to introduce an alkyl group in the phenolic OH group of the compound of (IIIa-1) with high selectivity, and then both the diazo compound and catalyst (boron fluoride etherate) are used to introduce an alkyl group in the alcoholic OH group.

(8) A compound of (IIIa-8) wherein $R_1$ of the formula (IIIa) is H, $R_3$ is R' or RCH$_2$ and $R_5$ is RCO— is synthesized as follows: first, phenyldiazomethane is used to introduce a protective benzyl group in the phenolic OH group of the compound of (IIIa-1) by means of the reaction described for the method (5), an alkyl group is introduced in the alcoholic OH group by the means of the reaction described for the method (7), and the benzyl group is removed by the conventional catalytic reduction.

(9) A compound of (IIIa-9) wherein $R_1$ of the formula (IIIa) is RCO—, $R_3$ is R' or RCH$_2$, and $R_5$ is RCO— is synthesized by acylating the phenolic OH group of the compound (IIIa-8) following the reaction described for the method (3).

(10) A compound of (IIIa-10) wherein $R_1$, $R_3$ and $R_5$ of the formula (IIIa) are H, RCO and H, respectively, is synthesized as follows: compound AI-77-B is reacted with 2- to 3-fold mols of carbobenzoxychloride in the presence of tertiary amine at room temperature to obtain a compound wherein $R_5$ is Ph—CH$_2$—OOC—. The compound is subjected to the reaction described for the method (2) to produce a compound wherein the alcoholic OH group is acylated, $R_1$ is H, $R_3$ is RCO— and $R_5$ is φ—CH$_2$—OOC—, and the resulting compound is subjected to catalytic reduction.

(11) A compound of (IIIa-11) wherein $R_1$, $R_3$ and $R_5$ of the formula (IIIa) are RCO—, RCO— and H, respectively, is synthesized as follows: the intermediate obtained by the method (10) wherein $R_1$ is H, $R_3$ is RCO— and $R_5$ is Ph—CH$_2$—OOC— is subjected to acylation of $R_1$ in the manner described for the method (4), and the acylated product is subjected to catalytic reduction.

(12) A compound of (IIIa-12) wherein $R_1$, $R_3$ and $R_5$ of the formula (III-a) are —COR, H and H, respectively, is synthesized as follows: according to the first method, AI-77-B is reacted with 5- to 30-fold mols of carbobenzoxychloride at a temperature between room temperature and 80° C. in the presence of tertiary amine to form a compound wherein $R_3$ and $R_5$ are each —$COCH_2Ph$. The $R_1$ of the compound is acylated in the manner described for the method (4), followed by catalytic reduction to obtain the end compound. According to the second method, AI-77-B is reacted with 5- to 30-fold mols of trichloroacetyl chloride at a temperature between room temperature and 80° C. in the presence of tertiary amine to form a compound wherein $R_1$, $R_3$ and $R_5$ are H, —$COCCl_3$ and —$COCCl_3$, respectively. The $R_1$ of the compound is converted to —COR in the manner described for the method (4), followed by hydrolysis with alkali in a controlled pH range of 8 to 12 at room temperature for a period of 2 to 24 hours. Then, the compound is lactonized under the conditions described for method (24) (to be described later) and by distilling the solvent off under acidic conditions, the end compound of (IIIa-12) is produced.

(13) A compound of (IIIa-13) wherein $R_1$ of the formula (IIIa) is R′ or $RCH_2$, $R_3$ is H and $R_5$ is H is produced by the following illustrative method: AI-77-B is subjected to the reaction of the method (1) to introduce —$COCCl_3$ at $R_5$, then subjected to the reaction of the method (5) to introduce R′ at $R_1$, and the resulting compound is subjected to alkali hydrolysis and lactonization that constitute the second stage of the second method (12) above.

(14) A compound of (IIIa-14) wherein $R_1$ of the formula (IIIa) is R′ or $RCH_2$, $R_3$ is RCO— and $R_5$ is H is synthesized by one of the following two methods: according to the first method: AI-77-B is subjected to the reaction of the method (1) to introduce —$COCCl_3$ at $R_5$, then subjected to the reaction of the method (2) to introduce RCO— at $R_3$, and subjected to the reaction of the method (6) to introduce R′ or $RCH_2$ at $R_1$. The resulting compound wherein $R_1$ is R′ or $RCH_2$, $R_3$ is RCO— and $R_5$ is $Cl_3CCO$— is subjected to alkali hydrolysis and lactonization in the manner described for the method (13). According to the second method, the compound obtained as an intermediate in the method (10) wherein $R_1$ is H, $R_3$ is RCO— and $R_5$ is Ph—$CH_2$—OOC— is subjected to the reaction of the method (6) to introduce R′ or $RCH_2$ at $R_1$, and the resulting compound is catalytically reduced to produce the end compound.

(15) A compound of (IIIa-15) wherein $R_1$ of the formula (IIIa) is R′ or $RCH_2$, $R_3$ is R′ or $RCH_2$, and $R_5$ is H is produced by the following illustrative method: AI-77-B is subjected to the reaction of the method (1) to introduce —$COCCl_3$ at $R_5$, then subjected to the reaction of the method (5) to introduce R′ or $RCH_2$ at $R_1$, and finally subjected to the reaction of the method (7) to introduce R′ or $RCH_2$ at $R_3$. The resulting compound is hydrolyzed with alkali in a controlled pH range of from 8 to 12 at room temperature for a period of from 2 to 24 hours. Then, the compound is lactonized under the conditions described for the method (24) (to be described later) and by distilling the solvent off under acidic conditions, the end compound of (IIIa-15) is produced.

(16) A compound of (IIIa-16) wherein $R_1$ of the formula (IIIa) is H, $R_3$ is R′ or $RCH_2$, and $R_5$ is H can be synthesized as follows: according to the first method, AI-77-B is reacted with 2- to 3-fold mols of carbobenzoxychloride at room temperature in the presence of tertiary amine to introduce Ph—$CH_2$—OOC— at $R_5$, then reacted with an excess of phenyldiazomethane to introduce a benzyl group at $R_1$, and the compound is reacted with a diazo compound (R′$N_2$ or $RCH_2N_2$) in the presence of boron fluoride etherate to introduce R′ or $RCH_2$ at $R_3$, and the compound is catalytically reduced to eliminate the benzyl group and carbobenzoxyl group. According to the second method, AI-77-B is subjected to the reaction of the method (4) to trichloroacetylate both $R_1$ and $R_5$, and reacted with a diazo compound (R′$N_2$ or $RCH_2N_2$) in the presence of boron fluoride etherate to introduce R′ or $RCH_2$ at $R_3$, and the resulting compound is hydrolyzed with alkali to obtain the end compound.

(17) A compound of (IIIa-17) wherein $R_1$ of the formula (IIIa) is RCO—, $R_3$ is R′ or $RCH_2$, and $R_5$ is H is synthesized as follows: according to the first method, a compound wherein $R_1$ is RCO—, $R_3$ is R′ or $RCH_2$ and $R_5$ is —$COCCl_3$ is synthesized by the method (9), and the compound is hydrolyzed with alkali and lactonized as shown in the description of the method (15). According to the second method, the compound (IIIa-16) is reacted with 2- to 3-fold mols of carbobenzoxychloride at room temperature in the presence of tertiary amine to introduce a carbobenzoxyl group at $R_5$, then subjected to the reaction of the method (3) to introduce an acyl group at $R_1$, and finally the compound is catalytically reduced to eliminate the carbobenzoxyl group.

(18) A compound of (IIIa-18) wherein $R_1$, $R_3$ and $R_5$ of the formula (IIIa) are H, H and —$CH_2R$, respectively, is synthesized from the compound (IIIa-1) in the following manner: a solution or dispersion of the compound (IIIa-1) in dichloromethane is mixed with 1- to 2-fold mols of a solution of triethyloxonium tetrafluoroborate in dichloromethane and the mixture is let stand at room temperature for a period of from 1 to 24 hours, whereupon iminoether is formed in the amide portion of $R_5$ with high selectivity. The solvent which is dichloromethane is replaced by dried ethanol after optionally isolating the resulting compound. One to three mols, preferably 1.5 to 2 mols, of sodium boron hydride per mol of the added triethyloxonium tetrafluoroborate are added under cooling with ice, and the reaction mixture is left to stand for 5 to 30 minutes, and treated with a mineral acid to be rendered acidic. The resulting product is a compound of (IIIa-18). It is very surprising that in the reaction between the compound (IIIa-1) and triethyloxonium tetrafluoroborate, the desired reaction should occur at the amido group of —NHCOR with high selectivity in spite of the presence of two amido groups. We have also confirmed that the reaction does not require the introduction of a protective group for the phenolic OH group or alcoholic OH group.

(19) Compounds of (IIIa-19) through (IIIa-26) wherein $R_5$ of the formula (IIIa) is R—$CH_2$— can be synthesized via the reaction of the method (18) from compounds (IIIa-2) through (IIIa-9), respectively, wherein $R_1$ and $R_3$ are the same as in the end compounds and $R_6$ is RCO—. See Table 9 below.

TABLE 9

| Compound | $R_1$ | $R_3$ | $R_5$ |
|---|---|---|---|
| IIIa-19 | H | RCO— | R—$CH_2$ |
| IIIa-20 | RCO— | RCO— | R—$CH_2$ |
| IIIa-21 | RCO— | H | R—$CH_2$ |
| IIIa-22 | R′ or $RCH_2$ | H | R—$CH_2$ |
| IIIa-23 | R′ or $RCH_2$ | RCO— | R—$CH_2$ |
| IIIa-24 | R′ or $RCH_2$ | R′ or $RCH_2$ | R—$CH_2$ |
| IIIa-25 | H | R′ or $RCH_2$ | R—$CH_2$ |
| IIIa-26 | RCO— | R′ or $RCH_2$ | R—$CH_2$ |

(20) A compound of (IIIa-27) wherein $R_1$, $R_3$ and $R_5$ of the formula (IIIa) are H, H and R', respectively, is synthesized as follows: AI-77-B is dissolved in a non-protonic polar solvent such as dimethylformamide or dimethylacetamide, 2.5- to 30-fold mols of R'W (wherein R' has the meaning as in formulas (I) and (II) and W is a halogen, preferably an iodine) is added to the solution, and the mixture is heated at 0° to 70° C.

(21) Other compounds wherein $R_5$ of the formula (IIIa) is R' can be synthesized in the manner described for method (20): the compounds (IIIa-28) to (IIIa-35) indicated in Table 10 below are synthesized from compounds (IIIa-10) to (IIIa-17) wherein $R_1$ and $R_3$ are the same as in the end compounds and $R_5$ is H.

TABLE 10

| Compound | $R_1$ | $R_3$ | $R_5$ | Starting material |
|---|---|---|---|---|
| IIIa-28 | H | RCO | R' | IIIa-10 |
| IIIa-29 | RCO | RCO | R' | IIIa-11 |
| IIIa-30 | RCO | H | R' | IIIa-12 |
| IIIa-31 | R' or RCH$_2$ | H | R' | IIIa-13 |
| IIIa-32 | R' or RCH$_2$ | RCO— | R' | IIIa-14 |
| IIIa-33 | R' or RCH$_2$ | R' or RCH$_2$ | R' | IIIa-15 |
| IIIa-34 | H | R' or RCH$_2$ | R' | IIIa-16 |
| IIIa-35 | RCO— | R' or RCH | R' | IIIa-17 |

Examples of the synthesis of compounds of formula (IVa) (wherein X of the formula (I) is O, Z combines with Y to provide a link for bonding C and C, $R_1$ and $R_3$ are the same as defined above):

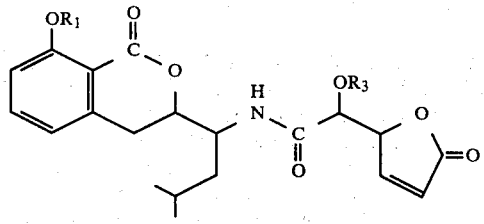

The preparation of AI-77-F [see method (22) below] and a compound of the formula (IV) wherein $R_1$ and $R_2$ are the same as defined above [see method (23) below] is described hereunder.

(22) AI-77-F is easily obtained by heating a mixture of AI-77-B with an alkyl halide in a polar solvent: AI-77-B is dissolved or suspended in a polar solvent such as N,N-dimethylformamide, N,N-dimethylacetamide, N-methylpyrrolidone, or hexamethylphosphorotriamide, and a great excess (i.e. 10 to 100 times the equivalent of AI-77-B) of an alkyl halide such as methyl iodide or ethyl iodide is added, and the mixture is heated overnight at a temperature between room and 70° C. The reaction can be monitored by high pressure liquid chromatography or thin layer chromatography. After the reaction, the reaction mixture is adsorbed on a macroreticulate resin, washed thoroughly, eluted with a hydrophilic organic solvent such as methanol or tetrahydrofuran, and then concentrated.

(23) A compound of (IVa-1) wherein $R_1$ and $R_3$ of the formula (IVa) and H and RCO—, respectively, is synthesized from AI-77-F by introducing RCO— at $R_3$ by means of the reaction of the method (2);

A compound of (IVa-2) wherein $R_1$ and $R_3$ of the formula (IVa) are each RCO— is synthesized from the compound (IVa-1) by acylating $R_1$ through the reaction of the method (3);

A compound of (IVa-3) wherein $R_1$ and $R_3$ of the formula (IVa) are RCO— and H, respectively, is synthesized from AI-77-F by acylating $R_1$ following the route of synthesis described for the method (4);

A compound of (IVa-4) wherein $R_1$ is R' or RCH$_2$ and $R_3$ is H is synthesized from AI-77-F by introducing R' or RCH$_2$ at $R_1$ following the reaction of the method (5);

A compound of (IVa-5) wherein $R_1$ is R' or RCH$_2$ and $R_3$ is RCO— is synthesized by reacting the compound (IVa-1) with a diazo compound following the reaction course of the method (6), thereby introducing R' or RCH$_2$ at $R_1$;

A compound of (IVa-6) wherein $R_1$ is R' or RCH$_2$ and $R_3$ is R' or RCH$_2$ is synthesized by subjecting the compound (IVa-4) to the reaction of the method (7) to introduce R' or RCH$_2$ at $R_3$;

A compound of (IVA-7) wherein $R_1$ is H and $R_3$ is R' or RCH$_2$ is synthesized by subjecting AI-77-F to the reaction of the method (8) to introduce R' or RCH$_2$ at $R_3$; and A compound of (IVa-8) wherein $R_1$ is RCO and $R_3$ is R' or RCH$_2$ is synthesized from the compound (IVa-7) by acylating $R_1$ through the reaction of the method (3).

(24) As shown in the formula (I), the compounds of this invention undergoes the formation or opening of a lactone ring between $T_1$ and $R_2$ or between $T_2$ and $R_4$. Such change in the state of the compound can easily occur.

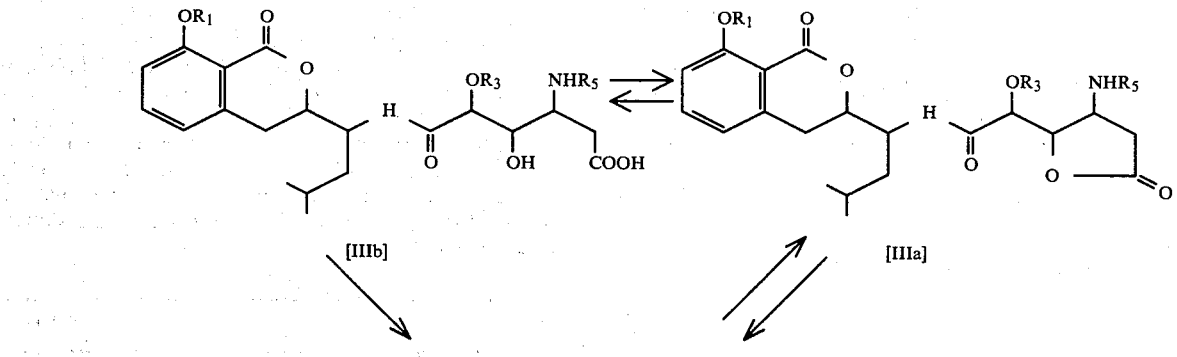

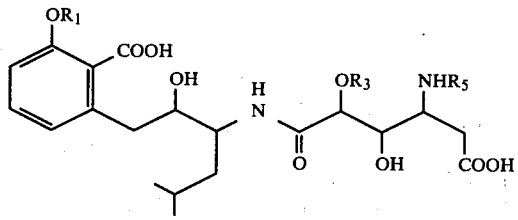

[IIIc]

The same change can occur in compounds wherein X is other than O as well as in compounds wherein Y combines with Z to provide a link for bonding C and C. The relation between the formulae (IIIa), (IIIb) and (IIIc) will be described below.

The three states of each compound are identified as follows: the compounds wherein $T_1$ and $R_2$ (also $T_2$ and $R_4$) of the formula (I) combine together to provide a link in a lactone ring are identified by a Roman numeral (for indicating a group of particular compounds) and A, B or F followed by a suffix (a); the compounds wherein $T_1$ and $R_2$ of the formula (I) combine together to provide a link in a lactone ring and $T_2$ is OH and $R_4$ is H are identified by the same notation except that the suffix is (b); and the compounds wherein $T_1$ and $T_2$ of the formula (I) are each OH and $R_2$ and $R_4$ are each H are identified by the same notation except that the suffix is (c).

The compounds of the formula (IIIb) are prepared by treating the compounds of the formula (IIIa) with a weak alkali to bring their pH to a range of from 7 to 9, followed by neutralization, and evaporation of the solvent to dryness.

The compounds of the formula (IIIc) are obtained as follows: a compound of the formula (IIIb) or (IIIa) is stirred in water or aqueous alcoholic solution at room temperature using a common alkaline reagent (e.g. sodium hydroxide) to control the pH to be in the range of from 9 to 13; after confirming the completion of the reaction by this high pressure liquid chromatography or IR spectrum analysis, the product is adsorbed on a macro-reticulate resin under cooling with the pH being controlled to 7 with a common acid such as hydrochloric acid, followed by thorough washing with water, elution with a hydrophilic organic solvent such as alcohols of $C_1$ to $C_4$ or tetrahydrofuran, and concentration. The compounds of the formula (IIIa) are obtained by dissolving the compounds of the formula (IIIb) or (IIIc) in a dried organic solvent such as alcohols or tetrahydrofuran, followed by distilling the solvent off under acidic conditions.

The production of the compounds of the formula (I) wherein X is $NR_6$ is described in the following two paragraphs [methods (25) and (26)].

(25) A compound of the formula (I) wherein $R_1$, $R_3$ and $R_5$ are each H and X is NR can be synthesized from AI-77-A by reacting it with a great excess (1.5- to 100-fold mols) of amine ($RNH_2$) as follows: if the amine is liquid, it is also used as a solvent, and if it is solid, the reaction mixture is dissolved in a minimum amount of a non-protonic polar solvent; the reaction mixture is then heated to 40° to 100° C. (in vacuum, if necessary) for a period of 10 minutes to 5 hours. By so doing, compounds of (Vb-1) other than AI-77-A are produced.

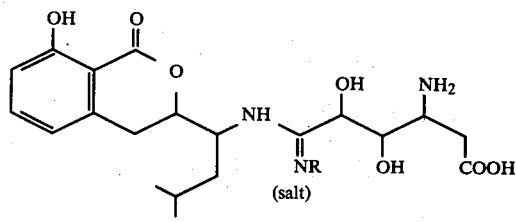

(26) Compounds of (Va-1) to (Va-27) can be synthesized from AI-77-Ba wherein X is O as well as from (IIIa-10) through (IIIa-35) by the following reaction: a corresponding starting material is dissolved or dispersed in dichloromethane, 3- to 6-fold mols of triethyloxonium tetrafluoroborate in dichloromethane is added to the solution or dispersion, and the mixture is heated at room temperature for a period of 1 to 24 hours. After distilling dichloromethane off, the residual iminoether is reacted with 1.5- to 100-times mols of ammonia or primary amine ($NH_2R$) by stirring the mixture at room temperature for 2 to 5 days in the presence of a solvent in a minimum required amount to dissolve both amines and iminoether. Instead of using the solvent, primary amine may be directly added to the reaction system. As a result, the corresponding compounds (Va-1) to (Va-27) are formed. A preferred solvent is a non-protonic polar solvent, and acohols may be used depending on the case.

In a like manner, compounds of (Vb-1) through (Vb-27) can be synthesized from AI-77-B and compounds of (IIIb-10) through (IIIb-35), and compounds of (Vc-1) through (Vc-27) from AI-77-Bc (AI-77-G) and from compounds of (IIIc-10) through (IIIc-35). In an identical manner, compounds of (VIa-1) through (VIa-9) can be synthesized from AI-77-F and from compounds of (IVa-1) through (IVa-8), compounds of (VIb-1) through (VIb-9) from AI-77-Fb and from compounds of (IVb-1) through (IVb-8), and compounds of (VIc-1) through (VIc-9) from AI-77-Fc and from compounds of (IVc-1) through (IVc-8). These compounds are shown in Table 11 below.

TABLE 11

| Compound | $R_1$ | $R_3$ | $R_5$ | X | Starting material |
|---|---|---|---|---|---|
| V-1 | H | H | H | $NR_6$ | B |
| V-2 | H | RCO | H | $NR_6$ | III-10 |
| V-3 | RCO | RCO | H | $NR_6$ | III-11 |
| V-4 | RCO | H | H | $NR_6$ | III-12 |
| V-5 | R' or $RCH_2$ | H | H | $NR_6$ | III-13 |
| V-6 | R' or $RCH_2$ | RCO | H | $NR_6$ | III-14 |
| V-7 | R' or $RCH_2$ | R' or $RCH_2$ | H | $NR_6$ | III-15 |
| V-8 | H | R' or $RCH_2$ | H | $NR_6$ | III-16 |
| V-9 | RCO | R' or $RCH_2$ | H | $NR_6$ | III-17 |
| V-10 | H | H | $RCH_2$ | $NR_6$ | III-18 |

TABLE 11-continued

| Compound | R₁ | R₃ | R₅ | X | Starting material |
|---|---|---|---|---|---|
| V-11 | H | RCO | RCH₂ | NR₆ | III-19 |
| V-12 | RCO | RCO | RCH₂ | NR₆ | III-20 |
| V-13 | RCO | H | RCH₂ | NR₆ | III-21 |
| V-14 | R' or RCH₂ | H | RCH₂ | NR₆ | III-22 |
| V-15 | R' or RCH₂ | RCO | RCH₂ | NR₆ | III-23 |
| V-16 | R' or RCH₂ | R' or RCH₂ | RCH₂ | NR₆ | III-24 |
| V-17 | H | R' or RCH₂ | RCH₂ | NR₆ | III-25 |
| V-18 | RCO | R' or RCH₂ | RCH₂ | NR₆ | III-26 |
| V-19 | H | H | R' | NR₆ | III-27 |
| V-20 | H | RCO | R' | NR₆ | III-28 |
| V-21 | RCO | RCO | R' | NR₆ | III-29 |
| V-22 | RCO | H | R' | NR₆ | III-30 |
| V-23 | R' or RCH₂ | H | R' | NR₆ | III-31 |
| V-24 | R' or RCH₂ | RCO | R' | NR₆ | III-32 |
| V-25 | R' or RCH₂ | R' or RCH₂ | R' | NR₆ | III-33 |
| V-26 | H | R' or RCH₂ | R' | NR₆ | III-34 |
| V-27 | RCO | R' or RCH₂ | R' | NR₆ | III-35 |
| VI-1 | H | H | — | NR₆ | F |
| VI-2 | H | RCO | — | NR₆ | IV-1 |
| VI-3 | RCO | RCO | — | NR₆ | IV-2 |
| VI-4 | RCO | H | — | NR₆ | IV-3 |
| VI-5 | R' or RCH₂ | H | — | NR₆ | IV-4 |
| VI-6 | R' or RCH₂ | RCO | — | NR₆ | IV-5 |
| VI-7 | R' or RCH₂ | R' or RCH₂ | — | NR₆ | IV-6 |
| VI-8 | H | R' or RCH₂ | — | NR₆ | IV-7 |
| VI-9 | RCO | R' or RCH₂ | — | NR₆ | IV-8 |

In Table 11, the Roman numerals III, IV; V and VI are each a generic symbol for the three states of the respective formulae, i.e. (IIIa), (IIIb) and (IIIc); (IVa), (IVb) and (IVc); (Va) (Vb) and (Vc); and (VIa), (VIb) and (VIc). The symbol R₆ is equivalent to R₆ in appending Claim 1 and represents H or R.

(27) The final reaction products of the methods (1) through (26) may be purified by the following procedures; the final liquid reaction product is concentrated, dissolved in dried methanol or dried ethanol through which hydrogen chloride gas has been passed, and the solution is concentrated to dryness. Repeating this procedure several times gives a lactone compound of the formula (IIIa), which is then adsorbed on a column of a macro-reticulate resin, such as Amberlite XAD-2 (trademark of Rohm & Hass Co), and chromatographed using an eluting solvent comprising water or a hydrophilic organic solvent which is preferably methanol, ethanol, propanol, isopropanol or tetrahydrofuran, or a mixture thereof with water.

The compounds synthesized by the methods (25) and (26) and the compounds converted to each other by the method (24) can be purified from the liquid reaction product by adsorbing them on a column of a macro-reticulate resin, say, XAD-2, and performing chromatography using an eluting solvent comprising an alcohol of $C_1$ to $C_4$ or tetrahydrofuran or a mixture of such organic solvent with water.

The synthesis of the compounds of the formula (II) is described hereunder. The method of synthesizing a compound of the formula (VII) below (wherein $R_1$, $R_3$, $R_5$ and $R_7$ are the same as defined above) is described first [method (28)]. Then, the method of synthesizing a compound of the formula (VIII) below (wherein $R_1$, $R_3$ and $R_7$ are the same as defined above) is described [method (29)].

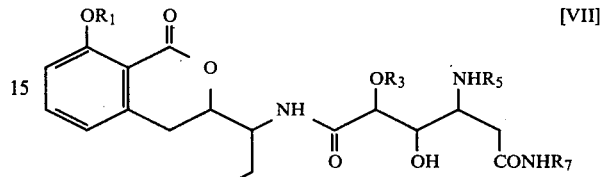

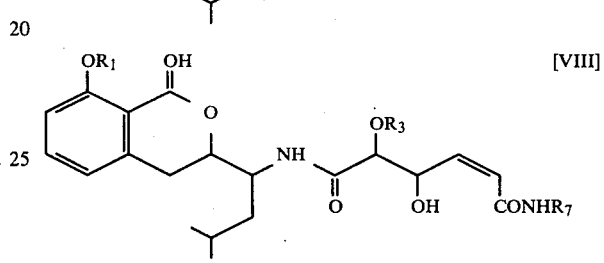

(28) A compound of the formula (IIIa) is reacted with amonia or dried primary amine (NH₂R₃). To react 1.5- to 100-fold mols of free amine or 2.5-to 100-fold mols of an amine salt, a liquid amine is used as a solvent or a gaseous or solid amine is dissolved in a non-protonic solvent (or an alcohol if the case requires) that dissolves both the compound and amine. By heating the reaction mixture at 0° to 30° C. under stirring for a period of 1 to 72 hours, a compound of the formula (VII) wherein the amine has reactes with a 5-membered lactone is produced.

(29) A compound of the formula (VIII) is prepared from a compound of (IVa) under the same reaction conditions as in the method (28) using a non-protonic polar solvent such as dimethylformamide or dimethylsulfoxide.

Alternatively, a compound of the formula (VIII) can be synthesized from a compound of the formula (IV) or (V) by hydrolyzing a six-membered lactone in a weak alkaline solution.

The compounds produced by the methods (28) and (29) as well as the materials from which they are derived are set forth in Table 12 below.

TABLE 12

| Compound | R₁ | R₂ | R₄ | R₃ | Starting material |
|---|---|---|---|---|---|
| VII-1 | H | H | H | H or R' | AI-77-Ba |
| VII-2 | H | RCO | H | H or R' | IIIa-10 |
| VII-3 | RCO | RCO | H | H or R' | IIIa-11 |
| VII-4 | RCO | H | H | H or R' | IIIa-12 |
| VII-5 | R' or RCH₂ | H | H | H or R' | IIIa-13 |
| VII-6 | R' or RCH₂ | RCO | H | H or R' | IIIa-14 |
| VII-7 | R' or RCH₂ | R' or RCH₂ | H | H or R' | IIIa-15 |
| VII-8 | H | R' or RCH₂ | H | H or R' | IIIa-16 |
| VII-9 | RCO | R' or RCH₂ | H | H or R' | IIIa-17 |
| VII-10 | H | H | RCH₂ | H or R' | IIIa-18 |
| VII-11 | H | RCO | RCH₂ | H or R' | IIIa-19 |
| VII-12 | RCO | RCO | RCH₂ | H or R' | IIIa-20 |
| VII-13 | RCO | H | RCH₂ | H or R' | IIIa-21 |
| VII-14 | R' or RCH₂ | H | RCH₂ | H or R' | IIIa-22 |

TABLE 12-continued

| Compound | R₁ | R₂ | R₄ | R₃ | Starting material |
|---|---|---|---|---|---|
| VII-15 | R' or RCH₂ | RCO | RCH₂ | H or R' | IIIa-23 |
| VII-16 | R' or RCH₂ | R' or RCH₂ | RCH₂ | H or R' | IIIa-24 |
| VII-17 | H | R' or RCH₂ | RCH₂ | H or R' | IIIa-25 |
| VII-18 | RCO | R' or RCH₂ | RCH₂ | H or R' | IIIa-26 |
| VII-19 | H | H | R' | H or R' | IIIa-27 |
| VII-20 | H | RCO | R' | H or R' | IIIa-28 |
| VII-21 | RCO | RCO | R' | H or R' | IIIa-29 |
| VII-22 | RCO | H | R' | H or R' | IIIa-30 |
| VII-23 | R' or RCH₂ | H | R' | H or R' | IIIa-31 |
| VII-24 | R' or RCH₂ | RCO | R' | H or R' | IIIa-32 |
| VII-25 | R' or RCH₂ | R' or RCH₂ | R' | H or R' | IIIa-33 |
| VII-26 | H | R' or RCH₂ | R' | H or R' | IIIa-34 |
| VII-27 | RCO | R' or RCH₂ | R' | H or R' | IIIa-35 |
| VII-28 | H | H | RCO | H or R' | IIIa-1 |
| VII-29 | H | RCO | RCO | H or R' | IIIa-2 |
| VII-30 | RCO | RCO | RCO | H or R' | IIIa-3 |
| VII-31 | RCO | H | RCO | H or R' | IIIa-4 |
| VII-32 | R' or RCH₂ | H | RCO | H or R' | IIIa-5 |
| VII-33 | R' or RCH₂ | RCO | RCO | H or R' | IIIa-6 |
| VII-34 | R' or RCH₂ | R' or RCH₂ | RCO | H or R' | IIIa-7 |
| VII-35 | H | R' or RCH₂ | RCO | H or R' | IIIa-8 |
| VII-36 | RCO | R' or RCH₂ | RCO | H or R' | IIIa-9 |
| VIII-1 | H | H | — | H or R' | AI-77-F |
| VIII-2 | H | RCO | — | H or R' | IVa-1 |
| VIII-3 | RCO | RCO | — | H or R' | IVa-2 |
| VIII-4 | RCO | H | — | H or R' | IVa-3 |
| VIII-5 | R' or RCH₂ | H | — | H or R' | IVa-4 |
| VIII-6 | R' or RCH₂ | RCO | — | H or R' | IVa-5 |
| VIII-7 | R' or RCH₂ | R' or RCH₂ | — | H or R' | IVa-6 |
| VIII-8 | H | R' or RCH₂ | — | H or R' | IVa-7 |
| VIII-9 | RCO | R' or RCH₂ | — | H or R' | IVa-8 |

Typical examples of the compounds synthesized by the methods (1) through (29) are given in Table 13. As mentioned before, these compounds exhibit an appreciable pharmaceutical effect. Tables 13, 14 and 15 show the effect of these compounds to inhibit the occurrence of ulcer and edema. The anti-ulcer and anti-edema activity of the compounds was evaluated in efficacy tests described below. The first two symbols that appear in each of the compound names in Tables 13 and 15 represent the compounds synthesized in the methods (1) through (29); for example, IIIa-1 of a compound IIIa-1-1 represent the compound (IIIa-1).

Test 1. Anti-ulcer test

Male Wistar rats weighing about 150 g on average were not fed for 24 hours before the test. Then a solution or suspension of a predetermined concentration of the test compound in physiological saline was administered to them intraperitoneally. One hour after the administration, each rat was restrained in a net cage and submerged in a water both (21° C.) from the tail to xiphistrenun for 6 hours. Test animals were then killed (by dislocation of the cervical vertebrae), the stomach was removed and incised along the curvatura ventriculi major, and the inside wall of the stomach was pathologically examined under microscopic observation. Rats in which the occurrence of an ulceration was substantially not observed were rated O, while others were rated 0.5, 1, 2 or 3, depending on the severity of the ulcer development. The percent inhibition of ulcer was calculated by the following formula:

$$\text{percent ulcer inhibition} = 100 - \frac{\text{total of the ratings of test animals}}{\text{total of the ratings of controls}} \times 100$$

Table 13 shows the percent ulcer inhibition for each compound when it was administered intraperitoneally in a dose of 50 mg/kg.

Test 2. Anti-edema test

Male Wistar rats weighing about 150 g on average were starved overnight prior to the test. They were than orally administered 100 mg/kg of the test compound. One hour later, the pad of a hindfoot of the animal was injected with 1 mg of carrageenan. The volume of the foot was measured both before the injection of carrageenan and three hours after the injection. The percent edema inhibition of the test compound was calculated from the ratio of the increase in the volume of the affected foot of the test animals to the increase in the volume of the affected foot of the controls. The results are shown in Table 15.

Compounds AI-77-A and AI-77-B of the formula (I) as well as their derivatives are preferred in view of their high anti-ulcer activity. Particularly preferred compounds are AI-77-A, (Vb-1), (Vb-5), (Vb-10), (Vb-14), (Vb-19) and (Vb-23), as well as AI-77-B, (IIIa-13), (IIIa-18), (IIIa-22), (IIIa-27) and (IIIa-31), and compounds of the formulae (VII-1), (VII-10) and (VII-19).

Compounds of (IIIa-18), (IIIa-22) and (IIIa-27) exhibit particularly strong anti-edema effect.

TABLE 13

| Compound No. | $R_1$ | $R_3$ | $R_5$ | % Inhibition of Ulcer 50 mg/kg i.p. (%) |
|---|---|---|---|---|
| IIIa-1-1 | H | H | $CH_3CO$ | 66 |
| IIIa-1-2 | H | H | $CH_3CH_2CO$ | 66 |
| IIIa-1-3 | H | H | $CH_3(CH_2)_2CO$ | 66 |
| IIIa-1-4 | H | H | $(CH_3)_2CHCO$ | 66 |
| IIIa-1-5 | H | H | $(CH_3)_2CHCH_2CO$ | 66 |
| IIIa-1-6 | H | H | $CH_3(CH_2)_3CO$ | 66 |
| IIIa-1-7 | H | H | $CH_3(CH_2)_4CO$ | 66 |
| IIIa-1-8 | H | H | $CH_3(CH_2)_5CO$ | 66 |
| IIIa-1-9 | H | H | $CH_3(CH_2)_6CO$ | 66 |
| IIIa-1-10 | H | H | $CH_3(CH_2)_{10}CO$ | 44 |
| IIIa-1-11 | H | H | $CH_3(CH_2)_{16}CO$ | 44 |
| IIIa-1-12 | H | H | $CCl_3CO$ | 66 |
| IIIa-1-13 | H | H | $HC(CH_2)_7CH_3$<br>$\|\|$<br>$HC(CH_2)_7CO$ | 44 |
| IIIa-1-14 | H | H | Ph-CO | 56 |
| IIIa-1-15 | H | H | naphthyl-CO | 44 |
| IIIa-1-16 | H | H | adamantyl-CO | 56 |
| IIIa-1-17 | H | H | 2-(N-acetyl)phenyl-CO | 66 |
| IIIa-1-18 | H | H | cyclopropyl-CO | 66 |

TABLE 13-continued
| Compound No. | $R_1$ | $R_3$ | $R_5$ | % Inhibition of Ulcer 50 mg/kg i.p. (%) |
|---|---|---|---|---|
| IIIa-1-19 | H | H | 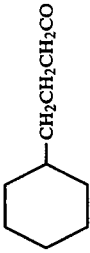 cyclohexyl-CH$_2$CH$_2$CH$_2$CO | 66 |
| IIIa-1-20 | H | H | 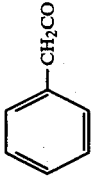 phenyl-CH$_2$CO | 66 |
| IIIa-1-21 | H | H | 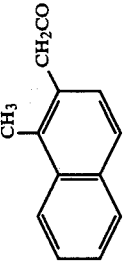 1-CH$_3$, 2-CH$_2$CO naphthyl | 56 |
| IIIa-1-22 | H | H | 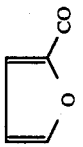 furyl-CO | 66 |
| IIIa-1-23 | H | H | 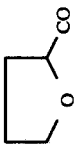 tetrahydrofuryl-CO | 66 |
| IIIa-1-24 | H | H | 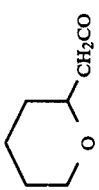 tetrahydropyranyl-CH$_2$CO | 66 |
| IIIa-1-25 | H | H | 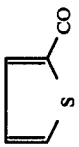 thienyl-CO | 66 |
| IIIa-1-26 | H | H |  thienyl-CH$_2$CH$_2$CH$_2$CO | 66 |

TABLE 13-continued
| Compound No. | $R_1$ | $R_3$ | $R_5$ | % Inhibition of Ulcer 50 mg/kg i.p. (%) |
|---|---|---|---|---|
| IIIa-1-27 | H | H | 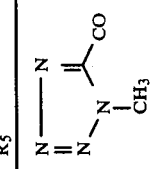 | 66 |
| IIIa-1-28 | H | H | 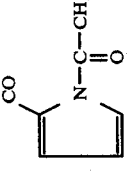 | 66 |
| IIIa-1-29 | H | H | 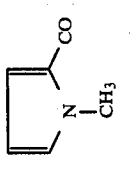 | 66 |
| IIIa-1-30 | H | H | 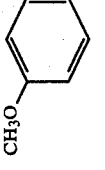 | 56 |
| IIIa-1-31 | H | H | $BrCH_2CH_2CH_2CO$ | 66 |
| IIIa-1-32 | H | H | $CH_3CH_2C{-}CO$ 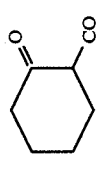 | 66 |
| IIIa-1-33 | H | H | 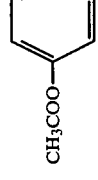 | 66 |
| IIIa-1-34 | H | H |  | 66 |

TABLE 13-continued

| Compound No. | $R_1$ | $R_3$ | $R_5$ | % Inhibition of Ulcer 50 mg/kg i.p. (%) |
|---|---|---|---|---|
| IIIa-1-35 | H | H | 4-HO-C$_6$H$_4$-CO- | 66 |
| IIIa-1-36 | H | H | CH$_2$COOCH$_2$CH$_3$ / CH$_2$CO | 66 |
| IIIa-1-37 | H | H | CH$_2$COOH / CH$_2$CO | 66 |
| IIIa-1-38 | H | H | CH$_2$COOH / CH$_2$CO | 66 |
| IIIa-1-39 | H | H | 4-CH$_3$-C$_6$H$_4$-CO- | 56 |
| IIIa-1-40 | H | H | (CH$_3$)$_2$CHCH$_2$CH$_2$-C$_6$H$_4$-CO- | 66 |
| IIIa-1-41 | H | H | 4-CH$_3$O-C$_6$H$_4$-CO- | 56 |
| IIIa-1-42 | H | H | (CH$_3$)$_2$CHCH$_2$CH$_2$O-C$_6$H$_4$-CO- | 66 |
| IIIa-1-42 | H | H | CH$_3$OCHCH$_2$CO / CH$_3$ | 66 |
| IIIa-1-43 | H | H | CH$_3$(CH$_2$)$_4$O-CHCH$_2$CO / CH$_3$ | 66 |

TABLE 13-continued

| Compound No. | $R_1$ | $R_3$ | $R_5$ | % Inhibition of Ulcer 50 mg/kg i.p. (%) |
|---|---|---|---|---|
| IIIa-1-44 | H | H | CH$_3$SCH$_2$CO | 66 |
| IIIa-1-45 | H | H | CH$_3$(CH$_2$)$_3$CH$_2$SCH$_2$CO | 66 |
| IIIa-1-46 | H | H | CH$_3$S—C$_6$H$_4$—CO | 66 |
| IIIa-1-47 | H | H | CH$_3$(CH$_2$)$_3$CH$_2$S—C$_6$H$_4$—CO | 56 |
| IIIa-1-48 | H | H | CH$_3$COO—CH(CH$_3$)—CH$_2$CO | 66 |
| IIIa-1-49 | H | H | CH$_3$(CH$_2$)$_3$CH$_2$COO—CH(CH$_3$)—CH$_2$CO | 56 |
| IIIa-1-50 | H | H | CH$_3$OOC—C$_6$H$_4$—CO | 66 |
| IIIa-1-51 | H | H | CH$_3$(CH$_2$)$_3$CH$_2$OOC—C$_6$H$_4$—CO | 44 |
| IIIa-1-52 | H | H | CH≡C—CO | 66 |
| IIIa-1-53 | H | H | (CH$_3$)$_2$CH—CH$_2$CH$_2$—C$_6$H$_4$—CH(CH$_3$)—CHO | 56 |

TABLE 13-continued

| Compound No. | $R_1$ | $R_3$ | $R_5$ | % Inhibition of Ulcer 50 mg/kg i.p. (%) |
|---|---|---|---|---|
| IIIa-1-54 | H | H | $CH_3\text{-}C(H)=C(H)\text{-}CO$ | 66 |
| IIIa-1-55 | H | H | $CH_3\text{-}C(CH_3)=CHCH_2\text{-}C(CH_3)=C(H)\text{-}CO$ | 66 |
| IIIa-1-56 | H | H | $CH_3CH_2CH(CH_3)CH_2CH_2CH_2CO$ | 66 |
| IIIa-1-57 | H | H | 2-furyl-CH=CH-CO | 56 |
| IIIa-1-58 | H | H | 3-pyridyl-CH$_2$CO | 66 |
| IIIa-1-59 | H | H | 3,4-dihydro-2H-pyran-2-CO | 66 |
| IIIa-1-60 | H | H | 2-HOOC-4-HOOC-furan-5-CO (furan-2,4-dicarboxy with 5-CO) | 66 |
| IIIa-1-61 | H | H | 2-COOH-4-CH$_3$-cyclohexyl-CO | 66 |

TABLE 13-continued

| Compound No. | R₁ | R₃ | R₅ | % Inhibition of Ulcer 50.mg/kg i.p. (%) |
|---|---|---|---|---|
| IIIa-1-62 | H | H | cycloheptyl-CO | 66 |
| IIIa-1-63 | H | H | cyclopentyl-CH₂CH₂CO | 66 |
| IIIa-1-64 | H | H | 2-naphthyl-CH₂CO | 56 |
| IIIa-1-65 | H | H | 4-CH₃-C₆H₄-CH₂CO | 66 |
| IIIa-1-66 | H | H | (CH₃)₂CHCH₂CH₂CH₂CH(CH₃)CH₂CH₂CH₂CH₂CO | 66 |
| IIIa-1-67 | H | H | (CH₃)₂C=CHCH₂CH₂C(CH₃)=CHCH₂CH₂C(CH₃)=CHCH₂CO (with H's) | 66 |
| IIIa-1-68 | H | H | 4-(CH₃OOC)-cyclohexyl-CO | 66 |
| IIIa-1-69 | H | H | 4-((CH₃)₂CH)-C₆H₄-CO | 66 |

TABLE 13-continued

| Compound No. | R₁ | R₃ | R₅ | % Inhibition of Ulcer 50 mg/kg i.p. (%) |
|---|---|---|---|---|
| IIIa-1-70 | H | H | (2,4-dimethyl-7-ethylazulen-1-yl)CO– | 56 |
| IIIa-1-71 | H | H | (norbornenyl)CO– | 66 |
| IIIa-1-72 | H | H | (camphor-like bicyclic)CO– | 66 |
| IIIa-1-73 | H | H | trans-4-methoxycyclohexyl-CO– | 66 |
| IIIa-1-74 | H | H | trans-4-(methoxycarbonyl)cyclohexyl-CO– | 66 |
| IIIa-1-75 | H | H | (1,2,3-triazol-1-yl)CH₂CO– | 66 |
| IIIa-1-76 | H | H | 4-(n-pentyl)benzoyl– | 66 |

TABLE 13-continued

| Compound No. | $R_1$ | $R_3$ | $R_5$ | % Inhibition of Ulcer 50 mg/kg i.p. (%) |
|---|---|---|---|---|
| IIIa-1-77 | H | H | $CH_3CH_2CH_2CH=CH$—C$_6$H$_4$—CO (para) | 66 |
| IIIa-1-78 | H | H | $HOCH_2(CH_2)_8CO$ | 66 |
| IIIa-1-79 | H | H | cyclopropyl-$CH_2CO$ | 66 |
| IIIa-1-80 | H | H | $Br(CH_3)C=C(CH_3)CO$ | 66 |
| IIIa-1-81 | H | H | $(CH_3)_2C=CHCO$ | 66 |
| IIIa-1-82 | H | H | $CH_3$—C(SCH$_3$)(CH$_3$)—$CH_2CO$ | 66 |
| IIIa-1-83 | H | H | $CH_3$—C(OCH$_3$)(CH$_3$)—$CH_2CO$ | 66 |
| IIIa-2-1 | H | $CCl_3CO$ | $CCl_3CO$ | 44 |
| IIIa-2-2 | H | $CH_3CO$ | $CH_3CO$ | 44 |
| IIIa-2-3 | H | $CH_3CO$ | $(CH_3)_2CHCH_2CO$ | 44 |
| IIIa-2-4 | H | $CH_3CO$ | $CH_3(CH_2)_{16}CO$ | 33 |
| IIIa-2-5 | H | $CH_3CO$ | $HC(CH_2)_7CH_3$=$HC(CH_2)_7CO$ | 33 |
| IIIa-2-6 | H | $CH_3CO$ | tetrahydrofuran-2-CO | 44 |
| IIIa-2-7 | H | $CH_3CO$ | $(CH_3)_2CHCH_2CO$ | 44 |

TABLE 13-continued

| Compound No. | $R_1$ | $R_3$ | $R_5$ | % Inhibition of Ulcer 50 mg/kg i.p. (%) |
|---|---|---|---|---|
| IIIa-2-8 | H | $CH_3CO$ | 4-$CH_3$-C$_6$H$_4$-CO | 44 |
| IIIa-2-9 | H | $CH_3CO$ | $CH_3$-CH(CH$_3$)-CH$_2$CH$_2$O-C$_6$H$_4$-4-CO | 33 |
| IIIa-2-10 | H | $CH_3CH_2CO$ | $CH_3CO$ | 44 |
| IIIa-2-11 | H | $CH_3CH_2CH_2CO$ | $CH_3CH_2CH_2CO$ | 33 |
| IIIa-2-12 | H | $CH_3CH_2CO$ | $CCl_3CO$ | 44 |
| IIIa-3-1 | $CH_3CO$ | $CH_3CO$ | $CH_3CO$ | 33 |
| IIIa-3-2 | $(CH_3)_2CHCO$ | $CH_3CH_2CO$ | $CH_3CO$ | 33 |
| IIIa-3-3 | $CH_3CO$ | $CH_3CO$ | $(CH_3)_2CHCH_2CO$ | 33 |
| IIIa-3-4 | $CH_3CO$ | $CH_3CO$ | $CH_3(CH_2)_{16}CO$ | 22 |
| IIIa-3-5 | $CH_3CO$ | $CH_3CO$ | $HC(CH_2)_7CH_3$ =  $HC(CH_2)_7CO$ | 22 |
| IIIa-3-6 | $CH_3CO$ | $CH_3CO$ | tetrahydrofuran-2-CO | 33 |
| IIIa-3-7 | $CH_3CO$ | $CH_3CO$ | $CH_3O$-CH(CH$_3$)-CO | 33 |
| IIIa-3-8 | $CH_3CO$ | $CH_3CO$ | 4-$CH_3$-C$_6$H$_4$-CO | 33 |
| IIIa-3-9 | $CH_3CO$ | $CH_3CO$ | $CH_3$-CH(CH$_3$)-CH$_2$CH$_2$O-C$_6$H$_4$-4-CO | 22 |
| IIIa-3-10 | $CH_3CO$ | $CCl_3CO$ | $CCl_3CO$ | 33 |
| IIIa-4-1 | $CH_3CO$ | H | $CH_3CO$ | 44 |

TABLE 13-continued

| Compound No. | R₁ | R₃ | R₅ | % Inhibition of Ulcer 50 mg/kg i.p. (%) |
|---|---|---|---|---|
| IIIa-4-2 | CH₃CO | H | (CH₃)₂CHCO | 44 |
| IIIa-4-3 | CH₃CO | H | CH₃(CH₂)₁₆CO | 33 |
| IIIa-4-4 | CH₃CO | H | HC(CH₂)₇CH₃<br>‖<br>HC(CH₂)₇CO | 33 |
| IIIa-4-5 | CH₃CO | H | (tetrahydrofuran-2-yl)CO | 33 |
| IIIa-4-6 | CH₃CO | H | CH₃O—CH(CH₃)—CH₂CO | 44 |
| IIIa-4-7 | CH₃CO | H | 4-CH₃-C₆H₄-CO | 33 |
| IIIa-4-8 | CH₃CO | H | 4-[CH(CH₃)₂-CHCH₂O]-C₆H₄-CO | 33 |
| IIIa-4-9 | CCl₃CO | H | CCl₃CO | 33 |
| IIIa-5-1 | CH₃CH₂ | H | CH₃CO | 44 |
| IIIa-5-2 | CH₃(CH₂)₂CH₂ | H | (CH₃)₂CHCH₂CO | 44 |
| IIIa-5-3 | (CH₃)₂CHCH₂ | H | CH₃CO | 44 |
| IIIa-5-4 | CH₃ | H | (CH₃)₂CHCO | 33 |
| IIIa-5-5 | CH₃(CH₂)₅CH₂ | H | CH₃CO | 44 |
| IIIa-5-6 | CH₃ | H | CH₃(CH₂)₁₆CO | 33 |
| IIIa-5-7 | | H | CCl₃CO | 44 |
| IIIa-5-8 | HC(CH₂)₇CH₃<br>‖<br>HC(CH₂)₇CH₂ | H | CH₃CO | 33 |
| IIIa-5-9 | CH₃(CH₂)₁₀CH₂ | H | CH₃CO | 33 |
| IIIa-5-10 | (CH₃)₂CHCH₂ | H | CH₃CO | 44 |
| IIIa-5-11 | CH₃(CH₂)₆CH₂ | H | CH₃CO | 44 |
| IIIa-5-12 | CH₃(CH₂)₁₆CH₂ | H | CH₃(CH₂)₅CO | 33 |
| IIIa-5-13 | CH₃CH₂ | H | CCl₃CO | 33 |

TABLE 13-continued

| Compound No. | $R_1$ | $R_3$ | $R_5$ | % Inhibition of Ulcer 50 mg/kg i.p. (%) |
|---|---|---|---|---|
| IIIa-5-14 | $CH_3CH_2$ | H | $\overset{HC(CH_2)_7CH_3}{\underset{HC(CH_2)_7CH_2CO}{\|\|}}$ | 33 |
| IIIa-5-15 | $CH_3CH_2$ | H | adamantyl-CO | 33 |
| IIIa-5-16 | $CH_3CH_2$ | H | phenyl-CO | 33 |
| IIIa-5-17 | $CH_3CH_2$ | H | naphthyl-CO | 33 |
| IIIa-5-18 | $CH_3CH_2$ | H | cyclopropyl-CO | 44 |
| IIIa-5-19 | $CH_3CH_2$ | H | cyclohexyl-$CH_2CH_2CH_2CO$ | 44 |
| IIIa-5-20 | $CH_3CH_2$ | H | phenyl-$CH_2CO$ | 44 |
| IIIa-5-21 | $CH_3CH_2$ | H | 1-methyl-2-($CH_2CO$)-naphthyl | 33 |

TABLE 13-continued
| Compound No. | $R_1$ | $R_3$ | $R_5$ | % Inhibition of Ulcer 50 mg/kg i.p. (%) |
|---|---|---|---|---|
| IIIa-5-22 | $CH_3CH_2$ | H |  | 44 |
| IIIa-5-23 | $CH_3CH_2$ | H |  | 44 |
| IIIa-5-24 | $CH_3CH_2$ | H | 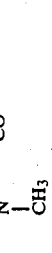 | 44 |
| IIIa-5-25 | $CH_3CH_2$ | H |  | 44 |
| IIIa-5-26 | $CH_3CH_2$ | H |  | 33 |
| IIIa-5-27 | $CH_3CH_2$ | H |  | 44 |
| IIIa-5-28 | $CH_3CH_2$ | H | 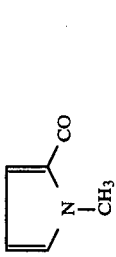 | 44 |
| IIIa-5-29 | $CH_3CH_2$ | H |  | 33 |

TABLE 13-continued

| Compound No. | $R_1$ | $R_3$ | $R_5$ | % Inhibition of Ulcer 50 mg/kg i.p. (%) |
|---|---|---|---|---|
| IIIa-5-30 | $CH_3CH_2$ | H | 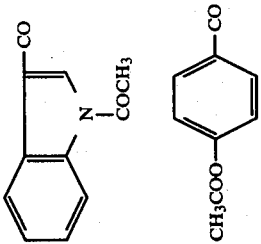 6-methoxyquinoline-3-CO— with $CH_3O$ substituent | 33 |
| IIIa-5-31 | $CH_3CH_2$ | H | $BrCH_2CH_2CH_2CO$ | 44 |
| IIIa-5-32 | $CH_3CH_2$ | H | $CH_3CH_2C(O)-CO$ | 44 |
| IIIa-5-33 | $CH_3CH_2$ | H |  2-oxocyclohexyl-CO | 44 |
| IIIa-5-34 | $CH_3CH_2$ | H | 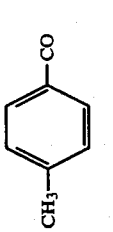 1-acetylindole-3-CO | 33 |
| IIIa-5-35 | $CH_3CH_2$ | H |  4-acetoxybenzoyl ($CH_3COO$—C$_6$H$_4$—CO) | 44 |
| IIIa-5-36 | $CH_3CH_2$ | H | $CH_3CH_2OOCCH_2$—$CH_2CO$ | 44 |
| IIIa-5-37 | $CH_3CH_2$ | H |  4-methylbenzoyl ($CH_3$—C$_6$H$_4$—CO) | 44 |
| IIIa-5-38 | $CH_3CH_2$ | H |  4-isobutylbenzoyl-type group | 33 |

TABLE 13-continued

| Compound No. | $R_1$ | $R_3$ | $R_5$ | % Inhibition of Ulcer 50 mg/kg i.p. (%) |
|---|---|---|---|---|
| IIIa-5-39 | $CH_3CH_2$ | H | $CH_3O$-C$_6$H$_4$-CO- | 44 |
| IIIa-5-40 | $CH_3CH_2$ | H | $(CH_3)_2CHCH_2CH_2O$-C$_6$H$_4$-CO- | 33 |
| IIIa-5-41 | $CH_3CH_2$ | H | $CH_3OCH(CH_3)CHCH_2CO$- | 33 |
| IIIa-5-42 | $CH_3CH_2$ | H | $CH_3(CH_2)_4OCH(CH_3)CHCH_2CO$- | 33 |
| IIIa-5-43 | $CH_3CH_2$ | H | $CH_3SCH_2CO$- | 44 |
| IIIa-5-44 | $CH_3CH_2$ | H | $CH_3(CH_2)_3SCH_2CO$- | 33 |
| IIIa-5-45 | $CH_3CH_2$ | H | $CH_3S$-C$_6$H$_4$-CO- | 33 |
| IIIa-5-46 | $CH_3CH_2$ | H | $CH_3(CH_2)_3CH_2S$-C$_6$H$_4$-CO- | 33 |
| IIIa-5-47 | $CH_3CH_2$ | H | $CH_3COOCH(CH_3)CHCH_2CO$- | 33 |
| IIIa-5-48 | $CH_3CH_2$ | H | $CH_3(CH_2)_3CH_2COOCH(CH_3)CHCH_2CO$- | 33 |

TABLE 13-continued

| Compound No. | R₁ | R₃ | R₅ | % Inhibition of Ulcer 50 mg/kg i.p. (%) |
|---|---|---|---|---|
| IIIa-5-49 | $CH_3CH_2$ | H | $CH_3OOC$-C₆H₄-CO- (para) | 33 |
| IIIa-5-50 | $CH_3CH_2$ | H | $CH_3(CH_2)_3OOC$-C₆H₄-CO- (para) | 33 |
| IIIa-5-51 | $CH_3CH_2$ | H | CH≡C—CO— | 44 |
| IIIa-5-52 | $CH_3CH_2$ | H | $(CH_3)_2CHCH_2CH_2$-C₆H₄-CHCO-CH₃ (para) | 33 |
| IIIa-5-53 | $CH_3CH_2$ | H | $(CH_3)_2CH$-CH=C(H)-CO- | 33 |
| IIIa-5-54 | $CH_3CH_2$ | H | $(CH_3)_2CH$-C(CH₃)=CHCH₂CH₂C(CH₃)=CH-CO- | 33 |
| IIIa-5-55 | $CH_3CH_2$ | H | $CH_3CH_2CHCH_2CH_2CH_2CH_2CO-$ with $CH_3$ branch | 33 |
| IIIa-5-56 | $CH_3CH_2$ | H | furan-3-yl-CH=CHCO- | 44 |
| IIIa-5-57 | $CH_3CH_2$ | H | pyridin-3-yl-CH₂CO- | 33 |

TABLE 13-continued
| Compound No. | $R_1$ | $R_3$ | $R_5$ | % Inhibition of Ulcer 50 mg/kg i.p. (%) |
|---|---|---|---|---|
| IIIa-5-58 | $CH_3CH_2$ | H | 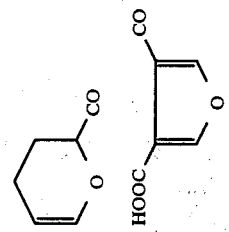 | 44 |
| IIIa-5-59 | $CH_3CH_2$ | H | 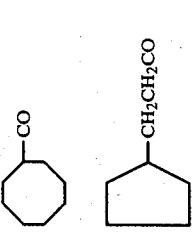 | 44 |
| IIIa-5-60 | $CH_3CH_2$ | H | 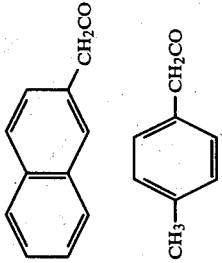 | 44 |
| IIIa-5-61 | $CH_3CH_2$ | H | 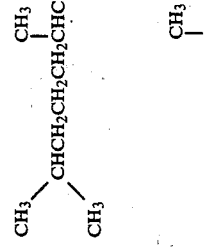 | 33 |
| IIIa-5-62 | $CH_3CH_2$ | H |  | 33 |
| IIIa-5-63 | $CH_3CH_2$ | H | 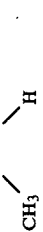 | 33 |
| IIIa-5-64 | $CH_3CH_2$ | H |  | 33 |
| IIIa-5-65 | $CH_3CH_2$ | H |  | 33 |

TABLE 13-continued

| Compound No. | R₁ | R₃ | R₅ | % Inhibition of Ulcer 50 mg/kg i.p. (%) |
|---|---|---|---|---|
| IIIa-5-66 | $CH_3CH_2$ | H | (4-methoxycarbonylcyclohexyl)carbonyl | 44 |
| IIIa-5-67 | $CH_3CH_2$ | H | (4-isopropylphenyl)carbonyl | 44 |
| IIIa-5-68 | $CH_3CH_2$ | H | substituted azulenyl carbonyl | 33 |
| IIIa-5-69 | $CH_3CH_2$ | H | norbornenyl carbonyl | 33 |
| IIIa-5-70 | $CH_3CH_2$ | H | camphor-derived carbonyl | 33 |
| IIIa-5-71 | $CH_3CH_2$ | H | (4-methoxycyclohexyl)carbonyl | 33 |
| IIIa-5-72 | $CH_3CH_2$ | H | tetrazolyl-$CH_2CO$ | 44 |

TABLE 13-continued

| Compound No. | $R_1$ | $R_3$ | $R_5$ | % Inhibition of Ulcer 50 mg/kg i.p. (%) |
|---|---|---|---|---|
| IIIa-5-73 | $CH_3CH_2$ | H | $CH_3(CH_2)_4$—C$_6$H$_4$—CO | 44 |
| IIIa-5-74 | $CH_3CH_2$ | H | $CH_3CH_2CH_2CH$=CH—C$_6$H$_4$—CO | 44 |
| IIIa-5-75 | $CH_3CH_2$ | H | $HOCH_2(CH_2)_8CO$ | 33 |
| IIIa-5-76 | $CH_3CH_2$ | H | cyclopropyl-$CH_2CO$ | 33 |
| IIIa-5-77 | $CH_3CH_2$ | H | $Br(CH_3)C$=$C(CH_3)CO$ | 44 |
| IIIa-5-78 | $CH_3CH_2$ | H | $(CH_3)_2C$=$CHCO$ | 44 |
| IIIa-5-79 | $CH_3CH_2$ | H | $CH_3$—C(SCH$_3$)(CH$_3$)—$CH_2CO$ | 44 |
| IIIa-5-80 | $CH_3CH_2$ | H | $CH_3$—C(OCH$_3$)(CH$_3$)—$CH_2CO$ | 44 |
| IIIa-5-81 | $CH_3$ | H | $CH_3(CH_2)_2CO$ | 44 |
| IIa-5-82 | $CH_3CH_2$ | H | $CH_3(CH_2)_2CO$ | 44 |
| IIIa-5-83 | $CH_3(CH_2)_2CH_2$ | H | $CH_3(CH_2)_2CO$ | 44 |
| IIIa-5-84 | $(CH_3)_2CHCH_2CH_2$ | H | $CH_3(CH_2)_2CO$ | 33 |
| IIIa-5-85 | $CH_3(CH_2)_{16}CH_2$ | H | $CH_3(CH_2)_2CO$ | 33 |
| IIIa-5-86 | $ClCH_2CH_2$ | H | $CH_3(CH_2)_2CO$ | 44 |
| IIa-5-87 | $HC(CH_2)_7CH_3$=$HC(CH_2)_7CH_2$ | H | $CH_3(CH_2)_2CO$ | 33 |

TABLE 13-continued

| Compound No. | R₁ | R₃ | R₅ | % Inhibition of Ulcer 50 mg/kg i.p. (%) |
|---|---|---|---|---|
| IIIa-5-88 | (1-adamantyl) | H | CH₃(CH₂)₂CO | 33 |
| IIIa-5-89 | C₆H₅-CH₂- | H | CH₃(CH₂)₂CO | 33 |
| IIIa-5-90 | cyclopropyl | H | CH₃(CH₂)₂CO | 44 |
| IIIa-5-91 | cyclohexyl-CH₂- | H | CH₃(CH₂)₂CO | 44 |
| IIIa-5-92 | C₆H₅-CH₂CH₂- | H | CH₃(CH₂)₂CO | 44 |
| IIIa-5-93 | 2,3-dihydrofuran-2-yl-CH₂- | H | CH₃(CH₂)₂CO | 44 |
| IIIa-5-94 | tetrahydrofuran-2-yl-CH₂- | H | CH₃(CH₂)₂CO | 44 |
| IIIa-5-95 | tetrahydropyran-2-yl-CH₂CH₂- | H | CH₃(CH₂)₂CO | 33 |

TABLE 13-continued
| Compound No. | R₁ | R₃ | R₅ | % Inhibition of Ulcer 50 mg/kg i.p. (%) |
|---|---|---|---|---|
| IIIa-5-96 | 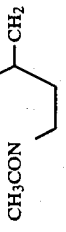 | H | $CH_3(CH_2)_2CO$ | 33 |
| IIIa-5-97 | 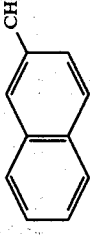 | H | $CH_3(CH_2)_2CO$ | 33 |
| IIIa-5-98 | 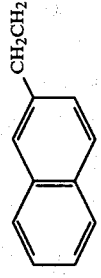 | H | $CH_3(CH_2)_2CO$ | 33 |
| IIIa-5-99 | $BrCH_2CH_2$ | H | $CH_3(CH_2)_2CO$ | 44 |
| IIIa-5-100 | $CH_3CH_2CCH_2$ with =O | H | $CH_3(CH_2)_2CO$ | 33 |
| IIIa-5-101 |  | H | $CH_3(CH_2)_2CO$ | 33 |
| IIIa-5-102 | 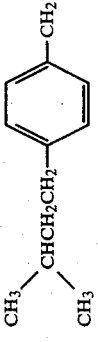 | H | $CH_3(CH_2)_2CO$ | 33 |
| IIIa-5-103 | 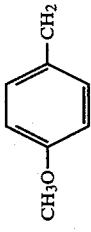 | H | $CH_3(CH_2)_2CO$ | 33 |
| IIIa-5-104 |  | H | $CH_3(CH_2)_2CO$ | 33 |

TABLE 13-continued

| Compound No. | R$_1$ | R$_3$ | R$_5$ | % Inhibition of Ulcer 50 mg/kg i.p. (%) |
|---|---|---|---|---|
| IIIa-5-105 | CH$_3$O-CH(CH$_3$)CH$_2$CH$_2$ | H | CH$_3$(CH$_2$)$_2$CO | 33 |
| IIIa-5-106 | CH$_3$(CH$_2$)$_4$O-CH(CH$_3$)CH$_2$CH$_2$ | H | CH$_3$(CH$_2$)$_2$CO | 33 |
| IIIa-5-107 | CH$_3$COO-CH(CH$_3$)CH$_2$CH$_2$ | H | CH$_3$(CH$_2$)$_2$CO | 44 |
| IIIa-5-108 | CH$_3$(CH$_2$)$_3$CH$_2$COO-CH(CH$_3$)CHCH$_2$CH$_2$ | H | CH$_3$(CH$_2$)$_2$CO | 33 |
| IIIa-5-109 | (CH$_3$)$_2$C=CHCH$_2$CH$_2$C(CH$_3$)=C(CH$_2$)H | H | CH$_3$(CH$_2$)$_2$CO | 44 |
| IIIa-5-110 | CH$_3$CH$_2$CH(CH$_3$)(CH$_2$)$_4$CH$_2$ | H | CH$_3$(CH$_2$)$_2$CO | 33 |
| IIIa-5-111 | CH=CHCH$_2$- (2,5-dihydrofuranyl) | H | CH$_3$(CH$_2$)$_2$CO | 33 |
| IIIa-5-112 | cyclooctyl-CH$_2$ | H | CH$_3$(CH$_2$)$_2$CO | 33 |
| IIIa-5-113 | cyclopentyl-CH$_2$CH$_2$CH$_2$ | H | CH$_3$(CH$_2$)$_2$CO | 33 |

TABLE 13-continued
| Compound No. | R₁ | R₃ | R₅ | % Inhibition of Ulcer 50 mg/kg i.p. (%) |
|---|---|---|---|---|
| IIIa-5-114 | 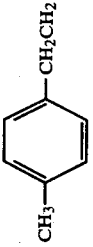 | H | $CH_3(CH_2)_2CO$ | 44 |
| IIIa-5-115 | 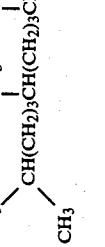 | H | $CH_3(CH_2)_2CO$ | 33 |
| IIIa-5-116 | 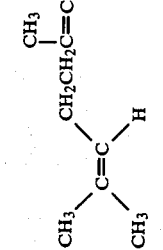 | H | $CH_3(CH_2)_2CO$ | 44 |
| IIIa-5-117 | 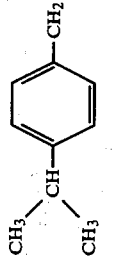 | H | $CH_3(CH_2)_2CO$ | 33 |
| IIIa-5-118 |  | H | $CH_3(CH_2)_2CO$ | 33 |
| IIIa-5-119 | 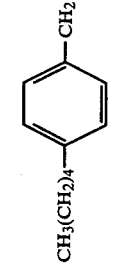 | H | $CH_3(CH_2)_2CO$ | 33 |
| IIIa-5-120 |  | H | $CH_3(CH_2)_2CO$ | 33 |

TABLE 13-continued

| Compound No. | R₁ | R₃ | R₅ | % Inhibition of Ulcer 50 mg/kg i.p. (%) |
|---|---|---|---|---|
| IIIa-5-121 | $CH_3$$\diagdown$CH$\diagup$$CH_3$ | H | $CH_3(CH_2)_2CO$ | 33 |
| IIIa-5-122 | $CH_3CH_2$ | H | 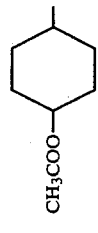$CH_3COO$— | 33 |
| IIIa-5-123 | 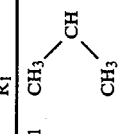 (adamantyl) | H | $CCl_3CO$ | 33 |
| IIIa-5-124 | 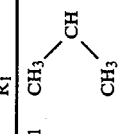—$CH_2CH_2CH_2$— | H | $CCl_3CO$ | 33 |
| IIIa-5-125 | $CH_3CH_2CCH_2$—$\parallel$O | H | $CCl_3CO$ | 33 |
| IIIa-6-1 | $CH_3CH_2$ | $CCl_3CO$ | $CCl_3CO$ | 33 |
| IIIa-6-2 | $CH_3$$\diagdown$CHCH$_2$—$\diagup$$CH_3$ | $CH_3CO$ | $CH_3CO$ | 33 |
| IIIa-6-3 | $CH_3CH_2$ | $CH_3CO$ | $CH_3$$\diagdown$CHCH$_2$CO$\diagup$$CH_3$ | 33 |
| IIIa-6-4 | $CH_3CH_2$ | $CH_3CO$ | $CH_3(CH_2)_{16}CO$ | 22 |
| IIIa-6-5 | $CH_3CH_2$ | $CH_3CO$ | $HC(CH_2)_7CH_3$$\parallel$$HC(CH_2)_7CO$ | 22 |

TABLE 13-continued

| Compound No. | $R_1$ | $R_3$ | $R_5$ | % Inhibition of Ulcer 50 mg/kg i.p. (%) |
|---|---|---|---|---|
| IIIa-6-6 | $CH_3(CH_2)_{16}CH_2$ | $CH_3CO$ | 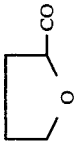 | 33 |
| IIIa-6-7 | $CH_3CH_2$ | $CH_3CO$ | $CH_3O-CHCH_2CO$ <br> $\quad\quad\quad\; CH_3$ | 33 |
| IIIa-6-8 | $CH_3CH_2$ | $CH_3CO$ | 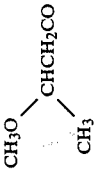 | 22 |
| IIIa-6-9 | $CH_3CH_2$ | $CH_3CO$ | 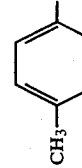 | 22 |
| IIIa-6-10 |  | $CH_3CH_2CO$ | $CH_3CO$ | 33 |
| IIIa-6-11 | 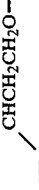 | $CH_3CH_2CH_2CO$ | $CH_3CH_2CH_2CO$ | 33 |
| IIIa-6-12 | $CH_3$ | $CH_3CH_2CO$ | $CH_3CO$ | 33 |
| IIIa-6-13 | $CH_3CH_2$ | $CH_3CH_2CO$ | $CCl_3CO$ | 33 |
| IIIa-7-1 | $CH_3CH_2$ | $CH_3$ | $CH_3CO$ | 33 |
| IIIa-7-2 | $CH_3CH_2$ | $CH_3CH_2$ | $CH_3CO$ | 33 |
| IIIa-7-3 | $CH_3CH_2$ | $CH_3CH_2$ | $CH_3-CHCH_2CO$ <br> $\quad\; CH_3$ | 33 |
| IIIa-7-4 | $CH_3(CH_2)_5CH_2$ | $CH_3CH_2$ | $CH_3(CH_2)_{16}CO$ | 22 |

TABLE 13-continued

| Compound No. | R₁ | R₃ | R₅ | % Inhibition of Ulcer 50 mg/kg i.p. (%) |
|---|---|---|---|---|
| IIIa-7-5 | CH₃CH₂ | CH₃CH₂ | HC(CH₂)₇CH₃<br>∥<br>HC(CH₂)₇CH₂ | 22 |
| IIIa-7-6 | CH₃CH₂ | CH₃ | (tetrahydrofuran-2-carbonyl) | 22 |
| IIIa-7-7 | CH₃CH₂ | CH₃ | CH₃O—CHCH₂CO<br>　　　　|<br>　　　　CH₃ | 33 |
| IIIa-7-8 | CH₃CH₂ | CH₃CH₂CH₂CH₂ |  | 22 |
| IIIa-7-9 | CH₃CH₂ | CH₃ | 4-CH₃—C₆H₄—CO | 22 |
| IIIa-7-10 | CH₃ | CH₃CH₂CH₂CH₂ | (CH₃)₂CH—CHCH₂CH₂O—C₆H₄—CO<br>　　　　　|<br>　　　　　CH₃ | 33 |
| IIIa-7-11 | C₆H₅CH₂ | (CH₃)₂CH | CH₃CH₂CH₂CO | 33 |
| IIIa-7-12 | C₆H₁₁CH₂ | (CH₃)₂CH | CH₃CH₂CH₂CO | 33 |
| IIIa-7-13 | naphthyl-CH₂ | CH₃ | CH₃CH₂CH₂CO | 33 |

TABLE 13-continued

| Compound No. | R₁ | R₃ | R₅ | % Inhibition of Ulcer 50 mg/kg i.p. (%) |
|---|---|---|---|---|
| IIIa-7-14 | (tetrahydropyran-2-yl)CH₂– | CH₃ | CH₃CH₂CH₂CO | 33 |
| IIIa-7-15 | CH₃(CH₂)₃CH₂COOCH(CH₃)CHCH₂CH₂– | CH₃ | CH₃CH₂CH₂CO | 33 |
| IIIa-7-16 | CH₃(CH₂)₂CH₂ | CH₃ | CH₃CO | 33 |
| IIIa-7-17 | CH₃CH₂ | CH₃CH₂CH₂CH₂ | CCl₃CO | 33 |
| IIIa-8-1 | H | CH₃CH₂CH₂CH₂ | CH₃CO | 56 |
| IIIa-8-2 | H | CH₃CH₂CH₂CH₂ | (CH₃)₂CHCO | 56 |
| IIIa-8-3 | H | CH₃CH₂CH₂CH₂ | CH₃(CH₂)₁₆CO | 44 |
| IIIa-8-4 | H | CH₃CH₂CH₂CH₂ | HC(CH₂)₇CH₃ ∥ HC(CH₂)₇CO | 44 |
| IIIa-8-5 | H | CH₃CH₂CH₂CH₂ | (tetrahydrofuran-2-yl)CO | 44 |
| IIIa-8-6 | H | CH₃CH₂CH₂CH₂ | CH₃OCH(CH₃)CH₂CO | 56 |
| IIIa-8-7 | H | CH₃CH₂CH₂CH₂ | 4-CH₃-C₆H₄-CO | 44 |
| IIIa-8-8 | H | CH₃CH₂CH₂CH₂ | 4-[CH(CH₃)CH₂CH₂O]-C₆H₄-CO (with CH₃) | 44 |
| IIIa-8-9 | H | CH₃ | CH₃CO | 56 |
| IIIa-8-10 | H | CH₃ | CCl₃CO | 56 |
| IIIa-9-1 | CH₃CO | CH₃CH₂CH₂CH₂ | CH₃CO | 33 |
| IIIa-9-2 | CH₃CO | CH₃CH₂CH₂CH₂ | (CH₃)₂CHCO | 33 |

TABLE 13-continued

| Compound No. | R₁ | R₃ | R₅ | % Inhibition of Ulcer 50 mg/kg i.p. (%) |
|---|---|---|---|---|
| IIIa-9-3 | $CH_3CO$ | $CH_3CH_2CH_2CH_2$ | $CH_3(CH_2)_{16}CO$ | 22 |
| IIIa-9-4 | $CH_3CO$ | $CH_3CH_2CH_2CH_2$ | tetrahydrofuran-2-CO | 22 |
| IIIa-9-5 | $CH_3(CH_2)_{16}CO$ | $CH_3CH_2CH_2CH_2$ | $CH_3CO$ | 33 |
| IIIa-9-6 | $CH_3(CH_2)_{16}CO$ | $CH_3CH_2CH_2CH_2$ | $HC(CH_2)_7CH_3$ $=$ $HC(CH_2)_7CO$ | 22 |
| IIIa-9-7 | $CH_3(CH_2)_{16}CO$ | $CH_3CH_2CH_2CH_2$ | $CH_3O-CHCH_2CO$ ($CH_3$) | 33 |
| IIIa-9-8 | $CH_3(CH_2)_{16}CO$ | $CH_3CH_2CH_2CH_2$ | $CH_3$-C₆H₄-CO | 22 |
| IIIa-9-9 | $(CH_3)_2CHCO$ | $CH_3$ | $CH_3CO$ | 33 |
| IIIa-10-1 | H | $CH_3CO$ | H | 66 |
| IIIa-10-2 | H | $CH_3CH_2CO$ | H | 66 |
| IIIa-10-3 | H | $CH_3(CH_2)_2CO$ | H | 66 |
| IIIa-10-4 | H | $CH_3(CH_2)_3CO$ | H | 66 |
| IIIa-10-5 | H | $CH_3(CH_2)_4CO$ | H | 66 |
| IIIa-10-6 | H | $CH_3(CH_2)_5CO$ | H | 66 |
| IIIa-10-7 | H | $CH_3(CH_2)_6CO$ | H | 66 |
| IIIa-10-8 | H | $CH_3(CH_2)_{10}CO$ | H | 56 |
| IIIa-10-9 | H | $CH_3(CH_2)_{16}CO$ | H | 66 |
| IIIa-10-10 | H | $(CH_3)_2CHCO$ | H | 66 |
| IIIa-10-11 | H | $(CH_3)_2CHCH_2CO$ | H | |
| IIIa-10-12 | H | $HC(CH_2)_7CH_3$ $=$ $HC(CH_2)_7CO$ | H | 56 |
| IIIa-10-13 | H | $CCl_3CO$ | H | 66 |
| IIIa-10-14 | H | $CH_3-C=CHCH_2CH_2C=C(CH_3)-CH=CH-CO$ ($CH_3$) | H | 66 |

TABLE 13-continued

| Compound No. | R₁ | R₃ | R₅ | % Inhibition of Ulcer 50 mg/kg i.p. (%) |
|---|---|---|---|---|
| IIIa-10-15 | H | cyclopentyl-CH₂CH₂CO | H | 66 |
| IIIa-10-16 | H | 4-CH₃O-C₆H₄-CO | H | 66 |
| IIIa-10-17 | H | CH₃O-CH(CH₃)-CH₂CO | H | 66 |
| IIIa-10-18 | H | (CH₃)(H)C=C(H)(CO) | H | 66 |
| IIIa-11-1 | CH₃CO | CH₃CO | H | 56 |
| IIIa-11-2 | CH₃CO | (CH₃)₂CHCO | H | 56 |
| IIIa-11-3 | (CH₃)₂CHCO | (CH₃)₂CHCO | H | 56 |
| IIIa-11-4 | CCl₃CO | CCl₃CO | H | 56 |
| IIIa-11-5 | CH₃CH₂CO | HC(CH₂)₇CH₃=HC(CH₂)₇CO | H | 44 |
| IIIa-11-6 | CH₃(CH₂)₂CO | CH₃CO | H | 56 |
| IIIa-12-1 | CH₃CO | H | H | 78 |
| IIIa-12-2 | (CH₃)₂CHCO | H | H | 78 |
| IIIa-12-3 | CH₃(CH₂)₁₆CO | H | H | 66 |
| IIIa-12-4 | HC(CH₂)₇CH₃=HC(CH₂)₇CO | H | H | 72 |
| IIIa-12-5 | tetrahydrofuran-2-carbonyl | H | H | 78 |

TABLE 13-continued

| Compound No. | R₁ | R₃ | R₅ | % Inhibition of Ulcer 50 mg/kg i.p. (%) |
|---|---|---|---|---|
| IIIa-12-6 | CH₃O-CHCH₂CO / CH₃ | H | H | 78 |
| IIIa-12-7 | 4-CH₃-C₆H₄-CO | H | H | 78 |
| IIIa-12-8 | CH₃-CH(CH₃)-CHCH₂CH₂O-C₆H₄-CO | H | H | 72 |
| IIIa-13-1 | CCl₃CO | H | H | 66 |
| IIIa-13-1 | CH₃ | H | H | 100 |
| IIIa-13-2 | CH₃CH₂ | H | H | 94 |
| IIIa-13-3 | CH₃(CH₂)₂CH₂ | H | H | 100 |
| IIIa-13-4 | (CH₃)₂CHCH₂CH₂ | H | H | 100 |
| IIIa-13-5 | CH₃(CH₂)₁₆CH₂ | H | H | 72 |
| IIIa-13-6 | ClCH₂CH₂ | H | H | 94 |
| IIIa-13-7 | HC(CH₂)₇CH₃ = HC(CH₂)₇CH₂ | H | H | 72 |
| IIIa-13-8 | adamantyl | H | H | 89 |
| IIIa-13-9 | C₆H₅-CH₂ | H | H | 89 |
| IIIa-13-10 | cyclopropyl | H | H | 94 |

TABLE 13-continued

| Compound No. | R$_1$ | R$_3$ | R$_5$ | % Inhibition of Ulcer 50 mg/kg i.p. (%) |
|---|---|---|---|---|
| IIIa-13-11 | cyclohexyl-CH$_2$ | H | H | 78 |
| IIIa-13-12 | phenyl-CH$_2$CH$_2$ | H | H | 89 |
| IIIa-13-13 | (furan-2-yl)-CH$_2$ | H | H | 89 |
| IIIa-13-14 | (tetrahydrofuran-2-yl)-CH$_2$ | H | H | 89 |
| IIIa-13-15 | (tetrahydropyran-2-yl)-CH$_2$CH$_2$ | H | H | 94 |
| IIIa-13-16 | (1-acetylpiperidin-4-yl) | H | H | 89 |
| IIIa-13-17 | (naphthalen-2-yl)-CH$_2$ | H | H | 72 |
| IIIa-13-18 | (naphthalen-2-yl)-CH$_2$CH$_2$ | H | H | 72 |
| IIIa-13-19 | BrCH$_2$CH$_2$CH$_2$ | H | H | 100 |

TABLE 13-continued

| Compound No. | $R_1$ | $R_3$ | $R_5$ | % Inhibition of Ulcer 50 mg/kg i.p. (%) |
|---|---|---|---|---|
| IIIa-13-20 | $CH_3CH_2\overset{O}{C}CH_2$— | H | H | 100 |
| IIIa-13-21 | 4-$CH_3$-$C_6H_4$-$CH_2$— | H | H | 89 |
| IIIa-13-22 | $(CH_3)_2CHCH_2CH_2$-($C_6H_4$)-$CH_2$— | H | H | 72 |
| IIIa-13-23 | 4-$CH_3O$-$C_6H_4$-$CH_2$— | H | H | 72 |
| IIIa-13-24 | $(CH_3)_2CHCH_2CH_2O$-($C_6H_4$)-$CH_2$— | H | H | 72 |
| IIIa-13-25 | $CH_3O$-$CH(CH_3)CH_2CH_2$— | H | H | 89 |
| IIIa-13-26 | $CH_3(CH_2)_4O$-$CH(CH_3)CH_2CH_2$— | H | H | 89 |
| IIIa-13-27 | $CH_3COO$-$CH(CH_3)CH_2CH_2$— | H | H | 89 |

TABLE 13-continued

| Compound No. | R$_1$ | R$_3$ | R$_5$ | % Inhibition of Ulcer 50 mg/kg i.p. (%) |
|---|---|---|---|---|
| IIIa-13-28 | CH$_3$(CH$_2$)$_3$CH$_2$COOCH(CH$_3$)CH$_2$CH$_2$ | H | H | 72 |
| IIIa-13-29 | (CH$_3$)$_2$C=CHCH$_2$CH$_2$C(CH$_3$)=CHCH$_2$— | H | H | 89 |
| IIIa-13-30 | CH$_3$CH$_2$CH(CH$_3$)(CH$_2$)$_4$CH$_2$— | H | H | 94 |
| IIIa-13-31 | 2,5-dihydrofuran-3-yl-CH=CHCH$_2$— | H | H | 100 |
| IIIa-13-32 | cycloheptyl-CH$_2$— | H | H | 89 |
| IIIa-13-33 | cyclopentyl-CH$_2$CH$_2$CH$_2$— | H | H | 100 |
| IIIa-13-34 | 4-CH$_3$-C$_6$H$_4$-CH$_2$CH$_2$— | H | H | 89 |
| IIIa-13-35 | (CH$_3$)$_2$CHCH(CH$_2$)$_3$CH(CH$_3$)CH(CH$_2$)$_3$CH$_2$— | H | H | 89 |

TABLE 13-continued

| Compound No. | R₁ | R₃ | R₅ | % Inhibition of Ulcer 50 mg/kg i.p. (%) |
|---|---|---|---|---|
| IIIa-13-36 | $CH_3CH_2CH_2\underset{\underset{CH_3}{\mid}}{C}=C\underset{\underset{CH_2CH_2CH_2}{\mid}}{\overset{\overset{H}{\mid}}{C}}-CH_2CH_2\underset{\underset{CH_3}{\mid}}{C}=C\underset{\underset{CH_3}{\mid}}{\overset{\overset{H}{\mid}}{C}}-CH_2CH_2\underset{\underset{CH_3}{\mid}}{C}=C\underset{\underset{CH_3}{\mid}}{\overset{\overset{H}{\mid}}{C}}$ | H | H | 94 |
| IIIa-13-37 | 4-isopropylbenzyl | H | H | 72 |
| IIIa-13-38 | bornyl | H | H | 72 |
| IIIa-13-39 | $CH_3(CH_2)_4$-(4-methylbenzyl) | H | H | 72 |
| IIIa-13-40 | $CH_3CH_2CH_2CH=CH$-(4-methylenephenyl) | H | H | 72 |
| IIIa-13-41 | $(CH_3)_2CH$ | H | H | 100 |
| IIIa-14-1 | $CH_3CH_2$ | $CH_3CO$ | H | 56 |
| IIIa-14-2 | $CH_3CH_2$ | $(CH_3)_2CHCO$ | H | 56 |
| IIIa-14-3 | $CH_3CH_2$ | $CH_3(CH_2)_{16}CO$ | H | 44 |
| IIIa-14-4 | $CH_3CH_2$ | $HC(CH_2)_7CH_3$<br>$\parallel$<br>$HC(CH_2)_7CO$ | H | 44 |

TABLE 13-continued

| Compound No. | R₁ | R₃ | R₅ | % Inhibition of Ulcer 50 mg/kg i.p. (%) |
|---|---|---|---|---|
| IIIa-14-5 | $CH_3CH_2$ | ![tetrahydrofuran-2-CO] (2-tetrahydrofuranyl-CO) | H | 56 |
| IIIa-14-6 | $CH_3CH_2$ | $CH_3O-CH(CH_3)-CH_2CO$ | H | 56 |
| IIIa-14-7 | $CH_3CH_2$ | 4-$CH_3$-C₆H₄-CO | H | 44 |
| III-14-8 | $CH_3CH_2$ | 4-[(CH₃)₂CH-CH₂CH₂O]-C₆H₄-CO | H | 44 |
| IIIa-14-9 | $CH_3CH_2$ | $CH_3CH_2CO$ | H | 56 |
| IIIa-15-1 | $CH_3$ | $CH_3CH_2CH_2CH_2$ | H | 56 |
| IIIa-15-2 | $CH_3(CH_2)_2CH_2$ | $CH_3CH_2CH_2CH_2$ | H | 56 |
| IIIa-15-3 | $CH_3(CH_2)_{17}$ | $CH_3CH_2CH_2CH_2$ | H | 44 |
| IIIa-15-4 | $HC(CH_2)_7CH_3$ $\parallel$ $HC(CH_2)_7CH_2$— | $CH_3CH_2CH_2CH_2$ | H | 44 |
| IIIa-15-5 | 2-tetrahydrofuranyl-CH₂ | $CH_3CH_2CH_2CH_2$ | H | 56 |
| IIIa-15-6 | $CH_3O-CH(CH_3)-CHCH_2CH_2$ | $CH_3CH_2CH_2CH_2$ | H | 56 |
| IIIa-15-7 | C₆H₅-CH₂ | $CH_3CH_2CH_2CH_2$ | H | 44 |

TABLE 13-continued

| Compound No. | R1 | R3 | R5 | % Inhibition of Ulcer 50 mg/kg i.p. (%) |
|---|---|---|---|---|
| IIIa-15-8 | CH₃CH₂ | CH₃CH₂CH₂ | H | 56 |
| IIIa-16-1 | H | CH₃ | H | 72 |
| IIIa-16-2 | H | (CH₃)₂CHCH₂— | H | 66 |
| IIIa-16-3 | H | CH₃(CH₂)₁₇ | H | 56 |
| IIIa-16-4 | H | HC(CH₂)₇CH₃=HC(CH₂)₇CH₂— | H | 56 |
| IIIa-16-5 | H | tetrahydrofurfuryl-CH₂— | H | 56 |
| IIIa-16-6 | H | CH₃O—CH(CH₃)CH₂CH₂— | H | 66 |
| IIIa-16-7 | H | CH₃CH₂ | H | 72 |
| IIIa-17-1 | CH₃CO | CH₃ | H | 56 |
| IIIa-17-2 | CH₃(CH₂)₁₆CO | CH₃ | H | 44 |
| IIIa-17-3 | CH₃CH₂CH₂CO | CH₃CH₂ | H | 56 |
| IIIa-17-4 | CH₃O—CH(CH₃)CHCH₂CO | CH₃CH₂ | H | 56 |
| IIIa-17-5 | CH₃CH₂CO | CH₃ | H | |
| IIIa-17-6 | OCl₃CO | CH₃CH₂ | H | |
| IIIa-18-1 | H | H | CH₃CH₂ | 44 |
| IIIa-18-2 | H | H | CH₃CH₂CH₂ | 56 |
| IIIa-18-3 | H | H | CH₃(CH₂)₂CH₂ | 100 |
| IIIa-18-4 | H | H | (CH₃)₂CHCH₂ | 100 |
| IIIa-18-5 | H | H | (CH₃)₂CHCH₂CH₂ | 94 |
| IIIa-18-6 | H | H | CH₃(CH₂)₃CH₂ | 100 |
| IIIa-18-7 | H | H | CH₃(CH₂)₄CH₂ | 94 |
| IIIa-18-8 | H | H | CH₃(CH₂)₅CH₂ | 100 |
| IIIa-18-9 | H | H | CH₃(CH₂)₆CH₂ | 94 |
| IIIa-18-10 | H | H | CH₃(CH₂)₁₀CH₂ | 94 |
| IIIa-18-11 | H | H | CH₃(CH₂)₁₆CH₂ | 83 |

TABLE 13-continued

| Compound No. | $R_1$ | $R_3$ | $R_5$ | % Inhibition of Ulcer 50 mg/kg i.p. (%) |
|---|---|---|---|---|
| IIIa-18-12 | H | H | $CCl_3CH_2$ | 94 |
| IIIa-18-13 | H | H | $HC(CH_2)_7CH_3$<br>$\|\|$<br>$HC(CH_2)_7CH_2$ | 83 |
| IIIa-18-14 | H | H | $C_6H_5-CH_2-$ | 89 |
| IIIa-18-15 | H | H | naphthyl-$CH_2-$ | 83 |
| IIIa-18-16 | H | H | adamantyl-$CH_2-$ | 89 |
| IIIa-18-17 | H | H | (2-acetamidophenyl)-$CH_2-$ | 83 |
| IIIa-18-18 | H | H | cyclopropyl-$CH_2-$ | 89 |
| IIIa-18-19 | H | H | cyclohexyl-$CH_2CH_2CH_2CH_2-$ | 94 |
| IIIa-18-20 | H | H | $C_6H_5-CH_2CH_2-$ | 89 |

TABLE 13-continued

| Compound No. | $R_1$ | $R_3$ | $R_5$ | % Inhibition of Ulcer 50 mg/kg i.p. (%) |
|---|---|---|---|---|
| IIIa-18-21 | H | H | 1-methyl-2-(CH$_2$CH$_2$)-naphthalenyl | 83 |
| IIIa-18-22 | H | H | furan-2-yl-CH$_2$ | 89 |
| IIIa-18-23 | H | H | tetrahydrofuran-2-yl-CH$_2$ | 89 |
| IIIa-18-24 | H | H | tetrahydropyran-2-yl-CH$_2$CH$_2$ | 94 |
| IIIa-18-25 | H | H | 1-(N-acetyl)pyrrol-2-yl-CH$_2$ | 89 |
| IIIa-18-26 | H | H | BrCH$_2$CH$_2$CH$_2$ | 94 |
| IIIa-18-27 | H | H | CH$_3$CH$_2$CCH$_2$ (O=) | 94 |
| IIIa-18-28 | H | H | 2-oxocyclohexyl-CH$_2$ | 89 |
| IIIa-18-29 | H | H | 4-(CH$_3$COO)-phenyl-CH$_2$ | 94 |

TABLE 13-continued
| Compound No. | $R_1$ | $R_3$ | $R_5$ | % Inhibition of Ulcer 50 mg/kg i.p. (%) |
|---|---|---|---|---|
| IIIa-18-30 | H | H | 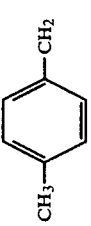 | 89 |
| IIIa-18-31 | H | H | $CH_2COOCH_2CH_3$ $-CH_2CH_2$ | 100 |
| IIIa-18-32 | H | H |  | 89 |
| IIIa-18-33 | H | H | 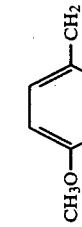 | 89 |
| IIIa-18-34 | H | H |  | 89 |
| IIIa-18-35 | H | H |  | 89 |
| IIIa-18-36 | H | H | 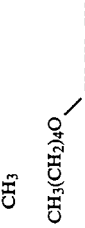 | 94 |
| IIIa-18-37 | H | H | 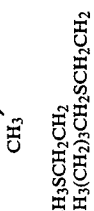 | 94 |
| IIIa-18-38 | H | H | $CH_3SCH_2CH_2$ | 94 |
| IIIa-18-39 | H | H | $CH_3(CH_2)_3CH_2SCH_2CH_2$ | 94 |

TABLE 13-continued

| Compound No. | R$_1$ | R$_3$ | R$_5$ | % Inhibition of Ulcer 50 mg/kg i.p. (%) |
|---|---|---|---|---|
| IIIa-18-40 | H | H | 4-(CH$_3$S)C$_6$H$_4$-CH$_2$- | 94 |
| IIIa-18-41 | H | H | 4-(CH$_3$(CH$_2$)$_3$CH$_2$S)C$_6$H$_4$-CH$_2$- | 89 |
| IIIa-18-42 | H | H | CH$_3$COO-CH(CH$_3$)-CH$_2$CH$_2$- | 94 |
| IIIa-18-43 | H | H | CH$_3$(CH$_2$)$_3$CH$_2$COO-CH(CH$_3$)-CH$_2$CH$_2$- | 94 |
| IIIa-18-44 | H | H | 4-(CH$_3$OOC)C$_6$H$_4$-CH$_2$- | 89 |
| IIIa-18-45 | H | H | 4-(CH$_3$(CH$_2$)$_3$CH$_2$OOC)C$_6$H$_4$-CH$_2$- | 89 |
| IIIa-18-46 | H | | CH≡C-CH(CH$_3$)-CH$_2$- | 100 |
| IIIa-18-47 | H | H | 4-((CH$_3$)$_2$CHCH$_2$CH$_2$)C$_6$H$_4$-CH(CH$_3$)-CH$_2$- | 89 |
| IIIa-18-48 | H | H | (CH$_3$)(H)C=C(H)-CH$_2$- | 94 |

TABLE 13-continued

| Compound No. | $R_1$ | $R_3$ | $R_5$ | % Inhibition of Ulcer 50 mg/kg i.p. (%) |
|---|---|---|---|---|
| IIIa-18-49 | H | H | $CH_3-\overset{CH_3}{\underset{CH_3}{C}}-CH=CHCH_2CH_2\overset{CH_3}{\underset{}{C}}=C\overset{CH_2}{\underset{H}{}}$ | 89 |
| IIIa-18-50 | H | H | $CH_3CH_2CHCH_2CH_2CH_2CH_2$ with $CH_3$ branch | 94 |
| IIIa-18-51 | H | H | furan-CH=CHCH$_2$ | 89 |
| IIIa-18-52 | H | H | $HOCH_2(CH_2)_3CH_2$ | 94 |
| IIIa-18-53 | H | H | dihydropyranyl-CH$_2$ | 89 |
| IIIa-18-54 | H | H | furan with HOOC and CH$_2$ substituents | 89 |
| IIIa-18-55 | H | H | cyclohexyl with COOH, CH$_3$, and CH$_2$ | 83 |
| IIIa-18-56 | H | H | cycloheptyl-CH$_2$ | 89 |
| IIIa-18-57 | H | H | cyclopentyl-CH$_2$CH$_2$CH$_2$ | 94 |

TABLE 13-continued
| Compound No. | $R_1$ | $R_3$ | $R_5$ | % Inhibition of Ulcer 50 mg/kg i.p. (%) |
|---|---|---|---|---|
| IIIa-18-58 | H | H | 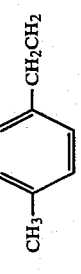 | 83 |
| IIIa-18-59 | H | H |  | 89 |
| IIIa-18-60 | H | H | $CH_3$ $CH_3$<br>$CH(CH_2)_3CH(CH_2)_3CH(CH_2)CH_2$<br>$CH_3$<br>$CH_3$ | 89 |
| IIIa-18-61 | H | H | $CH_3$ $CH_2CH_2CH_2$<br>$CH_2CH_2C=C$ H<br>$CH_3$<br>$CH_2CH_2C=C$ H<br>$CH_3$<br>$C=C$ H<br>$CH_3$ $CH_3$ | 89 |
| IIIa-18-62 | H | H | 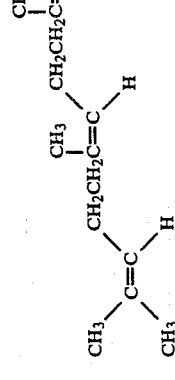 | 89 |
| IIIa-18-63 | H | H | 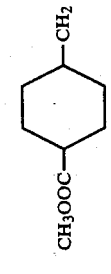 | 83 |
| IIIa-18-64 | H | H |  | 83 |

TABLE 13-continued

| Compound No. | R₁ | R₃ | R₅ | % Inhibition of Ulcer 50 mg/kg i.p. (%) |
|---|---|---|---|---|
| IIIa-18-65 | H | H | CH₃O–C₆H₁₀–CH₂– | 89 |
| IIIa-18-66 | H | H | CH₃COO–C₆H₁₀–CH₂– | 89 |
| IIIa-18-67 | H | H | CH₃(CH₂)₄–C₆H₄–CH₂– | 89 |
| IIIa-18-68 | H | H | CH₃CH₂CH₂CH=CH–C₆H₄–CH₂– | 83 |
| IIIa-18-69 | H | H | Br(CH₃)C=C(CH₃)CH₂ | 89 |
| IIIa-18-70 | H | H | (CH₃)₂C=CHCH₂ | 94 |
| IIIa-18-71 | H | H | CH₃–C(SCH₃)(CH₃)–CH₂CH₂– | 89 |
| IIIa-18-72 | H | H | CH₃–C(OCH₃)(CH₃)–CH₂CH₂– | 89 |
| IIIa-19-1 | H | CH₃CO | CH₃CH₂ | 66 |
| IIIa-19-2 | H | CH₃CO | (CH₃)₂CHCH₂CH₂– | 66 |
| IIIa-19-3 | H | CH₃CO | CH₃(CH₂)₁₆CH₂ | 56 |

TABLE 13-continued

| Compound No. | $R_1$ | $R_3$ | $R_5$ | % Inhibition of Ulcer 50 mg/kg i.p. (%) |
|---|---|---|---|---|
| IIIa-19-4 | H | $CH_3CO$ | $HC(CH_2)_7CH_3$ <br> $\parallel$ <br> $HC(CH_2)_7CH_2$ | 56 |
| IIIa-19-5 | H | $CH_3CO$ | tetrahydrofuran-2-yl-$CH_2$ | 66 |
| IIIa-19-6 | H | $CH_3CO$ | $CH_3O$-$CHCH_2CH_2$-$CH_3$ | 66 |
| IIIa-19-7 | H | $CH_3CO$ | $CH_3$-C$_6$H$_4$-$CH_2$ | 66 |
| IIIa-19-8 | H | $CH_3CO$ | $CH_3$-CH($CH_3$)-$CHCH_2O$-C$_6$H$_4$-$CH_2$ | 56 |
| IIIa-19-9 | H | $CH_3CH_2CO$ | $CH_3CH_2$ | 66 |
| IIIa-19-10 | H | $CH_3CH_2CH_2CO$ | $CH_3CH_2CH_2CH_2$ | 66 |
| IIIa-20-1 | $CH_3CO$ | $CH_3CO$ | $CH_3CH_2$ | 56 |
| IIIa-20-2 | $(CH_3)_2CHCO$ | $CH_3CH_2CO$ | $CH_3CH_2$ | 56 |
| IIIa-20-3 | $CH_3CO$ | $CH_3CO$ | $(CH_3)_2CHCH_2CH_3$ | 56 |
| IIIa-20-4 | $CH_2CO$ | $CH_3CO$ | $CH_3(CH_2)_{16}CH_2$ | 44 |
| IIIa-20-5 | $CH_3CO$ | $CH_3CO$ | $HC(CH_2)_7CH_3$ <br> $\parallel$ <br> $HC(CH_2)_7CH_2$ | 44 |
| IIIa-20-6 | $CH_3CO$ | $CH_3CO$ | tetrahydrofuran-2-yl-$CH_2$ | 44 |
| IIIa-20-7 | $CH_3CO$ | $CH_3CO$ | $CH_3O$-$CHCH_2CH_2$-$CH_3$ | 56 |

TABLE 13-continued

| Compound No. | $R_1$ | $R_3$ | $R_5$ | % Inhibition of Ulcer 50 mg/kg i.p. (%) |
|---|---|---|---|---|
| IIIa-20-8 | $CH_3CO$ | $CH_3CO$ | $CH_3$–⟨C₆H₄⟩–$CH_2$ | 44 |
| IIIa-20-9 | $CH_3CO$ | $CH_3CO$ | $(CH_3)_2CHCH_2CH_2O$–⟨C₆H₄⟩–$CH_2$ | 44 |
| IIIa-20-10 | $CH_3CO$ | $CH_3CO$ | $CCl_3CH_2$ | 56 |
| IIIa-21-1 | $CH_3CO$ | H | $CH_3CH_2$ | 78 |
| IIIa-21-2 | $CH_3CO$ | H | $(CH_3)_2CHCH_2$ | 72 |
| IIIa-21-3 | $CH_3CO$ | H | $CH_3(CH_2)_{16}CH_2$ | 66 |
| IIIa-21-4 | $CH_3CO$ | H | $HC(CH_2)_7CH_3$ ‖ $HC(CH_2)_7CH_2$ | 66 |
| IIIa-21-5 | $CH_3CO$ | H | tetrahydrofurfuryl-$CH_2$ | 72 |
| IIIa-21-6 | $CH_3CO$ | H | $CH_3OCHCH_2CH_2$ with $CH_3$ | 78 |
| IIIa-21-7 | $CH_3CO$ | H | $CH_3$–⟨C₆H₄⟩–$CH_2$ | 66 |
| IIIa-21-8 | $CH_3CO$ | H | $(CH_3)_2CHCH_2CH_2O$–⟨C₆H₄⟩–$CH_2$ | 66 |
| IIIa-22-1 | $CH_3CH_2CO$ | H | $CH_3CH_2$ | 66 |
| IIIa-22-1 | $CH_3CH_2$ | H | $CH_3CH_2$ | 94 |
| IIIa-22-2 | $CH_3CH_2$ | H | $(CH_3)_2CHCH_2CH_2$ | 94 |
| IIIa-22-3 | $CH_3(CH_2)_2CH_2$ | H | $CH_3CH_2$ | 94 |

TABLE 13-continued

| Compound No. | R₁ | R₃ | R₅ | % Inhibition of Ulcer 50 mg/kg i.p. (%) |
|---|---|---|---|---|
| IIIa-22-4 | (CH₃)₂CHCH₂ | H | (CH₃)₂CHCH₂ | 94 |
| IIIa-22-5 | CH₃ | H | CH₃CH₂ | 94 |
| IIIa-22-6 | CH₃(CH₂)₃CH₂ | H | CH₃(CH₂)₁₆CH₂ | 72 |
| IIIa-22-7 | CH₃ | H | CCl₃CH₂ | 78 |
| IIIa-22-8 | HC(CH₂)₇CH₃ ‖ HC(CH₂)₇CH₂ | H | CH₃CH₂ | 78 |
| IIIa-22-9 | CH₃(CH₂)₁₀CH₂ | H | CH₃CH₂ | 83 |
| IIIa-22-10 | (CH₃)₂CHCH₂ | H | CH₃CH₂ | 83 |
| IIIa-22-11 | CH₃(CH₂)₆CH₂ | H | CH₃CH₂ | 83 |
| IIIa-22-12 | CH₃(CH₂)₆CH₂ | H | CH₃(CH₂)₅CH₂ | 72 |
| IIIa-22-13 | CH₃CH₂ | H | CCl₃CH₂ | 78 |
| IIIa-22-14 | CH₃CH₂ | H | HC(CH₂)₇CH₃ ‖ HC(CH₂)₇CH₂ | 78 |
| IIIa-22-15 | CH₃CH₂ | H | —CH₂—C₆H₅ | 89 |
| IIIa-22-16 | CH₃CH₂ | H | —CH₂—(2-naphthyl) | 83 |
| IIIa-22-17 | CH₃CH₂ | H | —CH₂—cyclopropyl | 89 |
| IIIa-22-18 | CH₃CH₂ | H | —CH₂CH₂CH₂CH₂—cyclohexyl | 94 |
| IIIa-22-19 | CH₃CH₂ | H | —CH₂CH₂—C₆H₅ | 89 |

TABLE 13-continued

| Compound No. | R₁ | R₃ | R₅ | % Inhibition of Ulcer 50 mg/kg i.p. (%) |
|---|---|---|---|---|
| IIIa-22-20 | CH₃CH₂ | H | 1-methyl-2-(CH₂CH₂)-naphthyl | 89 |
| IIIa-22-21 | CH₃CH₂ | H | furan-2-yl-CH₂ | 83 |
| IIIa-22-22 | CH₃CH₂ | H | tetrahydrofuran-2-yl-CH₂ | 83 |
| IIIa-22-23 | CH₃CH₂ | H | tetrahydropyran-2-yl-CH₂CH₂ | 89 |
| IIIa-22-24 | CH₃CH₂ | H | 1-acetyl-2-(CH₂)-pyrrole | 89 |
| IIIa-22-25 | CH₃CH₂ | H | BrCH₂CH₂CH₂ | 89 |
| IIIa-22-26 | CH₃CH₂ | H | CH₃CH₂C(O)CH₂ | 94 |
| IIIa-22-27 | CH₃CH₂ | H | 2-(CH₂)-cyclohexanone | 83 |

TABLE 13-continued
| Compound No. | $R_1$ | $R_3$ | $R_5$ | % Inhibition of Ulcer 50 mg/kg i.p. (%) |
|---|---|---|---|---|
| IIIa-22-28 | $CH_3CH_2$ | H |  | 83 |
| IIIa-22-29 | $CH_3CH_2$ | H | 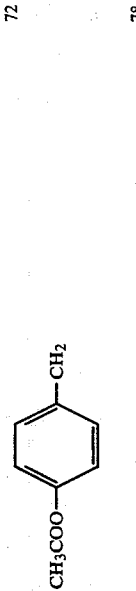 | 83 |
| IIIa-22-30 | $CH_3CH_2$ | H |  | 72 |
| IIIa-22-31 | $CH_3CH_2$ | H |  | 78 |
| IIIa-22-32 | $CH_3CH_2$ | H | $CH_2COOCH_2CH_3$ — $CH_2CH_2$ | 83 |
| IIIa-22-33 | $CH_3CH_2$ | H | 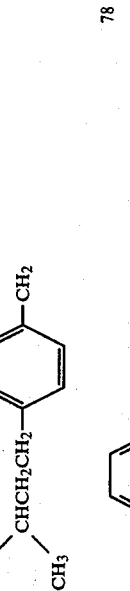 | 78 |
| IIIa-22-34 | $CH_3CH_2$ | H |  | 78 |
| IIIa-22-35 | $CH_3CH_2$ | H |  | 78 |

TABLE 13-continued

| Compound No. | $R_1$ | $R_3$ | $R_5$ | % Inhibition of Ulcer 50 mg/kg i.p. (%) |
|---|---|---|---|---|
| IIIa-22-36 | $CH_3CH_2$ | H | 4-($CH_3$)($CH_3$)CHCH$_2$CH$_2$O—C$_6$H$_4$—CH$_2$— | 78 |
| IIIa-22-37 | $CH_3CH_2$ | H | $CH_3O$—CHCH$_2$CH$_2$— / $CH_3$ | 89 |
| IIIa-22-38 | $CH_3CH_2$ | H | $CH_3(CH_2)_4O$—CHCH$_2$CH$_2$— / $CH_3$ | 83 |
| IIIa-22-39 | $CH_3CH_2$ | H | $CH_3SCH_2CH_2$— | 94 |
| IIIa-22-40 | $CH_3CH_2$ | H | $CH_3(CH_2)_3CH_2SCH_2CH_2$— | 94 |
| IIIa-22-41 | $CH_3CH_2$ | H | 4-$CH_3S$—C$_6$H$_4$—CH$_2$— | 78 |
| IIIa-22-42 | $CH_3CH_2$ | H | 4-$CH_3(CH_2)_3CH_2S$—C$_6$H$_4$—CH$_2$— | 78 |
| IIIa-22-43 | | | $CH_3COO$—CHCH$_2$CH$_2$— / $CH_3$ | 83 |
| IIIa-22-44 | $CH_3CH_2$ | H | $CH_3(CH_2)_3CH_2COO$—CHCH$_2$CH$_2$— / $CH_3$ | 72 |

TABLE 13-continued

| Compound No. | R$_1$ | R$_3$ | R$_5$ | % Inhibition of Ulcer 50 mg/kg i.p. (%) |
|---|---|---|---|---|
| IIIa-22-45 | CH$_3$CH$_2$ | H | CH$_3$OOC–C$_6$H$_4$–CH$_2$– | 78 |
| IIIa-22-46 | CH$_3$CH$_2$ | H | CH$_3$(CH$_2$)$_3$OOC–C$_6$H$_4$–CH$_2$– | 78 |
| IIIa-22-47 | CH$_3$CH$_2$ | H | CH≡C—CH$_2$ | 94 |
| IIIa-22-48 | CH$_3$CH$_2$ | H | (CH$_3$)$_2$CHCH$_2$–C$_6$H$_4$–CHCH$_3$– | 83 |
| IIIa-22-49 | CH$_3$CH$_2$ | H | (CH$_3$)(H)C=C(H)CH$_2$– | 89 |
| IIIa-22-50 | CH$_3$CH$_2$ | H | (CH$_3$)$_2$CHC(CH$_3$)=CHCH$_2$C(CH$_3$)=CH– | 78 |
| IIIa-22-51 | CH$_3$CH$_2$ | H | CH$_3$CH$_2$CHCH$_2$CH$_2$CH$_2$CH$_2$– (CH$_3$ branch) | 78 |
| IIIa-22-52 | CH$_3$CH$_2$ | H | CH=CHCH$_2$– (furan-2-yl) | 83 |
| IIIa-22-53 | CH$_3$CH$_2$ | H | HOCH$_2$(CH$_2$)$_3$CH$_2$– | 78 |
| IIIa-22-54 | CH$_3$CH$_2$ | H | (3,4-dihydro-2H-pyran-2-yl)-CH$_2$– | 78 |

TABLE 13-continued
| Compound No. | $R_1$ | $R_3$ | $R_5$ | % Inhibition of Ulcer 50 mg/kg i.p. (%) |
|---|---|---|---|---|
| IIIa-22-55 | $CH_3CH_2$ | H | 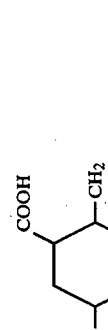 | 78 |
| IIIa-22-56 | $CH_3CH_2$ | H |  | 78 |
| IIIa-22-57 | $CH_3CH_2$ | H |  | 78 |
| IIIa-22-58 | $CH_3CH_2$ | H | 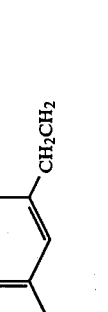 | 89 |
| IIIa-22-59 | $CH_3CH_2$ | H | 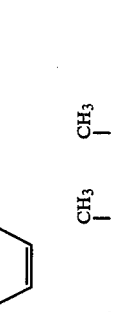 | 83 |
| IIIa-22-60 | $CH_3CH_2$ | H |  | 83 |
| IIIa-22-61 | $CH_3CH_2$ | H |  | 83 |

TABLE 13-continued
| Compound No. | $R_1$ | $R_3$ | $R_5$ | % Inhibition of Ulcer 50 mg/kg i.p. (%) |
|---|---|---|---|---|
| IIIa-22-62 | $CH_3CH_2$ | H | 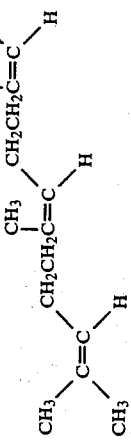 | 83 |
| IIIa-22-63 | $CH_3CH_2$ | H |  | 83 |
| IIIa-22-64 | $CH_3CH_2$ | H | 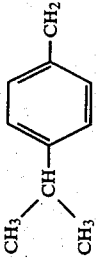 | 78 |
| IIIa-22-65 | $CH_3CH_2$ | H | 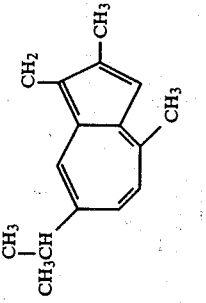 | 72 |
| IIIa-22-66 | $CH_3CH_2$ | H | 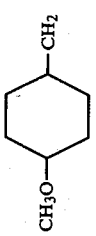 | 78 |
| IIIa-22-67 | $CH_3CH_2$ | H | 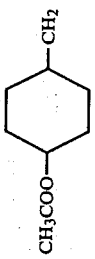 | 78 |
| IIIa-22-68 | $CH_3CH_2$ | H | 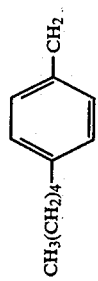 | 78 |

TABLE 13-continued

| Compound No. | $R_1$ | $R_3$ | $R_5$ | % Inhibition of Ulcer 50 mg/kg i.p. (%) |
|---|---|---|---|---|
| IIIa-22-69 | $CH_3CH_2$ | H | $CH_3CH_2CH_2CH=CH$—⟨C_6H_4⟩—$CH_2$ | 72 |
| IIIa-22-70 | $CH_3CH_2$ | H | $(CH_3)_2CH$ | 83 |
| IIIa-22-72 | $CH_3CH_2$ | H | $(CH_3)_2C=CHCH_2$ | 94 |
| IIIa-22-73 | $CH_3CH_2$ | H | $CH_3$—C(OCH_3)(CH_3)—$CH_2CH_2$ | 83 |
| IIIa-22-74 | $CH_3$ | H | $CH_3(CH_2)_2CH_2$ | 100 |
| IIIa-22-75 | $CH_3CH_2$ | H | $CH_3(CH_2)_2CH_2$ | 100 |
| IIIa-22-76 | $CH_3(CH_2)_2CH_2$ | H | $CH_3(CH_2)_2CH_2$ | 94 |
| IIIa-22-77 | $(CH_3)_2CHCH_2CH_2$ | H | $CH_3(CH_2)_2CH_2$ | 94 |
| IIIa-22-78 | $CH_3(CH_2)_{16}CH_2$ | H | $CH_3(CH_2)_2CH_2$ | 72 |
| IIIa-22-79 | $ClCH_2CH_2$ | H | $CH_3(CH_2)_2CH_2$ | 94 |
| IIIa-22-80 | $HC(CH_2)_7CH_3$ =$HC(CH_2)_7CH_2$ | H | $CH_3(CH_2)_2CH_2$ | 72 |
| IIIa-22-81 | adamantyl | H | $CH_3(CH_2)_2CH_2$ | 78 |
| IIIa-22-82 | $C_6H_5CH_2$ | H | $CH_3(CH_2)_2CH_2$ | 72 |
| IIIa-23-83 | cyclopropyl | H | $CH_3(CH_2)_2CH_2$ | 83 |

TABLE 13-continued

| Compound No. | R₁ | R₃ | R₅ | % Inhibition of Ulcer 50 mg/kg i.p. (%) |
|---|---|---|---|---|
| IIIa-22-84 | cyclohexyl-CH₂ | H | CH₃(CH₂)₂CH₂ | 83 |
| IIIa-22-85 | phenyl-CH₂CH₂ | H | CH₃(CH₂)₂CH₂ | 89 |
| IIIa-22-86 | 2,3-dihydrofuran-2-yl-CH₂ | H | CH₃(CH₂)₂CH₂ | 83 |
| IIIa-22-87 | tetrahydrofuran-2-yl-CH₂ | H | CH₃(CH₂)₂CH₂ | 83 |
| IIIa-22-88 | tetrahydropyran-2-yl-CH₂CH₂ | H | CH₃(CH₂)₂CH₂ | 89 |
| IIIa-22-89 | 1-acetylpiperidin-4-yl-CH₂ | H | CH₃(CH₂)₂CH₂ | 83 |
| IIIa-22-90 | naphthalen-2-yl-CH₂ | H | CH₃(CH₂)₂CH₂ | 78 |
| IIIa-22-91 | naphthalen-2-yl-CH₂CH₂ | H | CH₃(CH₂)₂CH₂ | 83 |
| IIIa-22-92 | BrCH₂CH₂CH₂ | H | CH₃(CH₂)₂CH₂ | 94 |

TABLE 13-continued

| Compound No. | $R_1$ | $R_3$ | $R_5$ | % Inhibition of Ulcer 50 mg/kg i.p. (%) |
|---|---|---|---|---|
| IIIa-22-93 | $CH_3CH_2CCH_2$ with =O | H | $CH_3(CH_2)_2CH_2$ | 94 |
| IIIa-22-94 | 4-$CH_3$-$C_6H_4$-$CH_2$ | H | $CH_3(CH_2)_2CH_2$ | 83 |
| IIIa-22-95 | 4-($CH_3)_2CHCH_2CH_2$-$C_6H_4$-$CH_2$ | H | $CH_3(CH_2)_2CH_2$ | 78 |
| IIIa-22-96 | 4-$CH_3O$-$C_6H_4$-$CH_2$ | H | $CH_3(CH_2)_2CH_2$ | 78 |
| IIIa-22-97 | 4-[($CH_3)_2CHCH_2CH_2O$]-$C_6H_4$-$CH_2$ | H | $CH_3(CH_2)_2CH_2$ | 72 |
| IIIa-22-98 | $CH_3O$-$CH(CH_3)CH_2CH_2$ | H | $CH_3(CH_2)_2CH_2$ | 89 |
| IIIa-22-99 | $CH_3(CH_2)_4O$-$CH(CH_3)CH_2CH_2$ | H | $CH_3(CH_2)_2CH_2$ | 83 |
| IIIa-22-100 | $CH_3COO$-$CH(CH_3)CH_2CH_2$ | H | $CH_3(CH_2)_2CH_2$ | 89 |

TABLE 13-continued

| Compound No. | $R_1$ | $R_3$ | $R_5$ | % Inhibition of Ulcer 50 mg/kg i.p. (%) |
|---|---|---|---|---|
| IIIa-22-101 | $CH_3(CH_2)_3CH_2COOCH(CH_3)CH_2CH_2$ | H | $CH_3(CH_2)_2CH_2$ | 83 |
| IIIa-22-102 | $(CH_3)_2C=CHCH_2CH_2C(CH_3)=CHCH_2$ | | $CH_3(CH_2)_2CH_2$ | 78 |
| IIIa-22-103 | $CH_3CH_2CH(CH_3)(CH_2)_4CH_2$ | H | $CH_3(CH_2)_2CH_2$ | 89 |
| IIIa-22-104 | 2,5-dihydrofuran-2-yl-CH=CHCH$_2$ | H | $CH_3(CH_2)_2CH_2$ | 89 |
| IIIa-22-105 | cyclooctyl-CH$_2$ | H | $CH_3(CH_2)_2CH_2$ | 94 |
| IIIa-22-106 | cyclopentyl-CH$_2$CH$_2$CH$_2$ | H | $CH_3(CH_2)_2CH_2$ | 83 |
| IIIa-22-107 | 4-methylphenyl-CH$_2$CH$_2$ | H | $CH_3(CH_2)_2CH_2$ | 72 |
| IIIa-22-108 | $CH_3CH(CH_3)CH(CH_2)_3CH(CH_3)(CH_2)_3CH(CH_3)CH_2CH_2$ | H | $CH_3(CH_2)_2CH_2$ | |

TABLE 13-continued

| Compound No. | R$_1$ | R$_3$ | R$_5$ | % Inhibition of Ulcer 50 mg/kg i.p. (%) |
|---|---|---|---|---|
| IIIa-22-109 | $CH_3\text{-}CH_2CH_2C(CH_3)=CH\text{-}CH_2CH_2\text{-}C(CH_3)=CH\text{-}CH_2CH_2\text{-}C(CH_3)=CH\text{-}$ (farnesyl-type) | H | CH$_3$(CH$_2$)$_2$CH$_2$ | 72 |
| IIIa-22-110 | 4-isopropylbenzyl (CH$_3$)$_2$CH-C$_6$H$_4$-CH$_2$- | H | CH$_3$(CH$_2$)$_2$CH$_2$ | 78 |
| IIIa-22-111 | bornyl/pinanyl group | H | CH$_3$(CH$_2$)$_2$CH$_2$ | 78 |
| IIIa-22-112 | CH$_3$(CH$_2$)$_4$-C$_6$H$_4$-CH$_2$- | H | CH$_3$(CH$_2$)$_2$CH$_2$ | 78 |
| IIIa-22-113 | CH$_3$CH$_2$CH$_2$CH=CH-C$_6$H$_4$-CH$_2$- | H | CH$_3$(CH$_2$)$_2$CH$_2$ | 78 |
| IIIa-22-114 | (CH$_3$)$_2$CH- | H | CH$_3$(CH$_2$)$_2$CH$_2$ | 94 |
| IIIa-23-1 | (CH$_3$)$_2$CHCH$_2$- | CH$_3$CO | CH$_3$CH$_2$ | 44 |

TABLE 13-continued

| Compound No. | $R_1$ | $R_3$ | $R_5$ | % Inhibition of Ulcer 50 mg/kg i.p. (%) |
|---|---|---|---|---|
| IIIa-23-2 | $CH_3CH_2$ | $CH_3CO$ | $CH_3$–$CHCH_2CH_2$–$CH_3$ | 44 |
| IIIa-23-3 | $CH_3CH_2$ | $CH_3CO$ | $CH_3(CH_2)_{16}CH_2$ | 44 |
| IIIa-23-4 | $CH_3CH_2$ | $CH_3CO$ | $HC(CH_2)_7CH_3$ $\|\|$ $HC(CH_2)_7CH_2$ | 44 |
| IIIa-23-5 | $CH_3(CH_2)_{16}CH_2$ | $CH_3CO$ | tetrahydrofuran-2-yl-$CH_2$ | 56 |
| IIIa-23-6 | $CH_3CH_2$ | $CH_3CO$ | $CH_3O$–$CHCH_2CH_2$–$CH_3$ | 56 |
| IIIa-23-7 | $CH_3CH_2$ | $CH_3CO$ | $CH_3$–C$_6$H$_4$–$CH_2$ | 56 |
| IIIa-23-8 | $CH_3CH_2$ | $CH_3CO$ | $CH_3$–$CHCH_2CH_2O$–C$_6$H$_4$–$CH_2$ / $CH_3$ | 44 |
| IIIa-23-9 | cyclohexyl-$CH_2$ | $CH_3CH_2CO$ | $CH_3CH_2$ | 56 |
| IIIa-23-10 | 2,5-dihydrofuran-2-yl-$CH_2$ | $CH_3CH_2CH_2CO$ | $CH_3CH_2CH_2CH_2$ | 56 |
| IIIa-23-11 | $CH_3$ | $CH_3CH_2O$ | $CH_3CH_2$ | 56 |
| IIIa-24-1 | $CH_3CH_2$ | $CH_3$ | $CH_3CH_2$ | 56 |
| IIIa-24-2 | $CH_3CH_2$ | $CH_3CH_2$ | $CH_3CH_2$ | 56 |

TABLE 13-continued

| Compound No. | $R_1$ | $R_3$ | $R_5$ | % Inhibition of Ulcer 50 mg/kg i.p. (%) |
|---|---|---|---|---|
| IIIa-24-3 | $CH_3CH_2$ | $CH_3CH_2$ | $CH_3\text{-}CHCH_2CH_2\text{-}$ with $CH_3$ branch | 56 |
| IIIa-24-4 | $CH_3(CH_2)_5CH_2$ | $CH_3CH_2$ | $CH_3(CH_2)_{16}CH_2$ | 44 |
| IIIa-24-5 | $CH_3CH_2$ | $CH_3CH_2$ | $HC(CH_2)_7CH_3$ $\|\|$ $HC(CH_2)_7CH_2$ | 44 |
| IIIa-24-6 | $CH_3CH_2$ | $CH_3$ | tetrahydrofuran-2-yl-$CH_2$ | 56 |
| IIIa-24-7 | $CH_3CH_2$ | $CH_3$ | $CH_3O\text{-}CHCH_2CH_2\text{-}$ with $CH_3$ branch | 56 |
| IIIa-24-8 | $CH_3CH_2$ | $CH_3CH_2CH_2CH_2$ | 4-$CH_3$-$C_6H_4$-$CH_2$ | 56 |
| IIIa-24-9 | $CH_3CH_2$ | $CH_3$ | $CH_3\text{-}CHCH_2O\text{-}C_6H_4\text{-}CH_2$ with $CH_3$ branch | 56 |
| IIIa-24-10 | $CH_3$ | $CH_3CH_2CH_2CH_2$ | $CH_3CH_2CH_2CH_2$ | 56 |
| IIIa-24-11 | $C_6H_5CH_2$ | $(CH_3)_2CH$ | $CH_3CH_2CH_2CH_2$ | 44 |
| IIIa-24-12 | $C_6H_{11}CH_2$ | $(CH_3)_2CH$ | $CH_3CH_2CH_2CH_2$ | 44 |

TABLE 13-continued

| Compound No. | R₁ | R₃ | R₅ | % Inhibition of Ulcer 50 mg/kg i.p. (%) |
|---|---|---|---|---|
| IIIa-24-13 | 2-naphthyl-CH₂ | CH₃ | CH₃CH₂CH₂CH₂ | 44 |
| IIIa-24-14 | (tetrahydropyran-2-yl)-CH₂ | CH₃ | CH₃CH₂CH₂CH₂ | 44 |
| IIIa-24-15 | CH₂(CH₂)₃CH₂COO-CH(CH₃)CH₂CH₂- | CH₃ | CH₃CH₂CH₂CH₂ | 44 |
| IIIa-24-16 | CH₃(CH₂)₂CH₂ | CH₃ | CH₃CH₂ | 56 |
| IIIa-25-1 | H | CH₃(CH₂)₂CH₂ | CH₃CH₂ | 66 |
| IIIa-25-2 | H | CH₃(CH₂)₂CH₂ | (CH₃)₂CHCH₃ | 66 |
| IIIa-25-3 | H | CH₃(CH₂)₂CH₂ | CH₃(CH₂)₁₆CH₂ | 56 |
| IIIa-25-4 | CH₃(CH₂)₅CH₂ | CH₃(CH₂)₁₆CH₂ | HC(CH₂)₇CH₃ =HC(CH₂)₇CH₃ | 56 |
| IIIa-25-5 | CH₃(CH₂)₂CH₂ | CH₃(CH₂)₂CH₂ | (tetrahydrofuran-2-yl)-CH₂ | 66 |
| IIIa-25-6 | CH₃(CH₂)₂CH₂ | CH₃(CH₂)₂CH₂ | CH₃O-CH(CH₃)CH₂CH₂- | 66 |
| IIIa-25-7 | CH₃(CH₂)₂CH₂ | CH₃(CH₂)₂CH₂ | 4-methylbenzyl (p-CH₃-C₆H₄-CH₂) | 66 |

TABLE 13-continued

| Compound No. | R₁ | R₃ | R₅ | % Inhibition of Ulcer 50 mg/kg i.p. (%) |
|---|---|---|---|---|
| IIIa-25-8 | H | $CH_3(CH_2)_2CH_2$ | $CH_3$—CHCH$_2$CH$_2$O—⟨C$_6$H$_4$⟩—CH$_2$, $CH_3$ | 66 |
| IIIa-25-9 | H | $CH_3$ | $CH_3CH_2$ | 66 |
| IIIa-25-10 | H | $CH_3$ | $CCl_3CH_2$ | 66 |
| IIIa-26-1 | $CH_3CO$ | $CH_3CH_2CH_2CH_2$ | $CH_3CH_2$ | 56 |
| IIIa-26-2 | $CH_3CO$ | $CH_3CH_2CH_2CH_2$ | $(CH_3)_2CHCH_3$ | 44 |
| IIIa-26-3 | $CH_3CO$ | $CH_3CH_2CH_2CH_2$ | $CH_3(CH_2)_{16}CH_2$ |  |
| IIIa-26-4 | $CH_3CO$ | $CH_3CH_2CH_2CH_2$ | tetrahydrofuryl-CH$_2$ | 56 |
| IIIa-26-5 | $CH_3(CH_2)_{16}CO$ | $CH_3CH_2CH_2CH_2$ | $CH_3CH_2$ | 56 |
| IIIa-26-6 | $CH_3(CH_2)_{16}CO$ | $CH_3CH_2CH_2CH_2$ | $HC(CH_2)_7CH_3$ ═ $HC(CH_2)_7CH_2$ | 44 |
| IIIa-26-7 | $CH_3(CH_2)_{16}CO$ | $CH_3CH_2CH_2CH_2$ | $CH_3O$—CHCH$_2$CH$_2$, $CH_3$ | 56 |
| IIIa-26-8 | $CH_3(CH_2)_{16}CO$ | $CH_3CH_2CH_2CH_2$ | ⟨C$_6$H$_4$⟩—CH$_2$, $CH_3$ | 44 |
| IIIa-26-9 | $(CH_3)_2CHCO$ | $CH_3$ | $CH_3CH_2$ | 56 |
| IIIa-27-1 | H | H | $CH_3$ | 100 |
| IIIa-27-2 | H | H | $CH_3$—CH—$CH_3$ | 94 |
| IIIa-28-1 | H | $CH_3CO$ | $CH_3$ | 66 |
| IIIa-28-2 | H | $(CH_3)_2CHCH_2CO$ | $CH_3$ | 66 |
| IIIa-28-3 | H | $CCl_3CO$ | $CH_3$ | 66 |
| IIIa-28-4 | H | $CH_3CO$ | $(CH_3)_2CO$ | 56 |
| IIIa-28-5 | H | $CH_3(CH_2)_{16}CO$ | $(CH_3)_2CO$ | 56 |

TABLE 13-continued

| Compound No. | R$_1$ | R$_3$ | R$_5$ | % Inhibition of Ulcer 50 mg/kg i.p. (%) |
|---|---|---|---|---|
| IIIa-29-1 | CH$_3$CO | CH$_3$CO | CH$_3$ | 56 |
| IIIa-29-2 | CH$_3$CO | CH$_3$CO | CH(CH$_3$)$_2$ | 56 |
| IIIa-30-1 | CH$_3$CO | H | CH$_3$ | 78 |
| IIIa-30-2 | (CH$_3$)$_2$CHCO | H | CH(CH$_3$)$_2$ | 78 |
| IIIa-31-1 | CH$_3$ | H | CH$_3$ | 94 |
| IIIa-31-2 | CH$_3$CH$_2$ | H | CH$_3$ | 94 |
| IIIa-31-3 | CH$_3$(CH$_2$)$_{16}$CH$_2$ | H | CH$_3$ | 78 |
| IIIa-31-4 | (CH$_3$)$_2$CHCH$_2$CH$_2$ | H | CH$_3$ | 89 |
| IIIa-31-5 | HC(CH$_2$)$_7$CH$_3$ =  HC(CH$_2$)$_7$CH$_2$ | H | CH$_3$ | 78 |
| IIIa-31-6 | CH$_3$ | H | CH(CH$_3$)$_2$ | 78 |
| IIIa-31-7 | CH$_3$CH$_2$ | H | CH(CH$_3$)$_2$ | 83 |
| IIIa-31-8 | CH$_3$(CH$_2$)$_{16}$CH$_2$ | H | CH(CH$_3$)$_2$ | 72 |
| IIIa-31-9 | (CH$_3$)$_2$CHCH$_2$CH$_2$ | H | CH(CH$_3$)$_2$ | 83 |

TABLE 13-continued

| Compound No. | $R_1$ | $R_3$ | $R_5$ | % Inhibition of Ulcer 50 mg/kg. i.p. (%) |
|---|---|---|---|---|
| IIIa-31-10 | HC(CH₂)₇CH₃ ‖ HC(CH₂)₇CH₂ | H | CH₃—CH—CH₃ | 72 |
| IIIa-31-11 | —CH₂—C₆H₅ | H | CH₃ | 83 |
| IIIa-31-12 | tetrahydropyran-2-yl-CH₂CH₂ | H | CH₃ | 89 |
| IIIa-31-13 | adamantyl-CH₂ | H | CH₃ | 89 |
| IIIa-31-14 | CH₃—CH—CH₃ | H | CH₃ | 94 |
| IIIa-32-1 | CH₃CH₂ | CH₃CO | CH₃ | 56 |
| IIIa-32-2 | CH₃CH₂ | (CH₃)₂CHCO | CH₃ | 44 |
| IIIa-32-3 | CH₃CH₂ | CH₃CO | CH₃—CH—CH₃ | 44 |
| IIIa-33-1 | CH₃ | CH₃CH₂CH₂CH₂ | CH₃ | 56 |
| IIIa-33-2 | CH₃ | CH₃CH₂CH₂CH₂ | CH₃—CH—CH₃ | 56 |
| IIIa-33-3 | CH₃(CH₂)₂CH₂ | CH₃CH₂CH₂CH₂ CH₃ | CH₃ CH₃ | 56 |
| IIIa-34-1 | H | | | 66 |

TABLE 13-continued

| Compound No. | R₁ | R₃ | R₅ | % Inhibition of Ulcer 50 mg/kg i.p. (%) |
|---|---|---|---|---|
| IIIa-34-2 | H | CH₃(CH₂)₁₇ | CH₃–CH(–CH₃) | 56 |
| IIIa-34-3 | H | CH₃ | CH₃–CH(–CH₃) | 66 |
| IIIa-35-1 | CH₃CO | CH₃ | CH₃ | 56 |
| IIIa-35-2 | CH₃CO | CH₃ | CH₃–CH(–CH₃) | 44 |

| Compound No. | $R_1$ | $R_3$ | % Inhibition of Ulcer 50 mg/kg i.p. (%) |
|---|---|---|---|
| IVa-1-1 | H | $CH_3CO$ | 44 |
| IVa-1-2 | H | $CH_3CH_2CO$ | 44 |
| IVa-1-3 | H | $CH_3(CH_2)_2CO$ | 44 |
| IVa-1-4 | H | $(CH_3)_2CHCO$ | 44 |
| IVa-1-5 | H | $(CH_3)_2CHCH_2CO$ | 44 |
| IVa-1-6 | H | $CH_3(CH_2)_3CO$ | 44 |
| IVa-1-7 | H | $CH_3(CH_2)_4CO$ | 44 |
| IVa-1-8 | H | $CH_3(CH_2)_5CO$ | 33 |
| IVa-1-9 | H | $CH_3(CH_2)_6CO$ | 33 |
| IVa-1-10 | H | $CH_3(CH_2)_{10}CO$ | 33 |
| IVa-1-11 | H | $CH_3(CH_2)_{16}CO$ | 33 |
| IVa-1-12 | H | $CCl_3CO$ | 44 |
| IVa-1-13 | H | $HC(CH_2)_7CH_3$<br>$\|\|$<br>$HC(CH_2)_7CO$ | 33 |
| IVa-1-14 | H | 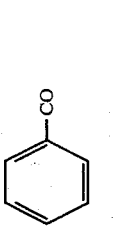 | 33 |
| IVa-1-15 | H | 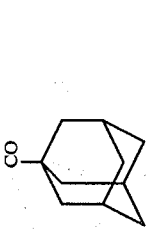 | 33 |
| IVa-1-16 | H | 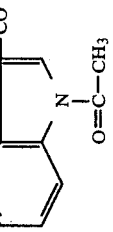 | 33 |
| IVa-1-17 | H |  | 33 |
| IVa-1-18 | H |  | 33 |

-continued
| Compound No. | R₁ | R₃ | % Inhibition of Ulcer 50 mg/kg i.p. (%) |
|---|---|---|---|
| IVa-1-19 | H | 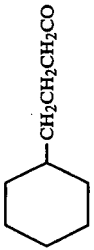 CH₂CH₂CH₂CO-cyclohexyl | 44 |
| IVa-1-20 | H | 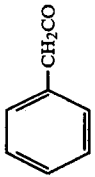 CH₂CO-phenyl | 44 |
| IVa-1-21 | H | 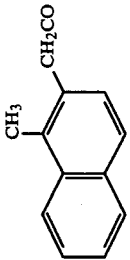 1-CH₃, 2-CH₂CO-naphthyl | 44 |
| IVa-1-22 | H |  CO-(2,5-dihydrofuran) | 33 |
| IVa-1-23 | H | 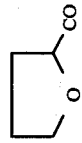 CO-(tetrahydrofuran) | 33 |
| IVa-1-24 | H | 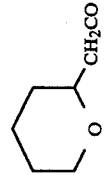 CH₂CO-(tetrahydropyran) | 44 |
| IVa-1-25 | H |  CO-(2,5-dihydrothiophene) | 33 |
| IVa-1-26 | H | 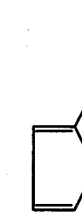 CH₂CH₂CH₂CO-(2,5-dihydrothiophene) | 33 |

-continued

| Compound No. | R₁ | R₃ | % Inhibition of Ulcer 50 mg/kg i.p. (%) |
|---|---|---|---|
| IVa-1-27 | H | (tetrazole with N-CH₃ and CO) | 33 |
| IVa-1-28 | H | (N-acetyl pyrrole with CO) | 33 |
| IVa-1-29 | H | (N-methyl pyrrole with CO) | 33 |
| IVa-1-30 | H | (6-methoxyquinoline-3-CO) | 33 |
| IVa-1-31 | H | BrCH₂CH₂CH₂CO | 44 |
| IVa-1-32 | H | CH₃CH₂C(=O)—CO | 44 |
| IVa-1-33 | H | (2-oxocyclohexyl-CO) | 33 |
| IVa-1-34 | H | CH₃COO—C₆H₄—CO | 33 |

-continued

| Compound No. | R₁ | R₃ | % Inhibition of Ulcer 50 mg/kg i.p. (%) |
|---|---|---|---|
| IVa-1-35 | H | 4-HO-C₆H₄-CO- | 33 |
| IVa-1-36 | H | CH₂COOCH₂CH₃ / CH₂CO | 44 |
| IVa-1-37 | H | CH₂COOH / CH₂CO | 44 |
| IVa-1-38 | H | 4-CH₃-C₆H₄-CO- | 33 |
| IVa-1-39 | H | (CH₃)₂CHCH₂CH₂-(4-C₆H₄)-CO- | 33 |
| IVa-1-40 | H | 4-CH₃O-C₆H₄-CO- | 33 |
| IVa-1-41 | H | (CH₃)₂CHCH₂CH₂O-(4-C₆H₄)-CO- | 33 |
| IVa-1-42 | H | CH₃O-CH(CH₃)-CH₂CH₂-CHCH₂CO- | 44 |
| IVa-1-43 | H | CH₃(CH₂)₄O-CH(CH₃)-CHCH₂CO- | 44 |

-continued

| Compound No. | R₁ | R₃ | % Inhibition of Ulcer 50 mg/kg i.p. (%) |
|---|---|---|---|
| IVa-1-44 | H | $CH_3SCH_2CO$ | 44 |
| IVa-1-45 | H | $CH_3(CH_2)_3SCH_2CO$ | 44 |
| IVa-1-46 | H | 4-$CH_3S$-C₆H₄-CO | 33 |
| IVa-1-47 | H | 4-$CH_3(CH_2)_3CH_2S$-C₆H₄-CO | 33 |
| IVa-1-48 | H | $CH_3COO$-CH($CH_3$)-$CH_2CO$ | 44 |
| IVa-1-49 | H | $CH_3(CH_2)_3CH_2COO$-CH($CH_3$)-$CH_2CO$ | 33 |
| IVa-1-50 | H | 4-$CH_3OOC$-C₆H₄-CO | 33 |
| IVa-1-51 | H | 4-$CH_3(CH_2)_3CH_2OOC$-C₆H₄-CO | 33 |
| IVa-1-52 | H | $CH\equiv C-CO$ | 44 |
| IVa-1-53 | H | 4-$(CH_3)_2CH$-$CH_2CH_2$-C₆H₄-CH($CH_3$)-$CHO$ | 33 |

-continued
| Compound No. | R₁ | R₃ | % Inhibition of Ulcer 50 mg/kg i.p. (%) |
|---|---|---|---|
| IVa-1-54 | H | 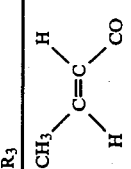 | 44 |
| IVa-1-55 | H | 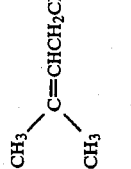 | 33 |
| IVa-1-56 | H | CH₃CH₂CHCH₂CH₂CH₂CH₂CO<br>       \|<br>       CH₃ | 33 |
| IVa-1-57 | H | 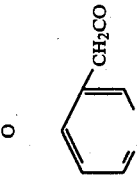 | 44 |
| IVa-1-58 | H | 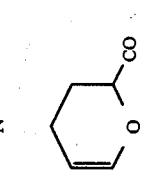 | 44 |
| IVa-1-59 | H | 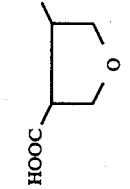 | 33 |
| IVa-1-60 | H | 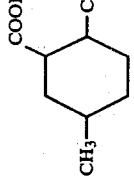 | 33 |
| IVa-1-61 | H |  | 33 |

-continued

| Compound No. | $R_1$ | $R_3$ | % Inhibition of Ulcer 50 mg/kg i.p. (%) |
|---|---|---|---|
| IVa-1-62 | H | cycloheptyl-CO— | 33 |
| IVa-1-63 | H | cyclopentyl-CH$_2$CH$_2$CO— | 44 |
| IVa-1-64 | H | 2-naphthyl-CH$_2$CO— | 44 |
| IVa-1-65 | H | 4-CH$_3$-C$_6$H$_4$-CH$_2$CO— | 44 |
| IVa-1-66 | H | (CH$_3$)$_2$CHCH$_2$CH$_2$CH$_2$CH(CH$_3$)CH$_2$CH$_2$CH$_2$CH$_2$CH$_2$CO— | 33 |
| IVa-1-67 | H | (CH$_3$)$_2$C=CHCH$_2$CH$_2$C(CH$_3$)=CHCH$_2$CH$_2$C(CH$_3$)=CHCH$_2$CH$_2$CO— | 44 |
| IVa-1-68 | H | 4-(CH$_3$OOC)-cyclohexyl-CO— | 33 |
| IVa-1-69 | H | 4-((CH$_3$)$_2$CH)-C$_6$H$_4$-CO— | 33 |

-continued

| Compound No. | $R_1$ | $R_3$ | % Inhibition of Ulcer 50 mg/kg i.p. (%) |
|---|---|---|---|
| IVa-1-70 | H | 2,4,8-trimethylazulenyl-1-carbonyl (CH₃ groups at 2,4,8 positions) | 33 |
| IVa-1-71 | H | norbornenyl-CO | 33 |
| IVa-1-72 | H | camphor-type bicyclic ketone-CO | 33 |
| IVa-1-73 | H | 4-methoxycyclohexyl-CO | 33 |
| IVa-1-74 | H | 4-(CH₃COO)cyclohexyl-CO | 33 |
| IVa-1-75 | H | tetrazol-1-yl-CH₂CO | 33 |
| IVa-1-76 | H | 4-(CH₃(CH₂)₄)phenyl-CO | 33 |

-continued

| Compound No. | R₁ | R₃ | % Inhibition of Ulcer 50 mg/kg i.p. (%) |
|---|---|---|---|
| IVa-1-77 | H | $CH_3CH_2CH_2CH=CH$—C₆H₄—CO | 33 |
| IVa-1-78 | H | $HOCH_2(CH_2)_3CO$ | 33 |
| IVa-1-79 | H | cyclopropyl-$CH_2CO$ | 33 |
| IVa-1-80 | H | $Br(CH_3)C=C(CH_3)CO$ | 33 |
| IVa-1-81 | H | $(CH_3)_2C=CHCO$ | 33 |
| IVa-1-82 | H | $CH_3-C(SCH_3)(CH_3)-CH_2CO$ | 33 |
| IVa-1-83 | H | $CH_3-C(OCH_3)(CH_3)-CH_2CO$ | 33 |
| IVa-2-1 | $CH_3CO$ | $CH_3CO$ | 33 |
| IVa-2-2 | $CH_3CH_2CO$ | $CH_3CO$ | 33 |
| IVa-2-3 | $CH_3(CH_2)_{16}CO$ | C₆H₅—CO | 33 |
| IVa-2-4 | $CH_3CO$ | $CH_3(CH_2)_{16}CO$ | 33 |
| IVa-3-1 | $CH_3CO$ | H | 44 |
| IVa-3-2 | $CH_3CH_2CO$ | H | 44 |
| IVa-3-3 | $CH_3(CH_2)_2CO$ | H | 44 |
| IVa-3-4 | $CH_3(CH_2)_3CO$ | H | 33 |
| IVa-3-5 | $CH_3(CH_2)_4CO$ | H | 33 |
| IVa-3-6 | $CH_3(CH_2)_5CO$ | H | 33 |
| IVa-3-7 | $CH_3(CH_2)_6CO$ | H | 33 |
| IVa-3-8 | $CH_3(CH_2)_{10}CO$ | H | 33 |
| IVa-3-9 | $CH_3(CH_2)_{16}CO$ | H | 33 |
| IVa-3-10 | $(CH_3)_2CHCO$ | H | 44 |
| IVa-3-11 | $(CH_3)_2CHCH_2CO$ | H | 44 |

-continued

| Compound No. | R₁ | R₃ | % Inhibition of Ulcer 50 mg/kg i.p. (%) |
|---|---|---|---|
| IVa-3-12 | HC(CH₂)₇CH₃<br>‖<br>HC(CH₂)₇CO | H | 33 |
| IVa-3-13 | CCl₃CO | H | 44 |
| IVa-3-14 | CH₃<br>\|<br>C=CHCH₂C=C<br>\|            \|<br>CH₃         CH₃<br>(with H and CO on terminal C) | H | 33 |
| IVa-3-15 | cyclopentyl-CH₂CH₂CO | H | 33 |
| IVa-3-16 | CH₃O-C₆H₄-CO (para) | H | 33 |
| IVa-3-17 | CH₃O<br>\|<br>CHCH₂CO<br>\|<br>CH₃ | H | 33 |
| IVa-3-18 | CH₃    H<br>  \\   /<br>  C=C<br>  /   \\<br>  H     CO | H | 33 |
| IVa-4-1 | CH₃ | H | 44 |
| IVa-4-2 | CH₃CH₂ | H | 44 |
| IVa-4-3 | CH₃(CH₂)₂CH₂ | H | 44 |
| IVa-4-4 | (CH₃)₂CHCH₂CH₂ | H | 44 |
| IVa-4-5 | CH₃(CH₂)₁₆CH₂ | H | 33 |
| IVa-4-6 | ClCH₂CH₂ | H | 44 |
| IVa-4-7 | HC(CH₂)₇CH₃<br>‖<br>HC(CH₂)₇CH₂ | H | 33 |

-continued

| Compound No. | R₁ | R₃ | % Inhibition of Ulcer 50 mg/kg i.p. (%) |
|---|---|---|---|
| IVa-4-8 | 1-adamantyl | H | 33 |
| IVa-4-9 | benzyl (–CH₂–C₆H₅) | H | 33 |
| IVa-4-10 | cyclopropyl | H | 33 |
| IVa-4-11 | cyclohexyl–CH₂– | H | 33 |
| IVa-4-12 | –CH₂CH₂–C₆H₅ | H | 44 |
| IVa-4-13 | 2-furyl–CH₂– | H | 33 |
| IVa-4-14 | tetrahydrofuran-2-yl–CH₂– | H | 33 |
| IVa-4-15 | tetrahydropyran-2-yl–CH₂CH₂– | H | 44 |

-continued

| Compound No. | R₁ | R₃ | % Inhibition of Ulcer 50 mg/kg i.p. (%) |
|---|---|---|---|
| IVa-4-16 | CH₃CON(cyclohexyl)-CH₂– | H | 33 |
| IVa-4-17 | 2-naphthyl-CH₂– | H | 33 |
| IVa-4-18 | 2-naphthyl-CH₂CH₂– | H | 33 |
| IVa-4-19 | BrCH₂CH₂CH₂– | H | 44 |
| IVa-4-20 | CH₃CH₂CCH₂– (O=) | H | 44 |
| IVa-4-21 | 4-CH₃-C₆H₄-CH₂– | H | 33 |
| IVa-4-22 | (CH₃)₂CHCH₂-C₆H₄-CH₂– | H | 33 |
| IVa-4-23 | 4-CH₃O-C₆H₄-CH₂– | H | 33 |
| IVa-4-24 | (CH₃)₂CHCH₂O-C₆H₄-CH₂– | H | 33 |

-continued

| Compound No. | R₁ | R₃ | % Inhibition of Ulcer 50 mg/kg i.p. (%) |
|---|---|---|---|
| IVa-4-25 | CH₃O-CH(CH₃)-CH₂CH₂CH₂- | H | 33 |
| IVa-4-26 | CH₃(CH₂)₄O-CH(CH₃)-CHCH₂CH₂- | H | 33 |
| IVa-4-27 | CH₃COO-CH(CH₃)-CHCH₂CH₂- | H | 33 |
| IVa-4-28 | CH₃(CH₂)₃CH₂COO-CH(CH₃)-CHCH₂CH₂- | H | 33 |
| IVa-4-29 | (CH₃)₂C=CHCH₂C(CH₃)=CH-CH₂ / H | H | 33 |
| IVa-4-30 | CH₃CH₂CH(CH₃)(CH₂)₄CH₂- | H | 33 |
| IVa-4-31 | CH=CHCH₂- (dihydrofuranyl) | H | 33 |
| IVa-4-32 | cycloheptyl-CH₂- | H | 33 |
| IVa-4-33 | cyclopentyl-CH₂CH₂CH₂- | H | 44 |

-continued
| Compound No. | R₁ | R₃ | % Inhibition of Ulcer 50 mg/kg i.p. (%) |
|---|---|---|---|
| IVa-4-34 | 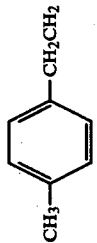 | H | 33 |
| IVa-4-35 | $CH_3CH(CH_3)_3CH(CH_3)_3CH(CH_3)_3CH_2$ | H | 33 |
| IVa-4-36 |  | H | 33 |
| IVa-4-37 | 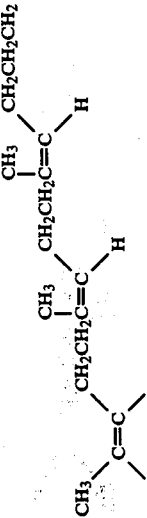 | H | 33 |
| IVa-4-38 | 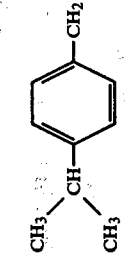 | H | 33 |
| IVa-4-39 | 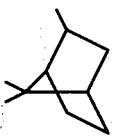 | H | 33 |
| IVa-4-40 | 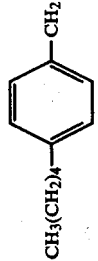 | H | 33 |

-continued

| Compound No. | R₁ | R₃ | % Inhibition of Ulcer 50 mg/kg i.p. (%) |
|---|---|---|---|
| IVa-4-41 | (CH₃)₂CH | H | 44 |
| IVa-5-1 | CH₃ | CH₃CO | 33 |
| IVa-5-2 | CH₃CH₂ | CH₃CH₂CO | 33 |
| IVa-5-3 | C₆H₅CH₂ | CCl₃CO | 33 |
| IVa-5-4 | HC(CH₂)₇CH₃=HC(CH₂)₇CH₂ | (CH₃)₂CHCO | 33 |
| IVa-6-1 | CH₃ | CH₃ | 33 |
| IVa-6-2 | CH₃CH₂ | CH₃CH₂ | 33 |
| IVa-6-3 | CH₃(CH₂)₂CH₂ | CH₃CH₂ | 33 |
| IVa-6-4 | C₆H₅CH₂ | (CH₃)₂CH | 33 |
| IVa-6-5 | CH₃CH₂ | CH₃(CH₂)₂CH₂ | 33 |
| IVa-7-1 | H | CH₃ | 44 |
| IVa-7-2 | H | CH₃CH₂ | 44 |
| IVa-7-3 | H | (CH₃)₂CHCH₂CH₂ | 44 |
| IVa-7-4 | H | HC(CH₂)₇CH₃=HC(CH₂)₇CH₂ | 33 |
| IVa-7-5 | H | cyclohexyl-CH₂ | 33 |
| IVa-7-6 | H | tetrahydrofuran-2-yl-CH₂ | 33 |

-continued
| Compound No. | $R_1$ | $R_3$ | % Inhibition of Ulcer 50 mg/kg i.p. (%) |
|---|---|---|---|
| IVa-7-7 | H | $CH_3CH_2\overset{O}{\overset{\|}{C}}CH_2$ | 44 |
| IVa-7-8 | H | $(CH_3)_2CHCH_2$ | 33 |
| IVa-8-1 | $CH_3CO$ | $CH_3$ | 33 |
| IVa-8-2 | $CH_3CH_2CO$ | $CH_3$ | 33 |
| IVa-8-3 | $CH_3CO$ | $CH_3CH_2$ | 33 |
| IVa-8-4 | $ClCH_2CO$ |  | 33 |
| IVa-8-5 | $CH_3CO$ | $(CH_3)_2CHCH_2$ | 33 |

| Compound No. | $R_1$ | $R_3$ | $R_5$ | $R_6$ | % Inhibition of Ulcer 50 mg/kg i.p. (%) |
|---|---|---|---|---|---|
| Vb-1-1 | H | H | H | $CH_3$ | 100 |
| Vb-1-2 | H | H | H | $CH_3CH_2$ | 100 |
| Vb-1-3 | H | H | H | $CH_3(CH_2)_2CH_2$ | 100 |
| Vb-1-4 | H | H | H | $(CH_3)_2CHCH_2CH_2$ | 100 |
| Vb-1-5 | H | H | H | $CH_3(CH_2)_{16}CH_2$ | 78 |
| Vb-1-6 | H | H | H | $ClCH_2CH_2$ | 100 |
| Vb-1-7 | H | H | H | $HC(CH_2)_7CH_3$<br>$\parallel$<br>$HC(CH_2)_7CH_2$ | 89 |
| Vb-1-8 | H | H | H |  | 89 |
| Vb-1-9 | H | H | H | 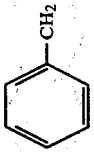 | 89 |
| Vb-1-10 | H | H | H |  | 89 |
| Vb-1-11 | H | H | H | 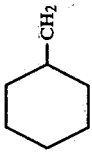 | 89 |
| Vb-1-12 | H | H | H | 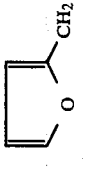 | 94 |
| Vb-1-13 | H | H | H | 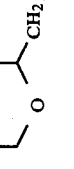 | 89 |
| Vb-1-14 | H | H | H |  | 89 |

-continued
| Compound No. | $R_1$ | $R_3$ | $R_5$ | $R_6$ | % Inhibition of Ulcer 50 mg/kg i.p. (%) |
|---|---|---|---|---|---|
| Vb-1-15 | H | H | H |  | 94 |
| Vb-1-16 | H | H | H |  | 89 |
| Vb-1-17 | H | H | H |  | 89 |
| Vb-1-18 | H | H | H |  | 89 |
| Vb-1-19 | H | H | H | BrCH$_2$CH$_2$CH$_2$ | 100 |
| Vb-1-20 | H | H | H |  | 100 |
| Vb-1-21 | H | H | H |  | 89 |
| Vb-1-22 | H | H | H | 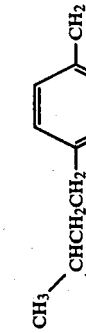 | 89 |
| Vb-1-23 | H | H | H | 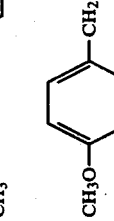 | 89 |

-continued

| Compound No. | $R_1$ | $R_3$ | $R_5$ | $R_6$ | % Inhibition of Ulcer 50 mg/kg i.p. (%) |
|---|---|---|---|---|---|
| Vb-1-24 | H | H | H | $CH_3\text{—}CHCH_2CH_2O\text{—}\langle C_6H_4\rangle\text{—}CH_2$ with $CH_3$ | 89 |
| Vb-1-25 | H | H | H | $CH_3O\text{—}CHCH_2CH_2$ with $CH_3$ | 100 |
| Vb-1-26 | H | H | H | $CH_3(CH_2)_4O\text{—}CHCH_2CH_2$ with $CH_3$ | 94 |
| Vb-1-27 | H | H | H | $CH_3COO\text{—}CHCH_2CH_2$ with $CH_3$ | 94 |
| Vb-1-28 | H | H | H | $CH_3(CH_2)_3CH_2COO\text{—}CHCH_2CH_2$ with $CH_3$ | 94 |
| Vb-1-29 | H | H | H | $CH_3\text{—}C=CHCH_2CH_2C=C\text{—}H$ with $CH_3$ and $CH_3$, $CH_2$ | 89 |
| Vb-1-30 | H | H | H | $CH_3CH_2CH(CH_2)_4CH_2$ with $CH_3$ | 100 |
| Vb-1-31 | H | H | H | $CH=CHCH_2$— (furan) | 100 |
| Vb-1-32 | H | H | H | cycloheptyl-$CH_2$ | 89 |

-continued
| Compound No. | R₁ | R₃ | R₅ | R₆ | % Inhibition of Ulcer 50 mg/kg i.p. (%) |
|---|---|---|---|---|---|
| Vb-1-33 | H | H | H | 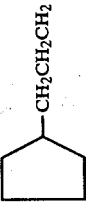 | 100 |
| Vb-1-34 | H | H | H | 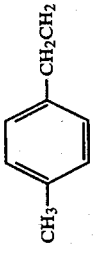 | 89 |
| Vb-1-35 | H | H | H | CH₃—CH(CH₂)₃CH(CH₂)₃CH(CH₂)₂CH₂ with CH₃ branches | 89 |
| Vb-1-36 | H | H | H | 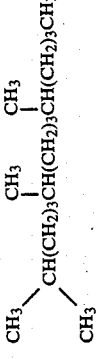 | 89 |
| Vb-1-37 | H | H | H | 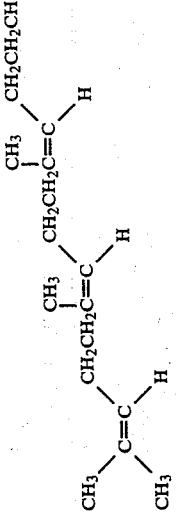 | 83 |
| Vb-1-38 | H | H | H | 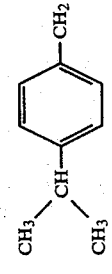 | 83 |
| Vb-1-39 | H | H | H | 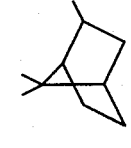 CH₃(CH₂)₄ | 89 |

-continued

| Compound No. | R₁ | R₃ | R₅ | R₆ | % Inhibition of Ulcer 50 mg/kg i.p. (%) |
|---|---|---|---|---|---|
| Vb-1-40 | H | H | H | $CH_3CH_2CH_2CH=CH$–C₆H₄–$CH_2$– | 89 |
| Vb-1-41 | H | H | H | $(CH_3)_2CH$– | 89 |
| Vb-1-42 | H | H | H | $CH_3$–C₆H₄– | 83 |
| Vb-1-43 | H | H | H | 3-methylpiperidin-1-yl ($CH_3$, piperidine N–) | 83 |
| Vb-1-44 | H | H | H | morpholino–$CH_2CH_2$– | 94 |
| Vb-1-45 | H | H | H | piperidino–$CH_2CH_2$– | 94 |
| Vb-2-1 | H | $CH_3CH_2CO$– | H | H | 66 |
| Vb-2-2 | H | cyclopentyl–$CH_2CH_2CO$– | H | H | 56 |
| Vb-2-3 | H | $CH_3$–$CH$=$CH$–CO– | H | H | 66 |

-continued

| Compound No. | $R_1$ | $R_3$ | $R_5$ | $R_6$ | % Inhibition of Ulcer 50 mg/kg i.p. (%) |
|---|---|---|---|---|---|
| Vb-3-1 | $CH_3CO$ | $(CH_3)_2CHCO$ | H | H | 56 |
| Vb-3-2 | $CH_3(CH_2)CO$ | $CH_3CO$ | H | H | 56 |
| Vb-4-1 | $(CH_3)_2CHCO$ | H | H | H | 78 |
| Vb-4-2 | $CH_3(CH_2)_{16}CO$ | H | H | H | 56 |
| Vb-4-3 | $CH_3O-\underset{CH_3}{CHCH_2CO}$ | H | H | H | 66 |
| Vb-5-1 | $C_2H_5$ | H | H | H | 94 |
| Vb-5-2 | $C_2H_5$ | H | H | $CH_3(CH_2)_2CH_2$ | 89 |
| Vb-5-3 | $C_2H_5$ | H | H | $CH_3\text{-}C_6H_4\text{-}CH_2$ (p-tolylmethyl via propyl) | 83 |
| Vb-6-1 | $CH_3CH_2$ | $CH_3CO$ | H | H | 66 |
| Vb-6-2 | $CH_3CH_2$ | $(CH_3)_2CHCO$ | H | H | 66 |
| Vb-6-3 | $CH_3CH_2$ | $CH_3CH_2CO$ | H | H | 66 |
| Vb-7-1 | $CH_3$ | $CH_3CH_2CH_2CH_2$ | H | H | 72 |
| Vb-7-2 | $CH_3CH_2CH_2CH_2$ | $CH_3CH_2CH_2CH_2$ | H | H | 66 |
| Vb-7-3 | $C_6H_5CH_2$ (benzyl) | $CH_3(CH_2)_2CH_2$ | H | H | 56 |
| Vb-8-1 | H | $CH_3$ | H | H | 78 |
| Vb-8-2 | H | $HC(CH_2)_7CH_3 = HC(CH_2)_7CH_2$ | H | H | 56 |
| Vb-8-3 | H | $CH_3CH_2$ | H | H | 78 |
| Vb-9-1 | $CH_3CO$ | $CH_3$ | H | H | 66 |
| Vb-9-2 | $CH_3CH_2CH_2CO$ | $CH_3CH_2$ | H | H | 66 |
| Vb-9-3 | $CH_3O-\underset{CH_3}{CHCH_2CH_2}$ | $CH_3CH_2$ | H | H | 66 |
| Vb-10-1 | H | H | $CH_3CH_2$ | H | 94 |

-continued

| Compound No. | R₁ | R₃ | R₅ | R₆ | % Inhibition of Ulcer 50 mg/kg i.p. (%) |
|---|---|---|---|---|---|
| Vb-10-2 | H | H | CH₃(CH₂)₂CH₂ | H | 100 |
| Vb-10-3 | H | H | CH₃(CH₂)₂CH₂ | CH₃(CH₂)₂CH₂ | 89 |
| Vb-11-1 | H | CH₃CO | CH₃CH₂ | H | 78 |
| Vb-11-2 | H | CH₃CO | (CH₃)₂CHCH₂CH₂ | H | 66 |
| Vb-11-3 | H | CH₃(CH₂)₂CO | CH₃(CH₂)₂CH₂ | H | 72 |
| Vb-12-1 | (CH₃)₂CHCO | CH₃CH₂CO | CH₃CH₂ | H | 56 |
| Vb-12-2 | CH₃CO | CH₃CO | CH₃CH₂ | H | 56 |
| Vb-12-3 | CH₃CO | CH₃CO | tetrahydrofuranyl-CH₂ | H | 44 |
| Vb-13-1 | CH₃CO | H | CH₃CH₂ | H | 78 |
| Vb-13-2 | CH₃CO | H | (CH₃)₂CHCH₂ | H | 72 |
| Vb-13-3 | CH₃CH₂CO | H | CH₃CH₂ | H | 78 |
| Vb-14-1 | CH₃ | H | CH₃CH₂ | H | 89 |
| Vb-14-2 | CH₃CH₂ | H | 4-CH₃-C₆H₄-CH₂ | H | 89 |
| Vb-14-3 | CH₃CH₂ | H | cyclohexyl-CH₂(CH₂)₂CH₂ | H | 83 |
| Vb-15-1 | (CH₃)₂CHCH₂ | CH₃CO | CH₃CH₂ | H | 56 |

-continued

| Compound No. | R₁ | R₃ | R₅ | R₆ | % Inhibition of Ulcer 50 mg/kg i.p. (%) |
|---|---|---|---|---|---|
| Vb-15-2 | CH₃CH₂ | CH₃CO | CH₃CHCH₂CH₂ with CH₃ branch | H | 56 |
| Vb-15-3 | 2-furylmethyl (furan-CH₂) | CH₃CH₂CH₂CO | CH₃CH₂CH₂CH₂ | H | 56 |
| Vb-16-1 | CH₃CH₂ | CH₃ | CH₃CH₂ | H | 66 |
| Vb-16-2 | 2-naphthylmethyl | CH₃ | CH₃(CH₂)₂CH₂ | H | 56 |
| Vb-16-3 | CH₃CH₂ | CH₃ | tetrahydrofuran-2-ylmethyl | H | 56 |
| Vb-17-1 | H | CH₃(CH₂)₂CH₂ | CH₃CH₂ | H | 72 |
| Vb-17-2 | H | CH₃(CH₂)₂CH₂ | CH₃(CH₂)₁₆CH₂ | H | 56 |
| Vb-17-3 | H | CH₃ | CH₃CH₂ | H | 72 |
| Vb-18-1 | CH₃CO | CH₃(CH₂)₂CH₂ | tetrahydrofuran-2-ylmethyl | H | 66 |
| Vb-18-2 | CH₃(CH₂)₁₆CO | CH₃(CH₂)₂CH₂ | CH₃CH₂ | H | 44 |
| Vb-18-3 | (CH₃)₂CHCO | CH₃ | CH₃CH₂ | H | 56 |
| Vb-19-1 | H | H | (CH₃)₂CH | H | 100 |
| Vb-19-2 | H | H | (CH₃)₂CH | H | 100 |
| Vb-19-3 | H | H | (CH₃)₂CH | 4-CH₃-C₆H₄ | 89 |

-continued

| Compound No. | $R_1$ | $R_3$ | $R_5$ | $R_6$ | % Inhibition of Ulcer 50 mg/kg i.p. (%) |
|---|---|---|---|---|---|
| Vb-20-1 | H | $CH_3CO$ | $CH_3$ | H | 72 |
| Vb-20-2 | H | $(CH_3)_2CHCH_2CO$ | $CH_3$ | H | 72 |
| Vb-20-3 | H | $CH_3CO$ | $(CH_3)_2CH$ | H | 72 |
| Vb-21-1 | $CH_3CO$ | $CH_3CO$ | $CH_3$ | H | 56 |
| Vb-21-2 | $CH_3CO$ | $CH_3CO$ | $(CH_3)_2CH$ | H | 66 |
| Vb-22-1 | $CH_3CO$ | H | $CH_3$ | H | 78 |
| Vb-22-2 | $(CH_3)_2CHCO$ | H | $(CH_3)_2CH$ | H | 66 |
| Vb-23-1 | $CH_3CH_2$ | H | $CH_3$ | H | 89 |
| Vb-23-2 | $CH_3CH_2$ | H | $CH_3$ | $CH_3(CH_2)_2CH_2$—⟨C_6H_4⟩—$CH_3$ (p-) | 89 |
| Vb-23-3 | $CH_3CH_2$ | H | $CH_3$ | H | 83 |
| Vb-24-1 | $CH_3CH_2$ | $CH_3CO$ | $CH_3$ | H | 66 |
| Vb-24-2 | $CH_3CH_2$ | $(CH_3)_2CHCO$ | $CH_3$ | H | 56 |
| Vb-24-3 | $CH_3CH_2$ | $CH_3CO$ | $(CH_3)_2CH$ | H | 66 |
| Vb-25-1 | $CH_3$ | $CH_3(CH_2)_2CH_2$ | $CH_3$ | H | 66 |
| Vb-25-2 | $CH_3$ | $CH_3(CH_2)_2CH_2$ | $(CH_3)_2CH$ | H | 66 |

-continued

| Compound No. | R₁ | R₃ | R₅ | R₆ | % Inhibition of Ulcer 50 mg/kg i.p. (%) |
|---|---|---|---|---|---|
| Vb-25-3 | CH₃(CH₂)₂CH₂ | CH₃(CH₂)₂CH₂ | CH₃ | H | 66 |
| Vb-26-1 | H | CH₃ | CH₃ | H | 78 |
| Vb-26-2 | H | CH₃(CH₂)₁₇ | CH₃\_CH\_CH₃ | H | 56 |
| Vb-26-3 | H | CH₃ | CH₃\_CH\_CH₃ | H | 78 |
| Vb-27-1 | CH₃CO | CH₃ | CH₃ | H | 66 |
| Vb-27-2 | CH₃CO | CH₃ | CH₃\_CH\_CH₃ | H | 66 |

| Compound No. | $R_1$ | $R_3$ | $R_6$ | % Inhibition of Ulcer 50 mg/kg i.p. (%) |
|---|---|---|---|---|
| VI-1-1 | H | H | $CH_3$ | 56 |
| VI-1-2 | H | H | $CH_3(CH_2)_2CH_2$ | 44 |
| VI-1-3 | H | H | $CH_3(CH_2)_{16}CH_2$ | 33 |
| VI-1-4 | H | H | C₆H₅—$CH_2$ | 44 |
| VI-1-5 | H | H | cyclohexyl—$CH_2$ | 44 |
| VI-1-6 | H | H | (2-furyl)—$CH_2$ | 44 |
| VI-1-7 | H | H | (tetrahydropyran-2-yl)—$CH_2CH_2$ | 44 |
| VI-1-8 | H | H | $CH_3CON$(piperidyl)—$CH_2$ | 56 |
| VI-1-9 | H | H | (2-naphthyl)—$CH_2CH_2$ | 44 |
| VI-1-10 | H | H | $BrCH_2CH_2CH_2$ | 56 |
| VI-2-1 | H | $CH_3CO$ | H | 44 |
| VI-2-2 | H | $CH\equiv C-CO$ | H | 56 |
| VI-2-3 | H | cycloheptyl—CO | H | 44 |
| VI-3-1 | $CH_3CO$ | $CH_3CO$ | H | 44 |
| VI-3-2 | $CH_3CH_2CO$ | $CH_3CO$ | H | 44 |
| VI-3-3 | $CH_3CO$ | $CH_3CO$ | $BrCH_2CH_2CH_2$ | 44 |
| VI-4-1 | $CH_3CO$ | H | H | 56 |
| VI-4-2 | $CH_3(CH_2)_3CO$ | H | C₆H₅—$CH_2$ | 44 |
| VI-4-3 | (CH₃)(H)C=C(H)(CO)— | H | 56 | |
| VI-5-1 | $CH_3$ | H | H | 56 |
| VI-5-2 | C₆H₅—$CH_2CH_2$ | H | H | 44 |

-continued

| Compound No. | $R_1$ | $R_3$ | $R_6$ | % Inhibition of Ulcer 50 mg/kg i.p. (%) |
|---|---|---|---|---|
| VI-5-3 | tetrahydropyran-2-yl-CH$_2$CH$_2$ | H | H | 44 |
| VI-6-1 | CH$_3$ | CH$_3$CO | H | 44 |
| VI-6-2 | CH$_3$ | CH$_3$CO | CH$_3$ | 33 |
| VI-6-3 | CH$_3$CH$_2$ | CH$_3$CH$_2$CO | H | 44 |
| VI-7-1 | CH$_3$ | CH$_3$ | H | 44 |
| VI-7-2 | CH$_3$(CH$_2$)$_2$CH$_2$ | CH$_3$CH$_2$ | H | 44 |
| VI-7-3 | C$_6$H$_5$—CH$_2$ | (CH$_3$)$_2$CHCH$_2$ | H | 33 |
| VI-8-1 | H | CH$_3$ | H | 56 |
| VI-8-2 | H | cyclohexyl-CH$_2$ | H | 56 |
| VI-8 | H | CH$_3$CH$_2$C(=O)CH$_2$ | H | 44 |
| V-9-1 | CH$_3$CO | CH$_3$ | H | 44 |
| VI-9-2 | ClCH$_2$CO | cyclohexyl-CH$_2$ | H | 44 |
| VI-9-3 | CH$_3$CO | (CH$_3$)$_2$CHCH$_2$ | H | 44 |

| Compound No. | $R_1$ | $R_3$ | $R_5$ | $R_7$ | % Inhibition of Ulcer 25 mg/kg i.p. (%) |
|---|---|---|---|---|---|
| VII-1-1 | H | H | H | H | 100 |
| VII-1-2 | H | H | H | $CH_3$ | 100 |
| VII-1-3 | H | H | H | $CH_3CH_2$ | 100 |
| VII-1-4 | H | H | H | $CH_3(CH_2)_2CH_2$ | 100 |
| VII-1-5 | H | H | H | $(CH_3)_2CHCH_2CH_2$ | 100 |
| VII-1-6 | H | H | H | $CH_3(CH_2)_{16}CH_2$ | 89 |
| VII-1-7 | H | H | H | $ClCH_2CH_3$ | 100 |
| VII-1-8 | H | H | H | $HC(CH_2)_7CH_3$<br>$=$<br>$HC(CH_2)_7CH_2$ | 89 |
| VII-1-9 | H | H | H | 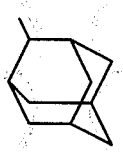 | 89 |
| VII-1-10 | H | H | H | 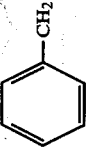$-CH_2$ | 94 |
| VII-1-11 | H | H | H | △ | 94 |
| VII-1-12 | H | H | H | 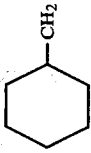$-CH_2$ | 94 |
| VII-1-13 | H | H | H | 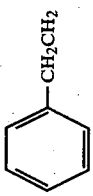$-CH_2CH_2$ | 89 |
| VII-1-14 | H | H | H | 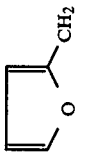 | 89 |

-continued
| Compound No. | $R_1$ | $R_3$ | $R_5$ | $R_7$ | % Inhibition of Ulcer 25 mg/kg i.p. (%) |
|---|---|---|---|---|---|
| VII-1-15 | H | H | H | 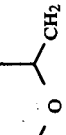 | 89 |
| VII-1-16 | H | H | H | 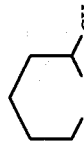 | 94 |
| VII-1-17 | H | H | H | 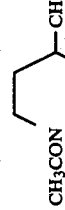 | 83 |
| VII-1-18 | H | H | H | 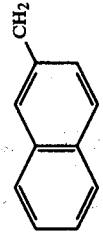 | 78 |
| VII-1-19 | H | H | H | 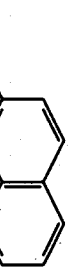 | 78 |
| VII-1-20 | H | H | H | 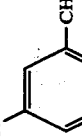 | 94 |
| VII-1-21 | H | H | H |  | 100 |
| VII-1-22 | H | H | H | 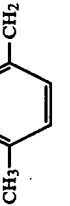 | 83 |

-continued
| Compound No. | $R_1$ | $R_3$ | $R_5$ | $R_7$ | % Inhibition of Ulcer 25 mg/kg i.p. (%) |
|---|---|---|---|---|---|
| VII-1-23 | H | H | H | 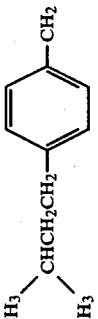 | 83 |
| VII-1-24 | H | H | H | 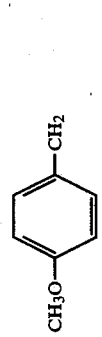 | 83 |
| VII-1-25 | H | H | H | 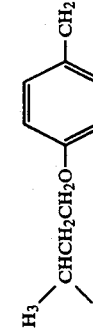 | 83 |
| VII-1-26 | H | H | H |  | 94 |
| VII-1-27 | H | H | H |  | 89 |
| VII-1-28 | H | H | H |  | 94 |
| VII-1-29 | H | H | H | 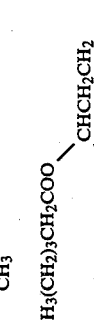 | 94 |
| VII-1-30 | H | H | H | 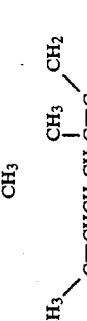 | 83 |
| VII-1-31 | H | H | H |  | 83 |

-continued

| Compound No. | $R_1$ | $R_3$ | $R_5$ | $R_7$ | % Inhibition of Ulcer 25 mg/kg i.p. (%) |
|---|---|---|---|---|---|
| VII-1-32 | H | H | H | (2,5-dihydrofuran-3-yl)–CH=CHCH$_2$ | 83 |
| VII-1-33 | H | H | H | cycloheptyl–CH$_2$ | 83 |
| VII-1-34 | H | H | H | cyclopentyl–CH$_2$CH$_2$CH$_2$ | 83 |
| VII-1-35 | H | H | H | 4-methylphenyl–CH$_2$CH$_2$ | 83 |
| VII-1-36 | H | H | H | (CH$_3$)$_2$CH(CH$_2$)$_3$CH(CH$_3$)CH(CH$_2$)$_3$CH$_2$– | 83 |
| VII-1-37 | H | H | H | long branched terpenoid chain | 94 |
| VII-1-38 | H | H | H | 4-(isopropyl)phenyl–CH(CH$_3$) | 94 |
| VII-1-39 | H | H | H | bornyl | 83 |

-continued

| Compound No. | R₁ | R₃ | R₅ | R₇ | % Inhibition of Ulcer 25 mg/kg i.p. (%) |
|---|---|---|---|---|---|
| VII-1-40 | H | H | H | CH₃(CH₂)₄–C₆H₄–CH₂– | 94 |
| VII-1-41 | H | H | H | CH₃CH₂CH₂CH=CH–C₆H₄–CH₂– | 83 |
| VII-1-42 | H | H | H | (CH₃)₂CH– | 94 |
| VII-1-43 | H | H | H | CH₃–C₆H₄– | 94 |
| VII-1-44 | H | H | H | CH₃CH₂N(piperidinyl)– | 94 |
| VII-1-45 | H | H | H | morpholino–CH₂CH₂– | 94 |
| VII-1-46 | H | H | H | piperidino–CH₂CH₂– | 94 |
| VII-1-47 | H | H | H | C₆H₅– | 94 |

-continued

| Compound No. | $R_1$ | $R_3$ | $R_5$ | $R_7$ | % Inhibition of Ulcer 25 mg/kg i.p. (%) |
|---|---|---|---|---|---|
| VII-2-1 | H | CH$_3$CO | H | H | 78 |
| VII-2-2 | H |  | H | H | 78 |
| VII-2-3 | H | $\underset{CH_3}{\overset{H}{C}}=\underset{H}{\overset{CO}{C}}$ | H | H | 78 |
| VII-2-4 | H | HC(CH$_2$)$_7$CH$_3$<br>‖<br>HC(CH$_2$)$_7$CO | H | H | 66 |
| VII-3-1 | CH$_3$CO | (CH$_3$)$_2$CHCO | H | H | 78 |
| VII-3-2 | CH$_3$(CH$_2$)$_2$CO | CH$_3$CO | H | H | 78 |
| VII-4-1 | CH$_3$CO | H | H | CH$_3$ | 83 |
| VII-4-2 | (CH$_3$)$_2$CHCO | H | H | H | 89 |
| VII-4-3 | CH$_3$(CH$_2$)$_16$CO | H | H | H | 78 |
| VII-4-4 | CH$_3$O−CH−CH$_2$CO<br>\|<br>CH$_3$ | H | H | H | 89 |
| VII-5-1 | CH$_3$ | H | H | H | 78 |
| VII-5-2 | C$_2$H$_5$ | H | H | H | 78 |
| VII-5-3 | C$_2$H$_5$ | H | H | CH$_3$(CH$_2$)$_2$CH$_2$ | 78 |
| VII-5-4 | C$_2$H$_5$ | H | H | H | 78 |
| VII-5-5 |  | H | H |  | 78 |
| VII-5-6 | CH$_3$CH$_2$C−CH$_2$<br>‖<br>O | H | H | H | 83 |

-continued

| Compound No. | R₁ | R₃ | R₅ | R₇ | % Inhibition of Ulcer 25 mg/kg i.p. (%) |
|---|---|---|---|---|---|
| VII-5-7 | cyclopentyl-CH₂CH₂CH₂ | H | H | H | 78 |
| VII-6-1 | CH₃CH₂ | CH₃CO | H | H | 66 |
| VII-6-2 | " | (CH₃)₂CHCO | H | H | 66 |
| VII-6-3 | " | CH₃CH₂CO | H | H | 66 |
| VII-7-1 | CH₃ | CH₃CH₂CH₂CH₂ | H | H | 89 |
| VII-7-2 | CH₃CH₂CH₂CH₂ | " | H | H | 72 |
| VII-7-3 | benzyl (C₆H₅CH₂) | CH₃(CH₂)₂CH₂ | H | H | 72 |
| VII-7-4 | CH₃CH₂ | CH₃CH₂CH₂ | H | CH₃(CH₂)₂CH₂ | 66 |
| VII-8-1 | H | CH₃ | H | H | 89 |
| VII-8-2 | H | HC(CH₂)₇CH₃ ‖ HC(CH₂)₇CH₂ | H | H | 66 |
| VII-8-3 | H | CH₃CH₂ | H | CH₃CH₂ | 89 |
| VII-9-1 | CH₃CH₂CO | CH₃ | H | H | 66 |
| VII-9-2 | CH₃(CH₂)₁₆CO | " | H | H | 56 |
| VII-9-3 | CH₃CO | " | H | H | 72 |
| VII-9-4 | CH₃CH₂CH₂CO | CH₃CH₂ | H | H | 78 |
| VII-9-5 | CH₃O-CHCH₂CH₂- \| CH₃ CHCH₂CH₂ | " | H | H | 78 |
| VII-10-1 | H | H | CH₃CH₂CH₂ | H | 94 |
| VII-10-2 | H | H | CH₃(CH₂)₃CH₂ | H | 94 |
| VII-10-3 | H | H | CH₃(CH₂)₆CH₂ | H | 94 |
| VII-10-4 | H | H | CH₃(CH₂)₂CH₂ | CH₃(CH₂)₂CH₂ | 72 |
| VII-10-5 | H | H | CH₃(CH₂)₁₆CH₂ | H | 89 |
| VII-11-1 | H | CH₃CO | CH₃CH₂ | H | 72 |
| VII-11-2 | H | " | CH₃-CHCH₂CH₂ \| CH₃ | H | 72 |

-continued

| Compound No. | $R_1$ | $R_3$ | $R_5$ | $R_7$ | % Inhibition of Ulcer 25 mg/kg i.p. (%) |
|---|---|---|---|---|---|
| VII-11-3 | H | $CH_3(CH_2)_2CO$ | $CH_3(CH_2)_2CH_2$ | H | 66 |
| VII-11-4 | H | $CH_3CH_2CO$ | $CH_3CH_2$ | $ClCH_2CH_2$ | 56 |
| VII-12-1 | $(CH_3)_2CHCO$ | $CH_3CH_2CO$ | $CH_3CH_2$ | H | 56 |
| VII-12-2 | $CH_3CO$ | $CH_3CO$ | ⟨tetrahydrofuran-2-yl-CH$_2$⟩ | H | 56 |
| VII-12-3 | " |  | ⟨4-methylphenyl-CH$_2$⟩ | H | 56 |
| VII-13-1 | " | H | $CH_3CH_2$ | H | 83 |
| VII-13-2 | $CH_3CH_2CO$ | H | $(CH_3)_2CHCH_2$ | H | 83 |
| VII-13-3 | $CH_3(CH_2)_2CH_2$ | H | $CH_3CH_2$ | $CH_3$ | 72 |
| VII-14-1 | $CH_3$ | H | " | H | 83 |
| VII-14-2 |  | H |  |  | 72 |
| VII-14-3 | $CH_3CH_2$ | H | $HC(CH_2)_7CH_3$ =  $HC(CH_2)_7CH_2$ | $CH_3CH_2$ | 50 |
| VII-14-4 | " | H | cyclohexyl-$CH_2(CH_2)_2CH_2$ | H | 72 |
| VII-14-5 | " | H | ⟨phenyl-CH$_2$⟩ | H | 72 |
| VII-14-6 | " | H | $CH_3CH_2$ | phenyl-$CH_3$ | 50 |
| VII-14-7 | " | H | cyclohexyl-$CH_2CH_2CH_2CH_2$ | $CH_3$ | 56 |

-continued

| Compound No. | R₁ | R₃ | R₅ | R₇ | % Inhibition of Ulcer 25 mg/kg i.p. (%) |
|---|---|---|---|---|---|
| VII-14-8 | " | H | tetrahydrofuran-2-ylmethyl (CH₂-furan-O) | H | 72 |
| VII-15-1 | (CH₃)₂CHCH₂ | CH₃CO | CH₃CH₂ | H | 50 |
| VII-15-2 | CH₃CH₂ | " | " | | 50 |
| VII-15-3 | | CH₃CH₂CH₂CO | (CH₃)₂CH-CH₂CH₂ | H | 50 |
| VII-15-4 | CH₃ | CH₃CH₂CO | CH₃CH₂CH₂CH₂ | H | 44 |
| VII-16-1 | CH₃CH₂ | CH₃ | " | CH₃CH₂ | 56 |
| VII-16-2 | naphthalen-2-ylmethyl | " | CH₃(CH₂)₂CH₂ | H | 50 |
| VII-16-3 | CH₃CH₂ | " | " | H | 50 |
| VII-16-4 | CH₃(CH₂)₂CH₂ | " | " | CH₃CH₂ | 44 |
| VII-17-1 | H | " | CH₃CH₂ | H | 78 |
| VII-17-2 | H | CH₃(CH₂)₂CH₂ | CH₃(CH₂)₁₆CH₂ | H | 56 |
| VII-17-3 | H | CH₃ | CH₃CH₂ | H | 89 |
| VII-18-1 | CH₃CO | CH₃(CH₂)₂CH₂ | " | H | 66 |
| VII-18-2 | CH₃(CH₂)₁₆CO | " | " | H | 44 |
| VII-18-3 | (CH₃)₂CHCO | CH₃ | CH₃CH₂ | H | 56 |

-continued

| Compound No. | R₁ | R₃ | R₅ | R₇ | % Inhibition of Ulcer 25 mg/kg i.p. (%) |
|---|---|---|---|---|---|
| VII-19-1 | H | H | CH₃ | H | 100 |
| VII-19-2 | H | H | (CH₃)₂CH | H | 89 |
| VII-19-3 | H | H | " | 4-CH₃-C₆H₄- | 66 |
| VII-20-1 | H | CH₃CO | CH₃ | H | 89 |
| VII-20-2 | H | (CH₃)₂CHCH₂CO | " | H | 66 |
| VII-20-3 | H | CH₃CO | (CH₃)₂CH | H | 78 |
| VII-21-1 | CH₃CO | " | CH₃ | H | 66 |
| VII-21-2 | " | " | (CH₃)₂CH | H | 66 |
| VII-22-1 | " | H | CH₃ | H | 78 |
| VII-22-2 | (CH₃)₂CHCO | H | (CH₃)₂CH | H | 66 |
| VII-23-1 | CH₃CH₂ | H | CH₃ | H | 89 |
| VII-23-2 | " | H | " | CH₃(CH₂)₂CH₂ | 66 |
| VII-23-3 | CH₃CH₂ | H | CH₃ | 4-CH₃-C₆H₄- | 66 |

-continued

| Compound No. | R$_1$ | R$_3$ | R$_5$ | R$_7$ | % Inhibition of Ulcer 25 mg/kg i.p. (%) |
|---|---|---|---|---|---|
| VII-23-4 | (adamantyl) | H | " | CH$_3$ | 66 |
| VII-23-5 | CH$_3$ | H | " | H | 89 |
| VII-24-1 | CH$_3$CH$_2$ | CH$_3$CO | CH$_3$ | H | 66 |
| VII-24-2 | " | (CH$_3$)$_2$CHCO | " | H | 66 |
| VII-24-3 | " | CH$_3$CO | CH$_3$CH(CH$_3$) | H | 66 |
| VII-25-1 | CH$_3$ | CH$_3$(CH$_2$)$_2$CH$_2$ | CH$_3$ | H | 66 |
| VII-25-2 | " | CH$_3$(CH$_2$)$_2$CH$_2$ | CH$_3$CH(CH$_3$) | H | 56 |
| VII-25-3 | CH$_3$(CH$_2$)$_2$CH$_2$ | CH$_3$(CH$_2$)$_2$CH$_2$ | CH$_3$ CH$_3$ | H | 56 |
| VII-26-1 | H | CH$_3$ | CH$_3$ | H | 89 |
| VII-26-2 | H | CH$_3$(CH$_2$)$_{17}$ | CH$_3$CH(CH$_3$) | H | 56 |
| VII-26-3 | H | CH$_3$ | " | H | 89 |
| VII-27-1 | CH$_3$CO | CH$_3$ | CH$_3$ | H | 66 |
| VII-27-2 | " | " | CH$_3$CH(CH$_3$) | H | 66 |
| VII-28-1 | H | H | CH$_3$CO | H | 78 |
| VII-28-2 | H | H | (CH$_3$)$_2$CHCO | H | 78 |
| VII-28-3 | H | H | CH$_3$(CH$_2$)$_6$CO | H | 66 |
| VII-28-4 | H | H | CH$_3$(CH$_2$)$_{16}$CO | CH$_3$CH$_2$ | 66 |
| VII-29-1 | (CH$_3$)$_2$CHCO | CH$_3$CH$_2$CO | CH$_3$CO | CH$_3$ | 66 |
| VII-30-1 | CH$_3$CO | CH$_3$CH$_2$CO | " | CH$_3$(CH$_2$)$_2$CH$_2$ | 44 |
| VII-31-1 | CH$_3$(CH$_2$)$_2$CH$_2$ | H | " | H | 89 |
| VII-32-1 | CH$_3$(CH$_2$)$_2$CH$_2$ | H | " | CH$_3$CH$_2$ | 66 |

-continued

| Compound No. | $R_1$ | $R_3$ | $R_5$ | $R_7$ | % Inhibition of Ulcer 25 mg/kg i.p. (%) |
|---|---|---|---|---|---|
| VII-33-1 | $CH_3$ | $CH_3CH_2CO$ | " | H | 66 |
| VII-34-1 | $CH_3(CH_2)_2CH_2$ | $CH_3$ | " | H | 66 |
| VII-35-1 | H | $CH_3$ | " | $CH_3CH_2$ | 66 |
| VII-36-1 | $(CH_3)_2CHCO$ | $CH_3$ | " | H | 66 |

| Compound No. | $R_1$ | $R_3$ | $R_7$ | % Inhibition of Ulcer 50 mg/kg i.p. (%) |
|---|---|---|---|---|
| VIII-1-1 | H | H | $CH_3$ | 56 |
| VIII-1-2 | H | H | $CH_3(CH_2)_3CH_2$ | 56 |
| VIII-1-3 | H | H | $CH_3(CH_2)_{16}CH_2$ | 44 |
| VIII-1-4 | H | H | 3-chlorobenzyl ($-CH_2-C_6H_4-Cl$) | 44 |
| VIII-1-5 | H | H | cyclohexyl-$CH_2$ | 44 |
| VIII-1-6 | H | H | 2-furyl-$CH_2$ | 44 |
| VIII-1-7 | H | H | (tetrahydropyran-2-yl)-$CH_2CH_2$ | 44 |
| VIII-1-8 | H | H | (1-acetylpiperidin-4-yl)-$CH_2$ ($CH_3CON\!\!<\!\!{piperidinyl}\!\!>\!\!-CH_2$) | 56 |
| VIII-1-9 | H | H | 2-naphthyl-$CH_2CH_2$ | 33 |
| VIII-1-10 | H | H | $CH_3CH_2CH_2$ | 56 |
| VIII-2-1 | H | $CH_3CO$ | H | 44 |
| VIII-2-2 | H | $CH\!\equiv\!C\!-\!CO$ | H | 44 |
| VIII-2-3 | H | cycloheptyl-CO | H | 33 |
| VIII-3-1 | $CH_3CO$ | $CH_3CO$ | H | 22 |
| VIII-3-2 | $CH_3CH_2CO$ | " | H | 22 |
| VIII-3-3 | $CH_3CO$ | " | $CH_3CH_2CH_2$ | 17 |
| VIII-4-1 | " | H | H | 44 |
| VIII-4-2 | $CH_3(CH_2)_3CO$ | H | phenyl-$CH_2$ | 44 |
| VIII-4-3 | $CH_3\!-\!CH\!=\!CH\!-\!CO$ (cis: $CH_3,H / H, CO$) | H | H | 44 |
| VIII-5-1 | $CH_3$ | H | H | 56 |
| VIII-5-2 | phenyl-$CH_2CH_2$ | H | H | 33 |

-continued

| Compound No. | R₁ | R₃ | R₇ | % Inhibition of Ulcer 50 mg/kg i.p. (%) |
|---|---|---|---|---|
| VIII-5-3 | ⟨tetrahydropyran-2-yl⟩-CH₂CH₂- (O in ring) | H | H | 44 |
| VIII-6-1 | CH₃ | CH₃CO | H | 33 |
| VIII-6-2 | " | " | CH₃ | 22 |
| VIII-6-3 | CH₃CH₂ | CH₃CH₂CO | H | 33 |
| VIII-7-1 | CH₃ | CH₃ | H | 33 |
| VIII-7-2 | CH₃(CH₂)₂CH₂ | CH₃CH₂ | H | 33 |
| VIII-7-3 | C₆H₅CH₂- | (CH₃)₂CHCH₂- | H | 22 |
| VIII-8-1 | H | CH₃ | H | 44 |
| VIII-8-2 | H | cyclohexyl-CH₂- | H | 33 |
| VIII-8-3 | H | CH₃CH₂COCH₂- | H | 33 |
| VIII-9-1 | CH₃CO | CH₃ | H | 33 |
| VIII-9-2 | ClCH₂CO | cyclohexyl-CH₂- | H | 22 |
| VIII-9-3 | CH₃CO | (CH₃)₂CHCH₂ | H | 22 |

TABLE 14

| Compound No. | % Inhibition of Ulcer 50 mg/kg i.p. (%) |
|---|---|
| A | 100 |
| B | 100 |
| C | 66 |
| D | 66 |
| E | 44 |
| F | 44 |
| G | 33 |

TABLE 15

| Compound No. | % Inhibition of Edema 100 mg/kg p.o. (after 3 hours) (%) |
|---|---|
| IIIa-18-1 | 38 |
| IIIa-18-2 | 38 |
| IIIa-18-3 | 42 |
| IIIa-18-4 | 47 |
| IIIa-18-5 | 47 |
| IIIa-18-6 | 50 |
| IIIa-18-7 | 51 |
| IIIa-18-8 | 50 |
| IIIa-18-9 | 43 |
| IIIa-18-10 | 43 |
| IIIa-18-11 | 35 |
| IIIa-18-13 | 35 |
| IIIa-22-1 | 37 |
| IIIa-22-2 | 35 |
| IIIa-22-3 | 38 |
| IIIa-22-5 | 37 |
| IIIa-22-8 | 31 |
| IIIa-22-74 | 45 |
| IIIa-22-75 | 48 |
| IIIa-22-114 | 48 |
| IIIa-27-1 | 38 |
| IIIa-27-2 | 42 |

This invention is now described in greater detail by reference to the following examples which are given here for illustrative purposes only and are by no means intended to limit the scope of the invention. Expressions of % in the Examples are by weight, except for expressions of % and ratios for mixed solvent systems, which are on a volume basis.

EXAMPLE 1

A common slant agar was inoculated with *Bacillus pumilus* AI-77 (ATCC No. 31650), which was incubated at 30° C. for a day to produce a seed culture. A 500-ml shake flask with shoulders was charged with 100 ml of a nutrient medium of the following composition. The seed culture was inoculated on the medium and subjected to reciprocated shake cultivation at 30° C. for a day. The incubated microorganism was used as a seed culture in the subsequent examples.

| | |
|---|---|
| Glucose | 1.0 (%) |
| Polypeptone | 1.0 |
| Meat extract | 0.5 |

-continued

| | |
|---|---|
| NaCl | 0.5 |
| KF-96 (defoaming agent of Shinetsu Chemical Industry Co., Ltd.) | 0.1 |

EXAMPLE 2

Production of Compound A

A 20-liter jar fermentor containing 10 liters of a nutrient medium of the following composition was inoculated with 500 ml of the seed prepared in Example 1. Fermentation was conducted at 30° C. for a day (1 v/v/m (air flow amount (l)/amount of fermentation solution (l)/min) 300 rpm).

| | |
|---|---|
| "Pharmamedia" | 2.0 (%) |
| Molasses | 5.0 |
| $MgSO_4.7H_2O$ | 0.05 |
| $K_2HPO_4$ | 0.2 |
| NaCl | 0.3 |
| KF-96 | 0.1 |

The pH before sterilization was adjusted to 7.0, and then the medium was sterilized at 120° C. for 20 minutes.

After completion of the fermentation, the culture was centrifuged continuously, and the filtrate was passed through a column packed with 500 ml of Amberlite IRC-50 (H type). The column was washed with 5 liters of water, and compound A was eluted with 10 liters of 0.05 N aqueous hydrochloric acid. The eluate was passed through a column filled with 200 ml of Amberlite XAD-2. The column was washed with 2 liters of water, and compound A was eluted with 4 liters of water containing 10% of methanol. The eluate was concentrated and freeze-dried to give 380 mg of a pale yellow powder of compound A as a hydrochloride. The powder was dissolved in 20 ml of water and adsorbed on a column packed with 100 ml of XAD-2. After the column was washed with one liter of water, compound A was eluted with 2 liters of water containing 10% of methanol. The eluate was concentrated and freeze-dried to give 285 mg of a white powder of compound A as a hydrochloride. The powder had physicochemical properties that corresponded to the physicochemical data for compound A described herein.

EXAMPLE 3

Production of Compound A

A 200-liter fermentation tank was charged with 100 liters of a medium of the following composition and inoculated with 3 liters of the seed prepared in Example 1. Fermentation was conducted at 30° C. for 20 hours (1 v/v/m, 300 rpm).

| | |
|---|---|
| Defatted soybean meal | 2.0 (%) |
| Glucose | 2.0 |
| $K_2HPO_4$ | 0.2 |
| $MgSO_4.7H_2O$ | 0.05 |
| NaCl | 0.3 |
| KF-96 | 0.1 |

The pH before sterilization was adjusted to 7.0, and then the medium was sterilized at 120° C. for 40 minutes.

The culture was filtered through a hollow fiber ultrafilter. The resulting filtrate was passed through a column packed with 9 liters of Amberlite IRC-50 (H type). The column was washed with 45 liters of water, and compound A was eluted with 160 liters of 0.05 N aqueous hydrochloric acid. The eluate was passed through a column packed with 3.5 liters of Amberlite XAD-2. The column was washed with 18 liters of water, and compound A was eluted with 60 liters of water containing 10% of methanol. The eluate was concentrated to 5 liters in vacuum and passed through Amberlite XAD-2 for further purification. The eluate of compound A was concentrated and freeze-dried to give 4.3 g of a white powder of compound A as a hydrochloride. The powder had physicochemical properties that corresponded to the physicochemical data for compound A described herein.

EXAMPLE 4

Production of Compounds B, C, D, E, F and G

A 200-liter fermentation tank was charged with 100 liters of a medium of the following composition and inoculated with 3 liters of the seed prepared in Example 1. Fermentation was conducted at 30° C. for 4 days (0.5 v/v/m, 300 rpm).

| | |
|---|---|
| Defatted soybean meal | 1 (%) |
| Corn steep liquor | 1 |
| Sucrose | 2 |
| $K_2HPO_4$ | 0.2 |
| $MgSO_4.7H_2O$ | 0.05 |
| NaCl | 0.3 |
| KF-96 | 0.1 |

After the fermentation, the broth was filtered through a hollow fiber ultrafilter cell. The resulting filtrate was passed through a column packed with 5 liters of Amberlite XAD-2. The column was washed with 15 liters of water, and compound G was eluted with 20 liters of water. The fraction was concentrated and dried to give 4.8 g of a crude powder of compound G. (The powder can be purified further by means of the technique described in Example 6.) The column was fed with 50 liters of 10% aqueous methanol solution to remove the unwanted portion, and compound B was eluted with 150 liters of 30% aqueous methanol solution. Upon concentration of the eluate in vacuum, 42 g of a crude specimen of compound B resulted. The specimen was dissolved in 2 liters of boiling water and allowed to cool to give 23 g of a white crystal of a tetrahydrate salt of compound B. The crystal was dried on phosphorus pentoxide in vacuum at 60° C. for 6 hours. The dried crystal had physicochemical properties that corresponded to the physicochemical data of compound B described herein. After elution of compound B, 15 liters of 80% aqueous methanol was passed through the column of XAD-2 to elute compounds C to F altogether. Upon concentration in vacuum, 5.6 g of a powder containing compounds C to F resulted. As will be described in Example 7, compounds C to F in the powder can be separated from each other.

EXAMPLE 5

Production of Compounds B to F

A 20-liter jar fermentor was charged with 10 liters of a medium identical with what was used in Example 1, and inoculated with 500 ml of the seed prepared in Example 1. Fermentation was conducted at 30° C. for a day (0.5 v/v/m, 300 rpm). A 200-liter fermentation tank charged with 125 liters of a medium identical with what was used in Example 1 was inoculated with 7 liters of the culture as a seed. Fermentation was conducted at 30° C. for 18 hours (0.5 v/v/m, 300 rpm). A 5-m³ fermentation tank charged with 2.5 m³ of a medium identical with what was used in Example 3 was inoculated with a seed comprising all of the culture obtained. Fermentation was conducted at 30° C. for 4 days (0.5 v/v/m, 170 rpm).

After the fermentation, the broth was filtered through a hollow fiber ultrafilter cell. The filtrate was passed through a first column packed with 130 liters of XAD-2. After washing the column with 2.6 m³ of 10% aqueous methanol, 2.6 m³ of 30% aqueous methanol was passed through the column to elute compound B. The eluate mixed with an equal amount of water was continuously passed through a second column packed with 80 liters of XAD-2 to adsorb compound B on the column again. After washing the column with 1.6 m³ of 20% aqueous methanol, compound B was eluted with 180 liters of 100% methanol.

Concentrating the methanol eluate gave 650 g of a tetrahydrate salt of compound B. Upon high pressure liquid chromatography, the specimen was found to have a purity of 98%. It could be purified further by recrystallization from boiling water.

After eluting compound B with 30% aqueous methanol, the first column was fed with 260 liters of 80% aqueous methanol to give an eluate containing compounds C to F. If necessary, Compounds C to F can be separated from each other by subjecting a concentrate of the eluate to the method described in Example 7.

EXAMPLE 6

Purification of Compound G

Two grams of the crude powder of compound G prepared in Example 4 was dissolved in methanol, adsorbed in a line on twelve preparative silica gel plates (5717 of Merck & Co., Ind.), and developed with a solvent system comprising equal volumes of chloroform and methanol. Absorbing portions having Rf=0.35 as determined under an UV lamp were scraped from the plates and extracted with methanol. The extract was filtered through a Millipore filter FHLPO 1300 (product of Millipore Corporation), concentrated in vacuum, and freeze-dried to give 418 mg of a white powder of compound G. the powder had physicochemical properties that corresponded to the physicochemical date for compound G described herein.

EXAMPLE 7

Separation of Compounds C to F

Three grams of the powder containing compounds C to F obtained in Example 4 was dissolved in methanol, adsorbed on 5 g of silica gel (Silica 60 Extra Pure of 70-200 Tyler mesh manufactured by Merck & Co., Inc.) and methanol was distilled off. A suspension of 600 g of silica gel (the same as used above) in ethyl ether was filled in a column. The silica gel onto which the powder containing C to F was adsorbed was suspended in ethyl ether to form a slurry, which was placed on top of the column. Elution was performed by passing three developing solvents, (1) ethyl ether, (2) a mixture of ethyl ether and ethyl acetate (7:3 by volume) and (3) ethyl acetate, through the column sequentially. The eluting operation was conducted by monitoring the eluates from TLC on silica gel: the elution with solvent (1) was continued until the UV absorbing substance that moved to the tip of a silica gel (5714 of Merck & Co., Inc.) on TLC using that solvent as a developing system was no longer eluted; the elution with solvent (2) was continued until the UV absorbing substance positioned at Rf=0.48 (F) on TLC using that solvent as a developing system was no longer eluted; the elution with solvent (3) was continued until the UV absorbing substances positioned at Rf=0.55 (E), Rf=0.47 (D) and Rf=0.28 (C) on TLC using that solvent as a developing system were no longer eluted. The eluted fractions of the respective compounds on TLC were combined and concentrated in vacuum. As a result, 112 mg of a crystalline powder of E, 36 mg of a white powder of D and 105 mg of a white powder of C were obtained. The compounds C to F obtained had physicochemical properties that corresponded to the physicochemical data for the respective compounds described herein.

EXAMPLE 8

To a solution of 8.48 g (20 millimols) of thoroughly dried AI-77-B in 36 ml of pyridine, 4.08 g (40 millimols) of acetic anhydride was added dropwise at room temperature, followed by a 3-hr stirring. The reaction was monitored by thin layer chromatography (e.g. on TLC 5714 of Merck & Co., Inc. using chloroform/methanol (10:1) as a developing solvent). After distilling the pyridine in vacuum, the residue was washed twice with a total of 100 ml of water (50 ml each). The residue was dissolved in a water-methanol solvent system (50% of water and 50% of methanol), and the solution was passed through a column packed with one liter of Amberlite XAD-2. The column was washed with 5 liters of water and eluted with a solvent system comprising 85% of methanol and 15% of water. The eluting fractions were combined, concentrated and dried to give 7.5 g of a compound. From IR, UV, NMR spectrum and FD-mass spectrum analysis, the compound was identified as the end compound IIIa-1-1. The same identification means were employed in the subsequent examples.

EXAMPLE 9

To a solution of 30 g (71 millimols) of thoroughly dried AI-77-B in 500 ml of pyridine, 38.2 g (142 millimols) of caprylic anhydride was added at room temperature. Following a 3-hr stirring at room temperature, the pyridine was distilled off in vacuum. The dried product was dissolved in 400 ml of methanol and mixed with HCl-saturated methanol to give a pH of 1. The acidic solution was concentrated to dryness in vacuum. The concentrate was dissolved in 200 ml of methanol and mixed with 1 N aqueous sodium hydroxide to give a pH of 5. The solution was left standing overnight at −20° C., and the resulting precipitate was filtered off. The filtered precipitate was suspended in a water-methanol solvent system (50% of water and 50% of methanol), and the suspension was passed through a column packed with 3 liters of Amberlite XAD-2. The column was washed with 15 liters of water, and fractions obtained by elution with a solvent system (85% of methanol and 15% of water) were combined, concentrated and dried to provide 29.78 g of the end compound IIIa-1-9.

EXAMPLE 10

To a solution of 2.1 g (4.95 millimols) of thoroughly dried AI-77-B in 25 ml of pyridine, 3.3 g (6 millimols) of stearic anhydride was added at room temperature, and the solution was stirred at room temperature for 4 hours. After distilling the pyridine off in vacuum, 100 ml of water was added to the residue. The resulting precipitate was filtered off, and dried thoroughly. The solid product was washed three times with a total of 450 ml of hexane (150 ml each). The product was dissolved in 150 ml of chloroform, and 330 ml of p-toluenesulfonic acid was added to the solution, and stirred for 2 hours. To the solution, 100 ml of water was added to form separate layers, and the chloroform layer was separated from the aqueous layer and dried with sodium sulfate. Upon filtering the sodium sulfate off and concentrating the chloroform layer, 2.29 g of the end compound IIIa-1-11 resulted.

EXAMPLE 11

To a solution of 8.01 g (18.9 millimols) of thoroughly dried AI-77-B in 30 ml of pyridine, 5.97 g (37.8 millimols) of isobutyric anhydride was added at room temperature, followed by a 3-hr stirring at room temperature. After distilling the pyridine off in vacuum, 400 ml of water was added. The resulting precipitate was filtered off, and dried throughly. The dried product was dissolved in 80 ml of tetrahydrofuran, and 900 mg of p-toluenesulfonic acid was added to the solution at room temperature, and the solution was stirred for 1.5 hours. The solvent was distilled off under vacuum, the residue was dissolved in 200 ml of chloroform, and 300 ml of water was added to the solution to form separate layers. The chloroform layer was separated from the aqueous layer and dried with sodium sulfate. Filtering the sodium sulfate off and concentrating the chloroform layer gave 8.52 g of the end compound IIIa-1-4.

EXAMPLE 12

To a solution of 5 g (11.8 millimols) of thoroughly dried AI-77-B in 20 ml of pyridine, 2.19 g (12 millimols) of trichloroacetyl chloride was added under cooling with ice, followed by a 4-hr stirring under cooling with ice. After distilling the pyridine off in vacuum, the residue was dissolved in 2 ml of ethanol. When the solution was added to 100 ml of ice water, a powder resulted. The powder was filtered, washed twice with a total of 60 ml of water (30 ml each) and dried to give 4.54 g of the compound IIIa-1-12.

EXAMPLE 13

Two millimols of the IIIa-1-1 synthesized in Example 8 were dissolved in 4 ml of pyridine, and 30 millimols of propionic anhydride were added to the solution. After addition of 20 mg of zinc chloride, the solution was stirred at room temperature for 2 hours. The reaction mixture was poured into a large quantity of ice water, and the resulting percipitate was filtered off. The precipitate was washed twice with a total of 10 ml of water (5 ml each). The precipitate was suspended in a water-tetrahydrofuran solvent system (50% of water and 50% of tetrahydrofuran), and the suspension was passed through a column packed with 100 ml of Amberlite XAD-2. After washing the column with 500 ml of water, fractions were obtained by elution using tetrahydrofuran-water solvent system wherein, in sequential washings, the concentration of tetrahydrofuran was increased by 10% increments, beginning from 10% tetrahydrofuran. Fractions eluted with a concentration of 70% tetrahydrofuran were combined and concentrated to give 700 mg of IIIa-2-10.

EXAMPLE 14

Two millimols of the IIIa-1-12 synthesized in Example 12 were dissolved in 5 ml of pyridine, and 10 millimols of trichloroacetyl chloride were added to the solution, followed by a 1.5-hr stirring at room temperature. The reaction mixture was poured into a large quantity of ice water, and the resulting precipitate was filtered off. The precipitate was washed twice with a total of 20 ml of water (10 ml each). The precipitate was suspended in a water-tetrahydrofuran solvent system (50% water and 50% tetrahydrofuran), and the suspension was passed through a column packed with 100 ml of Amberlite XAD-2. After washing the column with 500 ml of water, fractions obtained by elution with a solvent system of 70% tetrahydrofuran and 30% water were combined and concentrated to give 680 mg of IIIa-2-1 in the same manner as in Example 13.

EXAMPLE 15

The compound IIIa-2-10 (1.5 millimols) synthesized in Example 13 was dissolved in 4 ml of pyridine, and after 20 millimols of isobutyric anhydride were added dropwise, the solution was stirred at 50° C. for 4 hours. After distilling the pyridine in vacuum, the residue was transferred into a large quantity of ice water. The resulting precipitate was washed three times with a total of 30 ml of water (10 ml each). The residue was suspended in a water-tetrahydrofuran solvent system (40% water and 60% tetrahydrofuran), and the suspension was passed through a column packed with 100 ml of Amberlite XAD-2. After washing the column with 500 ml of water, fractions obtained by elution with a solvent system of 70% tetrahydrofuran and 30% water were combined and concentrated to give 712 mg of IIIa-3-2 in the same manner as in Example 13.

EXAMPLE 16

The compound IIIa-2-1 (1.5 millimols) synthesized in Example 14 was dissolved in 4 ml of pyridine, and after 20 millimols of acetic anhydride were added dropwise, the solution was stirred at 50° C. for 4 hours. After distilling the pyridine in vacuum, the residue was transferred into a large quantity of ice water. The resulting precipitate was washed three times with a total of 30 ml of water (10 ml each). The residue was suspended in a water-tetrahydrofuran solvent system (40% water and 60% tetrahydrofuran), and the suspension was passed through a column packed with 100 ml of Amberlite XAD-2. After washing the column with 500 ml of water, fractions obtained by elution with a solvent system of 70% tetrahydrofuran and 30% water were combined and concentrated to give 670 mg of IIIa-3-10 in the same manner as in Example 13.

EXAMPLE 17

One millimol of IIIa-3-2 synthesized in Example 15 was dissolved in 10 ml of methylene chloride which was just distilled. To the solution, 1.5 millimoles of triethyloxonium fluoroborate was added in an argon atmosphere, and the solution was stirred at room temperature for 4 hours. After distilling the methylenechloride in vacuum, 10 ml of dried ethanol was added to the residue, and under cooling with ice, 2 millimols of sodium boronhydride was added, and following a 10 minute stirring, the excess sodium boronhydride was decomposed with ethanol saturated with hydrogen chloride gas. After evaporation to dryness in vacuum, the resulting solid product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 60% tetrahydrofuran were combined and concentrated to give 150 mg of IIIa-20-2.

EXAMPLE 18

The compound IIIa-2-10 (1.5 millimols) synthesized in Example 13 was dissolved in 10 ml of methylene chloride, and after 15 millimols of diazomethane in ether were added, the solution was stirred overnight at room temperature. The excess diazomethane was removed with acetic acid, and the reaction mixture was evaporated to dryness in vacuum. The residue was suspended in a water-tetrahydrofuran solvent system (40% water and 60% tetrahydrofuran), and the suspension was passed through a column packed with 100 ml of Amberlite XAD-2. After washing with 500 ml of water, the column was eluted using a tetrahydrofuran-water solvent system in the same manner as in Example 13. Fractions eluted with a concentration of 60% tetrahydrofuran were combined and concentrated to give 630 mg of IIIa-6-12.

EXAMPLE 19

One millimol of the compound IIIa-6-12 synthesized in Example 18 was dissolved in 10 ml of methylene chloride, and after 1.5 millimols of triethyloxonium fluoroborate were added in an argon atmosphere, the solution was stirred at room temperature for 4 hours. After distilling the methylene chloride off in vacuum, 10 ml of dried ethanol was added, and under cooling with ice, 2 millimols of sodium boronhydride were added, and following a 10-minute stirring, the excess sodium boronhydride was decomposed with ethanol saturated with hydrogen chloride gas. After evaporation to dryness in vacuum, the resulting solid product was suspended in a water-tetrahydrofuran solvent system (40% water and 60% tetrahydrofuran), and the suspension was passed through a column packed with 60 ml of Amberlite XAD-2. After washing with 300 ml of water, the column was eluted using a tetrahydrofuran-water solvent system in the same manner as in Example 13. Fractions eluted with a concentration of 60% tetrahydrofuran were combined and concentrated to give 85 mg of IIIa-23-11

EXAMPLE 20

The compound IIIa-2-10 (1.5 millimols) synthesized in Example 13 was dissolved in 10 ml of methylene chloride which was just distilled. To the solution, 1.5 millimols of triethyloxonium fluoroborate was added in an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, the excess sodium boronhydride was decomposed with ethanol saturated with hydrogen chloride gas. After evaporation to dryness in vacuum, the resulting solid product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 50% tetrahydrofuran were combined and concentrated to give 325 mg of IIIa-19-9.

EXAMPLE 21

Three millimols of IIIa-1-1 synthesized in Example 8 were dissolved in 50 ml of methanol, and after 30 millimols of diazobutane in ether were added at room temperature, the solution was stirred overnight. The excess diazobutane was removed with acetic acid, and the reaction mixture was evaporated to dryness in vacuum. The dried product was dissolved in 5 ml of methanol and a spot of the solution was placed on twenty-four silica gel plates (TLC PSC-Fertigplatten KIESELGEL 60F-254 of Merck & Co., Inc., Art. 5717, 20 cm×20 cm×2 mm) and developed with a methanol-chloroform (10:1) solvent system. Portions of Rf=0.52 (UV absorption observed, but no fluorescence observed) were combined, dissolved in 500 ml of methanol and stirred for 30 minutes. After filtering the silica gel, methanol was concentrated to give 800 mg of IIIa-5-3.

EXAMPLE 22

Five millimols of IIIa-1-12 synthesized in Example 12 were dissolved in a solvent comprising 20 ml of methanol and 80 ml of chloroform. After the addition of 30 millimols of diazoethane in ether at room temperature, the solution was stirred for one hour. After excess diazoethane was removed with acetic acid, the solvent was distilled off under vacuum and the residue was suspended in a water-methanol solvent system (50% water and 50% methanol). The suspension was passed through a column packed with 300 ml of Amberlite XAD-2. After washing with one liter of water, the column was washed using a methanol-water solvent system wherein, in sequential washings, the concentration of methanol was increased by 10% increments, beginning from 10% methanol. Fractions eluted with a concentration of 90% methanol were combined, concentrated and dried to give 2.72 g of the compound IIIa-5-13.

EXAMPLE 23

One millimol of IIIa-5-3 synthesized in Example 21 was dissolved in 15 ml of methylene chloride, and after the addition of 1.2 millimols of diazomethane in ether, 0.5 ml of a boron trifluoride etherate (product of Wako Pure Chemical Industries, Ltd.) which was just distilled was added to the solution. The solution was then stirred overnight. After removing excess diazomethane with acetic acid, the reaction mixture was poured into a large quantity of ice water, and the resulting precipitate was filtered off. The precipitate was washed twice with a total of 10 ml of water (5 ml each). The residue was suspended in a water-tetrahydrofuran solvent system (40% water and 60% tetrahydrofuran), and the suspension was passed through a column of 70 ml of Amberlite XAD-2. After washing with 500 ml of water, the column was eluted using a tetrahydrofuran-water solvent system in the same manner as in Example 13. Fractions eluted with a concentration of 65% tetrahydrofuran were combined and concentrated to give 632 mg of IIIa-7-16.

EXAMPLE 24

One millimol of IIIa-5-13 synthesized in Example 22 was dissolved in 15 ml of methylene chloride, and after the addition of 1.2 millimols of diazopropane in ether, 0.5 ml of a boron trifluoride etherate (product of Wako Pure Chemical Industries, Ltd.) which was just distilled was added to the solution. The solution was then stirred overnight. After removing excess diazopropane with acetic acid, the reaction mixture was poured into a large quantity of ice water, and the resulting precipitate was filtered off. The precipitate was washed twice with a total of 10 ml of water (5 ml each). The residue was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 65% tetrahydrofuran were combined and concentrated to give 670 mg of IIIa-7-17.

EXAMPLE 25

One millimol of IIIa-7-16 synthesized in Example 23 was dissolved in 10 ml of methylene chloride which was just distilled, and after the addition of 1.5 millimols of triethyloxonium fluoroborate in an argon atmosphere, the solution was stirred at room temperature for 4 hours. After the methylene chloride was distilled off in vacuum, 10 ml of dried ethanol was added, and under cooling with ice, 2 millmols of sodium boronhydride was added, and following a 10-minute stirring, excess sodium boronhydride was decomposed with ethanol saturated with hydrogen chloride gas. After evaporation to dryness in vacuum, the resulting solid product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner in Example 13. Fractions eluted with a concentration of 70% tetrahydrofuran were combined and concentrated to give 230 mg of IIIa-24-16.

EXAMPLE 26

Four millimols of IIIa-5-5 synthesized by the method of Example 21 were dissolved in 40 ml of methylene chloride which was just distilled. To the solution, 6 millimols of triethyloxonium fluoroborate was added in an argon atmosphere, and the solution was stirred at room temperature for 4 hours. After distilling the methylene chloride off in vacuum, 40 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was suspended in a water-methanol solvent system (80% water and 20% tetrahydrofuran), and the suspension was passed through a column packed with 200 ml of Amberlite XAD-2. After washing with 2 l of water, the column was eluted using a methanol-water solvent system in the same manner as in Example 22. Fractions eluted with a concentration of 40% methanol were combined and concentrated to give 500 mg of IIIa-22-5.

EXAMPLE 27

One millimol of IIIa-5-3 synthesized in Example 21 was dissolved in 10 ml of methylene chloride which was just distilled. To the solution, 1.5 millimols of triethyloxonium fluoroborate was added to an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was suspended in a water-methanol solvent system (80% water and 20% methanol), and the suspension was passed through a column packed with 70 ml of Amberlite XAD-2. After washing with 500 ml of water, the column was eluted using a methanol-water solvent system in the same manner as in Example 22. Fractions eluted with a concentration of 50% methanol were combined and concentrated to give 103 mg of IIIa-22-3.

EXAMPLE 28

Ten millimols of IIIa-1-1 synthesized in Example 8 were dissolved in 200 ml of methanol. To the solution, 20 millimols of phenyl diazomethane were added at room temperature, and the solution was stirred for 3 hours. Excess phenyl diazomethane was converted to benzyl acetate with acetic acid. The reaction mixture was evaporated to dryness in vacuum, and the residue was washed with 20 ml of ether. The residue was dried thoroughly, and the dried product was dissolved in 200 ml of methylene chloride. To the solution, first 50 millimols of diazomethane in ether, then 5 ml of boron trifluoride etherate (product of Wako Pure Chemical Industries, Ltd.) were added, and the mixture was stirred overnight at room temperature. Excess diazomethane was removed with acetic acid, and the solvent was removed in vacuum. The residue was put in a large quantity of ice water, and the resulting precipitate was filtered off. The precipitate was washed twice with a total of 100 ml of water (50 ml each), and the residue was dried thoroughly. The dried solid was dissolved in 30 ml of methanol, and after addition of 500 mg of Pd-C (10%), the solution was shaken with hydrogen gas at atmospheric pressure and room temperature. The reaction was completed in 20 minutes, Pd-C was filtered off, and the solvent was distilled off in vacuum. The residue was suspended in a water-methanol solvent system (40% water and 60% methanol), and the suspension was passed through a column packed with 300 ml of Amberlite XAD-2. The column was eluted using a methanol-water solvent system in the same manner as in Example 22. Fractions eluted with a concentration of 50% methanol were combined and concentrated to give 820 mg of IIIa-8-9.

EXAMPLE 29

One millimol of IIIa-8-9 synthesized in Example 28 was dissolved in 5 ml of pyridine, and after 20 millimols of isobutyric anhydride were added dropwise, the solution was stirred at 50° C. for 4 hours. After distilling pyridine off in vacuum, the residue was transferred into a large quantity of ice water. The resulting precipitate was washed three times with a total of 30 ml of water (10 ml each) and the residue was suspended in a water-tetrahydrofuran solvent system (40% water and 60% tetrahydrofuran). The suspension was passed through a column packed with 100 ml of Amberlite XAD-2. After washing with 500 ml of water, the column was eluted in the same manner as in Example 13. The fractions eluted with a solvent system of 70% tetrahydrofuran and 30% water were combined and concentrated to give 420 mg of IIIa-9-9.

EXAMPLE 30

The compound IIIa-9-9 (0.7 millimols) synthesized in Example 29 was dissolved in 7 ml of methylene chloride which was just distilled. To the solution, 1 millimol of triethyloxonium fluoroborate was added in an argon atmosphere, and the solution was stirred at room temperature for 4 hours. After distilling the methylene chloride off in vacuum, 7 ml of dried ethanol was added to the residue, and under cooling with ice, 1.4 millimols of sodium boronhydride was added, and following a 10-minute stirring, the excess sodium boronhydride was decomposed with ethanol saturated with hydrogen chloride gas. After evaporation to dryness in vacuum, the resulting solid product was suspended in a water-tetrahydrofuran solvent system (40% water and 60% tetrahydrofuran), and the suspension was passed through a column packed with 50 ml of Amberlite XAD-2. After washing with 400 ml of water, the column was eluted using a tetrahydrofuran-water solvent system in the same manner as in Example 13. Fractions eluted with concentration of 60% tetrahydrofuran were combined and concentrated to give 120 mg of IIIa-26-9.

EXAMPLE 31

One millimol of IIIa-8-9 synthesized in Example 28 were dissolved in 10 ml of methylene chloride which was just distilled. To the solution, 1.5 millimols of triethyloxonium fluoroborate were added in an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 40% tetrahydrofuran were combined and concentrated to give 180 mg of IIIa-25-9.

EXAMPLE 32

Ten millimols of IIIa-1-1 synthesized in Example 8 were put in 30 ml of pyridine, and 20 millimols of benzyloxycarbonyl chloride were added to the mixture. The solution was stirred at room temperature for 1.5 hours. The reaction mixture was transferred into a large quantity of ice water, and the resulting precipitate was filtered off. The precipitate was washed twice with a total of 100 ml of water (50 ml each). It was then washed with 50 ml of ether, and thoroughly dried. The dry solid was dissolved in 40 ml of pyridine, and after dropwise addition of 100 millimols of propionic anhydride, the solution was stirred at 50° C. for 4 hours. After the pyridine was distilled off in vacuum, the residue was put into a large quantity of ice water. The resulting precipitate was washed three times with a total of 300 ml of water (100 ml each) and the residue was dried thoroughly. The dry product was dissolved in 30 ml of methanol, and after adding 550 mg of Pd-C (10%), the solution was shaken with hydrogen gas at atmospheric pressure and room temperature. The reaction was completed in one hour, Pd-C was filtered off, and the solvent was distilled off in vacuum. The residue was suspended in a water-tetrahydrofuran solvent system (40% water and 60% tetrahydrofuran), and the suspension was passed through a column packed with 300 ml of Amberlite XAD-2. The column was eluted using a tetrahydrofuran-water solvent system in the same manner as in Example 13. Fractions eluted with a concentration of 40% tetrahydrofuran were combined and concentrated to give 2.3 g of IIIa-4-1.

EXAMPLE 33

Five millimols of IIIa-1-12 synthesized in Example 12 were put in 15 ml of pyridine, and 10 millimols of benzyloxycarbonyl chloride were added to the mixture. The solution was stirred at room temperature for 2 hours. The reaction mixture was transferred into a large quantity of ice water, and the resulting precipitate was filtered off. The precipitate was washed twice with a total of 60 ml of water (30 ml each). It was then washed with 30 ml of ether and thoroughly dried. The dry solid was dissolved in 25 ml of pyridine, and after dropwise addition of 50 millimols of trichloroacetyl chloride, the solution was stirred at 50° C. for 4 hours. After the pyridine was distilled off in vacuum, the residue was put into a large quantity of ice water. The resulting precipitate was washed three times with a total of 150 ml of water (50 ml each) and the residue was dried thoroughly. The dry product was dissolved in 15 ml of methanol, and after adding 300 mg of Pd-C (10%), the solution was shaken with hydrogen gas at atmospheric pressure and room temperature. The reaction was completed in one hour, Pd-C was filtered off, and the solvent was distilled off in vacuum. The residue was dissolved in 50 ml of chloroform. To the solution, first 20 millimols of diazomethane in ether, then 2 ml of boron trifluoride etherate (product of Wako Pure Chemical Industries, Ltd.) were added, and the solution was stirred overnight at room temperature. Excess diazomethane was removed with acetic acid, and the solvent was removed in vacuum. The residue was suspended in a solvent comprising 10 ml of methanol and 20 ml of water, and 1 N aqueous sodium hydroxide was added to the suspension until the pH was 12. When the suspension was stirred at room temperature, its pH became lower than 12, so that the same alkali was further added until the pH reached 12. When the pH no longer dropped below 12, 1 N hydrochloric acid was added to the suspension to adjust its pH to 7. The resulting suspension was passed through a column packed with 150 ml of Amberlite XAD-2. After washing with 500 ml of water, the column was eluted using a methanol-water solvent system in the same manner as in Example 22. Fractions eluted with a concentration of 50% methanol were combined and concentrated. The concentrate was dissolved in 10 ml of methanol saturated with hydrogen chloride, and the solution was stirred for 30 minutes under cooling with ice. The solvent was distilled off in vacuum and the residue was dried thoroughly to give 920 mg of IIIa-16-1.

EXAMPLE 34

One millimol of IIIa-1-1 synthesized in Example 8 was dissolved in 10 ml of methylene chloride which was just distilled. To the solution, 1.5 millimols of triethyloxonium fluoroborate was added in an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was dissolved in a water-methanol (1:4) solvent, and the solution was passed through a column packed with 70 ml of Amberlite XAD-2. After washing with 500 ml of water, the column was eluted using a methanol-water solvent (water contained 10% of 1 N hydrochloric acid) in the same manner as in Example 22. Fractions eluted with a concentration of 45% methanol were combined and concentrated to give 220 mg of IIIa-18-1.

EXAMPLE 35

One millimol of IIIa-1-2 synthesized by the method of Example 8 was dissolved in 10 ml of methylene chloride which was just distilled. To the solution, 1.5 millimols of triethyloxonium fluoroborate was added in an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was dissolved in a water-methanol (1:4) solvent, and the solution was passed through a column packed with 70 ml of Amberlite XAD-2. After washing with 500 ml of water, the column was eluted using a methanol-water solvent system (water contained 10% of 1 N hydrochloric acid) in the same manner as in Example 22. Fractions eluted with a concentration of 50% methanol were combined and concentrated to give 210 mg of IIIa-18-2.

EXAMPLE 36

One millimol of IIIa-1-6 synthesized by the method of Example 8 was dissolved in 10 ml of methylene chloride which was just distilled. To the solution, 1.5 millimols of triethyloxonium fluoroborate was added in an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was dissolved in a water-methanol (1:4) solution, and the solution was passed through a column packed with 70 ml of Amberlite XAD-2. After washing with 500 ml of water, the column was eluted using a methanol-water solvent (water contained 10% of 1 N hydrochloric acid) in the same manner as in Example 22. Fractions eluted with a concentration of 55% methanol were combined and concentrated to give 215 mg of IIIa-18-6.

EXAMPLE 37

One millimol of IIIa-1-9 synthesized in Example 9 was dissolved in 10 ml of methylene chloride which was just distilled. To the solution, 1.5 millimols of triethyloxonium fluoroborate was added in an argon atmosphere, and the solution was stirred at room temperature for 4 hours. After distilling the methylene chloride off in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was dissolved in a water-methanol (1:4) solution, and the solution was passed through a column packed with 70 ml of Amberlite XAD-2. After washing with 500 ml of water, the column was eluted using a methanol-water solvent system (water contained 10% of 1 N hydrochloric acid) in the same manner as in Example 22. Fractions eluted with a concentration of 70% methanol were combined and concentrated to give 250 mg of IIIa-18-9.

EXAMPLE 38

One millimol of IIIa-1-11 synthesized in Example 10 was dissolved in 10 ml of methylene chloride which was just distilled. To the solution, 1.5 millimols of triethyloxonium fluoroborate was added in an argon atmosphere, and the solution was stirred at room temperature for 4 hours. After distilling the methylene chloride in vacuum, 10 ml of dried ethanol was added to the residue, and under cooling with ice, 2 millimols of sodium boronhydride was added, and following a 10-minute stirring, excess sodium boronhydride was decomposed with ethanol saturated with hydrogen chloride gas. After evaporation to dryness in vacuum, the resulting solid product was dissolved in a water-methanol (1:4) solution, and the solution was passed through a column packed with 70 ml of Amberlite XAD-2. After washing with 500 ml of water, the column was eluted using a tetrahydrofuran-water solvent system (water contained 10% of 1 N hydrochloric acid) in the same manner as in Example 13. Fractions eluted with a concentration of 50% tetrahydrofuran were combined and concentrated to give 230 mg of IIIa-18-11.

EXAMPLE 39

One millimol of IIIa-7-17 synthesized in Example 24 was suspended in a solvent comprising 2 ml of methanol and 4 ml of water, and 1 N aqueous sodium hydroxide was added to the suspension until the pH was 12. When the suspension was stirred at room temperature, its pH became lower than 12, so that the same alkali was further added until the pH reached 12. When the pH no longer dropped below 12, 1 N hydrochloric acid was added to the suspension to adjust its pH to 7. The resulting suspension was passed through a column packed with 30 ml of Amberlite XAD-2. After washing with 100 ml of water, the column was eluted using a methanol-water solvent system in the same manner as in Example 22. Fractions eluted with a concentration of 70% methanol were combined and concentrated. The concentrate was dissolved in 2 ml of methanol saturated with hydrogen chloride, and the solution was stirred for 30 minutes under cooling with ice. The solvent was distilled off in vacuum and the residue was dried thoroughly to give 370 mg of IIIa-15-8.

EXAMPLE 40

Five millimols of IIIa-5-13 synthesized in Example 22 were suspended in a solvent comprising 10 ml of methanol and 20 ml of water, and 1 N aqueous sodium hydroxide was added to the suspension until the pH was 12. When the suspension was stirred at room temperature, its pH became lower than 12, so that the same alkali was further added until the pH reached 12. When the pH no longer dropped below 12, 1 N hydrochloric acid was added to the suspension to adjust its pH to 7. The resulting suspension was passed through a column packed with 150 ml of Amberlite XAD-2. After washing with 500 ml of water, the column was eluted using a methanol-water solvent system in the same manner as in Example 22. Fractions eluted with a concentration of 60% methanol were combined and concentrated. The concentrate was dissolved in 10 ml of methanol saturated with hydrogen chloride, and the solution was stirred for 30 minutes under cooling with ice. The solvent was distilled off in vacuum and the residue was dried thoroughly to give 1.89 g of IIIa-13-2.

EXAMPLE 41

One millimol of IIIa-6-13 synthesized by the method of Example 18 was subjected to the reaction of detrichloroacetylation described in Example 39. The reaction product was purified by the method used in Example 39, and fractions eluted at a methanol concentration of 70% were combined and concentrated. The concentrate was dissolved in 2 ml of methanol saturated with hydrogen chloride, and the solution was stirred for 30 minutes under cooling with ice. The solvent was distilled off and the residue was dried thoroughly to give 320 mg of IIIa-14-9.

EXAMPLE 42

Five millimols of IIIa-1-12 synthesized in Example 12 were dissolved in 100 ml of methanol. To the solution, 10 millimols of phenyl diazomethane were added at room temperature, and the solution was stirred for 3 hours. Excess phenyl diazomethane was converted to benzyl acetate with acetic acid. The reaction mixture was evaporated to dryness in vacuum, and the residue was washed with 15 ml of ether. The residue was dried thoroughly, and the dried product was dissolved in 100 ml of methylene chloride. To the solution, first 25 millimols of diazomethane in ether, then 2.5 ml of boron trifluoride etherate (product of Wako Pure Chemical Industries, Ltd.) were added, and the mixture was stirred overnight at room temperature. Excess diazomethane was removed with acetic acid, and the solvent was removed in vacuum. The residue was put in a large quantity of ice water, and the resulting precipitate was filtered off. The precipitate was washed twice with a total of 50 ml of water (25 ml each), and the residue was dried thoroughly. The dried solid was dissolved in 15 ml of methanol, and after addition of 250 mg of Pd-C (10%), the solution was shaken with hydrogen gas at atmospheric pressure and room temperature. The reaction was completed in 20 minutes, Pd-C was filtered off, and the solvent was distilled off in vacuum. The residue was dried thoroughly and dissolved in 15 ml of pyridine. After 100 millimols of propionic anhydride was added dropwise, the solution was stirred at 50° C. for 4 hours. The pyridine was distilled off in vacuum, and the residue was put into a large quantity of ice water. The resulting precipitate was washed three times with a total of 450 ml of water (150 ml each). The precipitate was then suspended in a solvent comprising 10 ml of methanol and 20 ml of water, and 1 N aqueous sodium hydroxide was added to the suspension until the pH was 12. When the suspension was stirred at room temperature, its pH became lower than 12, so that the same alkali was further added until the pH reached 12. When the pH no longer dropped below 12, 1 N hydrochloric acid was added to the suspension to adjust its pH to 7. The resulting suspension was passed through a column packed with 150 ml of Amberlite XAD-2. After washing with 500 ml of water, the column was eluted using a methanol-water solvent system in the same manner as in Example 22. Fractions eluted with a concentration of 70% methanol were combined and concentrated. The concentrate was dissolved in 10 ml of methanol saturated with hydrogen chloride, and the solution was stirred for 30 minutes under cooling with ice. The solvent was distilled off in vacuum and the residue was dried thoroughly to give 830 mg of IIIa-17-5.

EXAMPLE 43

One millimol of IIIa-2-1 synthesized in Example 14 was suspended in a solvent comprising 2 ml of methanol and 4 ml of water, and 1 N aqueous sodium hydroxide was added to the suspension until the pH was 12. When the suspension was stirred at room temperature, its pH became lower than 12, so that the same alkali was further added until the pH reached 12. When the pH no longer dropped below 12, 1 N hydrochloric acid was added to the suspension to adjust its pH to 7. The resulting suspension was passed through a column packed with 150 ml of Amberlite XAD-2. After washing with 500 ml of water, the column was eluted using a methanol-water solvent system in the same manner as in Example 22. Fractions eluted with a concentration of 50% methanol were combined and concentrated. The concentrate was dissolved in 2 ml of methanol saturated with hydrogen chloride, and the solution was stirred for 30 minutes under cooling with ice. The solvent was distilled off in vacuum and the residue was dried thoroughly to give 400 mg of IIIa-12-1.

EXAMPLE 44

Five millimols of thoroughly dried AI-77-B were dissolved in 10 ml of pyridine. To the solution, 10 m mols of benzyloxycarbonyl chloride were added at room temperature, and the solution was stirred for 3 hours. After addition of 20 m mols of benzyloxycarbonyl chloride, the solution was stirred at room temperature for 1.5 hours. The reaction mixture was put into a large quantity of ice water, and the resulting precipitate was filtered off. The precipitate was washed twice with a total of 100 ml of water (50 ml each). It was then washed with 50 ml of ether and thoroughly dried. The dry solid was dissolved in 40 ml of pyridine, and after addition of 50 m mols of trichloroacetyl chloride, the solution was stirred at 50° C. for 4 hours. After the pyridine was distilled off in vacuum, the residue was put into a large quantity of ice water. The resulting precipitate was washed three times with a total of 150 ml of water (50 ml each), and the residue was dried thoroughly. The dry product was dissolved in 15 ml of methanol, and after adding 280 mg of Pd-C (10%), the solution was shaken with hydrogen gas at atmospheric pressure and room temperature. The reaction was completed in two hours, Pd-C was filtered off, and the solvent was distilled off in vacuum. The residue was suspended in a water-tetrahydrofuran solvent (40% water and 60% tetrahydrofuran), and the suspension was passed through a column packed with 150 ml of Amberlite XAD-2. The column was eluted using a tetrahydrofuran-water solvent system in the same manner as in Example 13. Fractions eluted with a concentration of 30% tetrahydrofuran were combined and concentrated to give 1.02 g of IIIa-12-9.

EXAMPLE 45

Five millimols of thoroughly dried AI-77-B were dissolved in 10 ml of pyridine. To the solution 10 m mols of benzyloxycarbonyl chloride were added at room temperature, and the solution was stirred for 3 hours. After the pyridine was distilled off in vacuum, the residue was washed twice with a total of 20 ml of water (10 ml each). It was then washed with 30 ml of ether and thoroughly dried. The dry solid was dissolved in 100 ml of methanol, and after addition of 10 m mols of phenyl diazomethane at room temperature, the solution was stirred for 3 hours. Excess phenyl diazomethane was converted to benzyl acetate with acetic acid. The reaction mixture was evaporated to dryness in vacuum, and the residue was washed with 10 ml of ether. The residue was dried thoroughly and the dry product was dissolved in 100 ml of methylene chloride. To the solution, first 10 m mols of diazoethane in ether, then 2.5 ml of boron trifluoride etherate (product of Wako Pure Chemical Industries, Ltd.) were added, and the solution was stirred overnight at room temperature. Excess diazoethane was removed with acetic acid, and the solvent was removed in vacuum. The residue was put into a large quantity of ice water, and the resulting precipitate was filtered off. The precipitate was washed twice with a total of 50 ml of water (25 ml each), and the residue was dried thoroughly. The dry product was dissolved in 15 ml of methanol, and following the addition of 280 mg of Pd-C (10%), the solution was shaken with hydrogen gas at atmospheric pressure and room temperature. The reaction was completed in two hours, Pd-C was removed, and the solvent was distilled off in vacuum. The residue was suspended in a water-tetrahydrofuran solvent system (40% water and 60% tetrahydrofuran), and the suspension was passed through a column packed with 150 ml of Amberlite XAD-2. The column was eluted using a tetrahydrofuran-water solvent system in the same manner as in Example 13. Fractions eluted with a concentration of 30% tetrahydrofuran were combined and concentrated to give 1.21 g of IIIa-16-7.

EXAMPLE 46

One millimol of IIIa-16-7 synthesized in Example 45 was put in 4 ml of pyridine, and after addition of 2 m mols of benzyloxycarbonyl chloride, the solution was stirred at room temperature for 3 hours. After the pyridine was distilled off in vacuum, the residue was washed twice with a total of 4 ml of water (2 ml each). It was then washed with 6 ml of ether and dried thoroughly. The dry product was put in 4 ml of pyridine, and after addition of 10 m mols of trichloroacetyl chloride, the solution was stirred at 50° C. for 4 hours. After pyridine was distilled off in vacuum, the residue was put into a large quantity of ice water. The resulting precipitate was washed three times with a total of 30 ml of water (10 ml each) and dried thoroughly. The dry product was dissolved in 3 ml of methanol. After adding 50 mg of Pd-C (10%), the solution was shaken with hydrogen gas at atmospheric pressure and room temperature. The reaction was completed in one hour, Pd-C was filtered off, and the solvent was distilled off in vacuum. The residue was suspended in a water-tetrahydrofuran solvent system (40% water and 60% tetrahydrofuran), and the suspension was passed through a column packed with 30 ml of Amberlite XAD-2. The column was eluted using a tetrahydrofuran-water solvent system in the same manner as in Example 13. Fractions eluted with a concentration of 40% tetrahydrofuran were combined and concentrated to give 210 mg IIIa-17-6.

EXAMPLE 47

One millimol of thoroughly dried AI-77-B was dissolved in 4 ml of pyridine, and after adding 2 m mol of benzyloxycarbonyl chloride, the solution was stirred at room temperature for 3 hours. After distilling pyridine off in vacuum, the residue was washed twice with a total of 4 ml of water (2 ml each). It was washed with 6 ml of ether and dried thoroughly. The dry product was put in 4 ml of pyridine, and 15 m mol of acetic anhydride was added. After addition of 10 mg of zinc chloride, the solution was stirred at room temperature for 2 hours. The reaction mixture was poured into a large quantity of ice water, and the resulting precipitate was filtered off. The precipitate was washed twice with a total of 4 ml of water (2 ml each). The precipitate was dissolved in 3 ml of methanol, and followed addition of 50 mg of Pd-C (10%), the solution was shaken with hydrogen gas at atmospheric pressure and room temperature. The reaction was completed in one hour, Pd-C was filtered off, and the solvent was distilled off in vacuum. The residue was suspended in a water-tetrahydrofuran solvent (40% water and 60% tetrahydrofuran), and the suspension was passed through a column packed with 30 ml of Amberlite XAD-2. The column was eluted using a tetrahyrofuran-water solvent system in the same manner as in Example 13. Fractions eluted with a concentration of 30% tetrahydrofuran were combined and concentrated to give 230 mg of IIIa-10-1.

EXAMPLE 48

One millimol of thoroughly dried AI-77-B was dissolved in 4 ml of pyridine, and after adding 2 m mol of benzyloxycarbonyl chloride, the solution was stirred at room temperature for 3 hours. After distilling pyridine off in vacuum, the residue was washed twice with a total of 4 ml of water (2 ml each). It was washed with 6 ml of ether and dried thoroughly. The dry product was put in 4 ml of pyridine, and 15 m mol of acetic anhydride was added. After addition of 10 mg of zinc chloride, the solution was stirred at room temperature for 2 hours. The reaction mixture was poured into a large quantity of ice water, and the resulting precipitate was filtered off. The precipitate was washed twice with a total of 4 ml of water (2 ml each) and dried thoroughly. The dry product was put in 4 ml of pyridine, and after addition of 10 m mol of butyric anhydride, the solution was stirred at 50° C. for 4 hours. After pyridine was distilled off in vacuum, the residue was placed into a large quantity of ice water. The resulting precipitate was washed three times with a total of 30 ml of water (10 ml each) and dried thoroughly. The dry product was dissolved in 3 ml of methanol, and following addition of 50 mg of Pd-C (10%), the solution was shaken with hydrogen gas at atmospheric pressure and room temperature. The reaction was completed in one hour, Pd-C was filtered off, and the solvent was distilled off under vacuum. The residue was suspended in a water-tetrahydrofuran solvent system (40% water and 60% tetrahydrofuran), and the suspension was passed through a column packed with 30 ml of Amberlite XAD-2. The column was eluted using a tetrahydrofuran-water solvent system in the same manner as in Example 13. Fractions eluted with concentration of 40% tetrahydrofuran were combined and concentrated to give 270 mg of IIIa-11-6.

EXAMPLE 49

One millimol of thoroughly dried AI-77-B was dissolved in 4 ml of pyridine, and after adding 2 m mol of benzyloxy carbonyl chloride, the solution was stirred at room temperature for 3 hours. After distilling pyridine off in vacuum, the residue was washed twice with a total of 4 ml of water (2 ml each). It was washed with 6 ml of ether and dried thoroughly. The dry product was put in 4 ml of pyridine, and 15 m mol of acetic anhydride was added. After addition of 10 mg of zinc chloride, the solution was stirred at room temperature for 2 hours. The reaction mixture was poured into a large quantity of ice water, and the resulting precipitate was filtered off. It was washed twice with a total of 4 ml of water (2 ml each), and dried thoroughly. The dry product was dissolved in a solvent comprising 4 ml of methanol and 16 ml of chloroform. After adding 6 m mol of diazoethane in ether at room temperature, the solution was stirred for one hour. Excess diazoethane was removed with acetic acid, and the solvent was distilled off under vacuum. The residue was dissolved in 3 ml of methanol, and after adding 50 mg of Pd-C (10%), the solution was shaken with hydrogen gas at atmospheric pressure and room temperature. The reaction was completed in one hour, Pd-C was filtered off, and the solvent was distilled off under vacuum. The residue was suspended in a water-tetrahydrofuran solvent system (40% water and 60% tetrahydrofuran), and the suspension was passed through a column packed with 30 ml of Amberlite XAD-2. The column was eluted using a tetrahydrofuran-water solvent system in the same manner as in Example 13. Fractions eluted with a concentration of 50% tetrahydrofuran were combined and concentrated to give 273 mg of IIIa-14-1.

EXAMPLE 50

Two millimols (848 mg) of thoroughly dried AI-77-B were placed in a 50-ml glass pressure container, and 10 ml of N,N-dimethylformamide was added to dissolve the AI-77-B. After adding 10 m mol of methyl iodine, the container was closed and shaken vigorously for one hour at room temperature. Another 10 m mol of methyl iodide was added, and a reaction was performed in the same manner. Methyl iodide was again added in an amount of 10 m mol, and after vigorous shaking of the container for 24 hours, the solvent (N,N-dimethyl formamide) and unreacted methyl iodide were distilled off under vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.38 (UV absorption observed, purplish red in Nin- hydrin reaction) were combined, placed in 200 ml of methanol and the solution was stirred for 30 minutes. After filtering the silica gel, methanol was concentrated to give 72 mg of IIIa-27-1.

EXAMPLE 51

Thoroughly dried AI-77-B (1.2 m mol) was dissolved in 5 ml of N,N-dimethyl formamide, after adding 3 m mols of ethyl iodide, the solution was stirred at room temperature for 2 hours. Three millimols of ethyl iodide were added four times at an interval of one hour. The solvent and excess ethyl iodide were distilled off the reaction mixture under vacuum. The residue was dissolved in 2 ml of methanol, and spots of the solution were placed on ten silica gel plates (TLCPSC-Fertigplatten KIESELGEL 60F-254 of Merck & Co., Inc., Art. 5717 20 cm×20 cm×2 mm), developed with a solvent system of methanol and chloroform (1:10), portions having Rf=0.40 (UV absorption observed, purplish red in Ninhydrin (trademark) reaction) were combined, placed in 100 ml of methanol, and the solution was stirred for 30 minutes. After filtering the silica gel, methanol was concentrated to give 70 mg of IIIa-18-1.

EXAMPLE 52

Two millimols (778 mg) of thoroughly dried AI-77-F were dissolved in 4 ml of pyridine, and 40 m mol of acetic anhydride was added to the solution. After adding 20 mg of zinc chloride, the solution was stirred at room temperature for 2 hours. The reaction mixture was poured into a large quantity of ice water, and the resulting precipitate was filtered off. It was washed twice with a total of 10 ml of water (5 ml each) and dried. The dry product was dissolved in 2 ml of methanol, and spots of the solution were placed on fifteen silica gel plates (TLPSC-Fertigplatten KIESELGEL 60F-254 of Merck & Co., Inc., Art. 5717 20 cm×20 cm×2 mm), developed with a solvent system of chloroform and methanol (30:1), and portions having Rf=0.70 (UV absorption observed) were combined, placed in 100 ml of methanol, and the solution was stirred for 20 minutes. After filtering the silica gel, the methanol was concentrated to give 520 mg of IVa-1-1.

EXAMPLE 53

Compound IVa-1-12 was synthesized by repeating the procedure of Example 52 except that acetic anhydride was replaced by trichloroacetyl chloride. Two millimole of the compound was dissolved in 4 ml of pyridine, and after adding 26 m mol of acetic anhydride, the solution was stirred at 50° C. for 3 hours. After distilling pyridine off in vacuum, the residue was transferred into a large quantity of ice water. The resulting precipitate was washed three times with a total of 30 ml of water (10 ml each) and dried. The dry product was suspended in a solvent comprising 4 ml of methanol and 8 ml of water, and 1 N aqueous sodium hydroxide was added to the solution until its pH reached 12. When the solution was stirred at room temperature, the pH became lower than 12, so that the same alkali was further added to obtain a pH of 12. When the pH no longer dropped below 12, 1 N hydrochloric acid was added to adjust the pH to 7. The solution was then passed through a column packed with 60 ml of Amberlite XAD-2. After washing with 200 ml of water, the column was eluted usin a tetrahydrofuran-water solvent system in the same manner as in Example 13. Fractions eluted with a concentration of 50% tetrahydrofuran were combined and concentrated. The concentrate was dissolved in 4 ml of methanol saturated with hydrogen chloride, and the solution was stirred for 30 minutes under cooling with ice. The solvent was distilled off under vacuum and the residue was dried thoroughly to give 530 mg of IVa-3-1.

EXAMPLE 54

One millimol of IVa-1-1 synthesized in Example 52 was dissolved in 2 ml of pyridine, and after adding 13 m mols of propionic anhydride, the solution was stirred at 50° C. for 3 hours. After distilling pyridine off in vacuum, the residue was dissolved in 1 ml of methanol, and spots of the solution were placed on ten silica gel plates (TLCPSC-Fertigplatten KIESELGEL 60F-254 of Merck & Co., Inc., Art. 5717, 20 cm×20 cm×2 mm), developed with a solvent system of chloroform and methanol (50:1), portions having Rf=0.60 (UV absorption observed) were combined, placed in 50 ml of methanol, and the solution was stirred for 20 minutes. When the silica gel was filtered off and methanol concentrated, 305 mg of IVa-2-2 resulted.

EXAMPLE 55

One millimol of IVa-1-1 synthesized in Example 52 was dissolved in 5 ml of chloroform, and after adding 10 m mol of diazomethane in ether at room temperature, the solution was stirred overnight. Excess diazomethane was removed with acetic acid, and the reaction mixture was evaporated to dryness in vacuum. The dry product was dissolved in 1 ml of methanol, and spots of the solution were placed on ten silica gel plates (TLCPSC-Fertigplatten KIESELGEL 60F-254 of Merck & Co., Inc., Art. 5717, 20 cm×20 cm×2 mm), developed with a solvent system of chloroform and methanol (50:1), portions having Rf=0.60 (UV absorption observed) were combined, placed in 50 ml of methanol, and the solution was stirred for 20 minutes. When the silica gel was filtered off and methanol concentrated, 270 mg of IVa-5-1 resulted.

EXAMPLE 56

Two millimols (778 mg) of thoroughly dried AI-77-F were dissolved in 10 ml of chloroform, and after adding 15 m mols of diazoethane in ether at room temperature, the solution was stirred for one hour. Excess diazoethane was removed with acetic acid, and the reaction mixture was evaporated to dryness under vacuum. The dry product was dissolved in 2 ml of methanol, spots of the solution were placed on fifteen silica gel plates (TLCPSC-Fertigplatten KIESELGEL 60F-254 of Merck & Co., Inc., Art. 5717, 20 cm×20 cm×2 mm), developed with a solvent system of chloroform and methanol (40:1), portions having Rf=0.70 (UV absorption observed) were combined, placed in 100 ml of methanol, and the solution was stirred for 20 minutes. When the silica gel was filtered off and methanol concentrated, 680 mg of IVa-4-2 resulted.

EXAMPLE 57

One millimol of IVa-4-2 synthesized in Example 56 was dissolved in 10 ml of methylene chloride, and to the solution, first 5 m mols of diazobutane in ether, then 0.5 ml of boron trifluoride etherate (product of Wako Pure Chemical Industries, Ltd.) were added, and the solution was stirred overnight at room temperature. Excess diazobutane was removed with acetic acid, and the reaction mixture was evaporated to dryness under vacuum. The dry product was dissolved in 1 ml of methanol, and spots of the solution were placed on ten silica gel plates (TLCPSC-Fertigplatten KIESELGEL 60F-254 of Merck & Co., Inc., Art. 5717, 20 cm×20 cm×2 mm), developed with a solvent system of chloroform and methanol (50:1), portions having Rf=0.70 (UV absorption observed) were combined, placed in 50 ml of methanol, and the solution was stirred for 20 minutes. When the silica gel was filtered off and methanol concentrated, 290 mg of IVa-6-5 resulted.

EXAMPLE 58

Two millimols of IVa-6-4 synthesized by the method of Example 57 were dissolved in 10 ml of methanol, and after adding 100 mg of Pd-C (10%), the solution was shaken with hydrogen gas at atmospheric pressure and at room temperature. The reaction was completed in 20 minutes, Pd-C was filtered off, and the solvent was distilled off under vacuum. The residue was dissolved in 2 ml of methanol, spots of the solution were placed on fifteen silica gel plates (TLCPSC-Fertigplatten KIESELGEL 60F-254 of Merck & Co., Inc., Art. 5717, 20 cm×20 cm×2 mm), developed with a solvent system of chloroform and methanol (30:1), portions having Rf=0.65 (UV absorption observed) were combined, placed in 100 ml of methanol, and the solution was stirred for 20 minutes. When the silica gel was filtered off and methanol concentrated, 520 mg of IVa-7-8 resulted.

EXAMPLE 59

One millimol of IVa-7-8 synthesized in Example 58 was dissolved in 4 ml of pyridine, and after adding 10 m mols of acetic anhydride, the solution was stirred at 50° C. for 3 hours. After distilling pyridine off in vacuum, the residue was dissolved in 2 ml of methanol, and spots of the solution were placed on ten silica gel plates (TLCPSC-Fertigplatten KIESELGEL 60F-254 of Merck & Co., Inc., Art. 5717, 20 cm×20 cm×2 mm), developed with a solvent system of chloroform and methanol (50:1), portions having Rf=0.7 (UV absorption observed) were combined, placed in 50 ml of methanol, and the solution was stirred for 20 minutes. When the silica gel was filtered off and methanol concentrated, 240 mg of IVa-8-5 resulted.

EXAMPLE 60

Two millimols of IIIa-18-1 synthesized in Example 34 were dissolved in a solvent comprising 2 ml of methanol and 5 ml of water, and 1 N aqueous sodium hydroxide was added until the pH of the solution was 10 when the solution was stirred, the pH became lower than 10, so that the same alkali was further added to obtain a pH of 10. When the pH no longer dropped below 10, 1 N hydrochloric acid was added to adjust the pH to 7, and the resulting solution was purified on a column Amberlite XAD-2. After thorough washing with water, the column was eluted with a solvent of 50% methanol and 50% water (opening of gamma-lactone ring). The eluates were concentrated to give 820 mg of IIIb-18-1. The concentrate was dissolved in a solvent comprising 2 ml of methanol and 5 ml of water, and 1 N aqueous sodium hydroxide was added until the pH reached 12. When the solution was stirred, the pH became lower than 12, so that the same alkali was further added to obtain a pH of 12. When the pH no longer dropped below 12, 1 N hydrochloric acid was added to adjust the pH to 7, and the resulting solution was purified on a column of Amberlite XAD-2. After thorough washing with water, the column was eluted with a solvent of 30% methanol and 70% water. The eluates were concentrated to give 810 mg of IIIc-18-1. One millimol of IIIb-18-1 was dissolved in 5 ml of methanol, and after adding 1 ml of methanol saturated with hydrogen chloride, the solution was stirred for one hour under cooling with ice. When the solvent was distilled off, 400 mg of IIIa-18-1 resulted. By subjecting one millimol of IIIc-18-1 to the same treatment as above, 380 mg of IIIa-18-1 was formed.

EXAMPLE 61

Two millimols of thoroughly dried AI-77-A were placed in a pressure container. After adding 24 m mols of p-toluidine, the container was closed, and the solution was stirred for 10 minutes at 100° C. The reaction mixture was dissolved in 2 ml of methanol, and spots of the solution were placed on fifteen silica gel plates (TLCPSC-Fertigplatten KIESELGEL 60F-254 of Merck & Co., Inc., Art. 5717, 20 cm×20 cm×2 mm), developed with a solvent system of chloroform and methanol (8:1) portions having Rf=0.20 (UV absorption observed) were combined, placed in 100 ml of methanol, and the solution was stirred for 20 minutes. When the silica gel was filtered off and methanol concentrated, 300 mg of Vb-1-42 resulted.

EXAMPLE 62

One millimol of thoroughly dried AI-77-B was suspended in 10 ml of methylene chloride which was just distilled, and 3 m mols of triethyloxonium fluoroborate were added to the suspension. When the suspension was stirred for one hour at room temperature, it became transparent, and after it was stirred overnight, the solvent of methylene chloride was distilled off in vacuum. The residue was dissolved in 10 ml of ethanol, and under cooling with ice, 2 ml of ethanol saturated with ammonia was added. After a two-hour stirring, the temperature of the solution was restored to room temperature at which the reaction was continued for 3 days. The residue was dissolved in water, and the solution was passed through a column packed with 50 ml of Amberlite XAD-2. After washing with 100 ml of water, the column was eluted with a solvent system of 10% methanol and 90% water. Active fractions were combined and concentrated to give 300 mg of AI-77-A.

EXAMPLE 63

One millimol of IIIa-4-1 synthesized in Example 32 was dissolved in 10 ml of methylene chloride which was just distilled, and after 1.5 m mols of triethyloxonium fluoroborate was added in an argon atmosphere, the solution was stirred at room temperature for 4 hours. After methylene chloride was distilled off in vacuum, 10 ml of dried ethanol was added, and under cooling with ice, 2 m mols of sodium borohydride was added, and following a 10-minute stirring, excess sodium borohydride was decomposed with ethanol saturated with hydrogen chloride gas. The reaction mixture was evaporated to dryness, and the dry product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 60% tetrahydrofuran were combined and concentrated to give 160 mg of IIIa-21-9.

EXAMPLE 64

Two millimols of thoroughly dried IIIa-10-1 (synthesized in Example 47) were placed in a 50-ml glass pressure container, and 10 ml of N,N-dimethylformamide was added to dissolve the compound. After adding 10 m mols of methyl iodide, the container was closed, and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off under vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.40 (UV absorption observed, purplish red in Ninhydrin reaction) were combined, placed in 200 ml of methanol, and the solution was stirred for 30 minutes. After filtering the silica gel and concentrating methanol, 80 mg of IIIa-28-1 was formed.

EXAMPLE 65

Two millimols of IIIa-11-1 synthesized by the method of Example 48 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:20), portions having Rf=0.50 (UV absorption observed, purplish red in ninhydrin reaction) were combined, placed in 200 ml of methanol, and the solution was stirred for 30 minutes. When the silica gel was filtered off and methanol concentrated, 92 mg of IIIa-29-1 resulted.

EXAMPLE 66

Two millimols of IIIa-12-1 synthesized by the method of Example 43 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having RF=0.38 (UV absorption observed, purplish red in Ninhydrin reaction) were combined, placed in 200 ml of methanol, and the solution was stirred for 30 minutes. When the silica gel was filtered off and methanol concentrated, 76 mg of IIIa-30-1 was obtained.

EXAMPLE 67

Two millimols of IIIa-13-2 synthesized in Example 40 were placed in a 50-ml glass pressure container, and 10 ml of N,N-dimethylformamide were added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc. Art. 5717, 20 cm×20 cm×2 mm), developed with a solvent system of methanol and chloroform (1:10), portions having Rf=0.52 (UV absorption observed and purplish red in Ninhydrin reaction) were combined, placed in 200 ml of methanol, and the solution was stirred for 30 minutes. When the silica gel was filtered off and methanol concentrated, 85 mg of IIIa-31-2.

EXAMPLE 68

Two millimols of IIIa-14-1 synthesized by the method of Example 4 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, spots of the solution were placed on twenty silica gel plates (TLCPSC-Fertigplatten KIESELGEL 60F-254 of Merck & Co., Inc., Art 5717, 20 cm×20 cm×2 mm), developed with a solvent system of methanol and chloroform (1:30), portions having Rf=0.60 (UV absorption observed, purplish red in Ninhydrin reaction) were combined, placed in 200 ml of methanol, and the solution was stirred for 30 minutes. When the silica gel was filtered off and methanol concentrated, 98 mg of IIIa-32-1 was obtained.

EXAMPLE 69

Two millimols of IIIa-15-1 synthesized by the method of Example 39 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:30), portions having Rf=0.50 (UV absorption observed, purplish red in Ninhydrin reaction) were combined, placed in 200 ml of methanol, and the solution was stirred for 30 minutes. When the silica gel was filtered off and methanol concentrated, 95 mg of IIIa-33-1 resulted.

EXAMPLE 70

Two millimols of IIIa-16-1 synthesized by the method of Example 45 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.40 (UV absorption observed, purplish red in Ninhydrin reaction) were combined, placed in 200 ml of methanol, and the solution was stirred for 30 minutes. When the silica gel was filtered off and methanol concentrated, 70 mg of IIIa-34-1 was obtained.

EXAMPLE 71

Two millimols of IIIa-17-1 synthesized by the method of Example 42 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:20), portions having Rf=0.40 (UV absorption observed, purplish red in Ninhydrin reaction) were combined, placed in 200 ml of methanol, and the solution was stirred for 30 minutes. By filtering the silica gel off and concentrating methanol, 90 mg of IIIa-35-1 were obtained.

EXAMPLE 72

Thoroughly dried AI-77-B (4.95 m mol or 2.1 g) was dissolved in 25 ml of pyridine, and after adding 6 m mols of oleic anhydride at room temperature, the solution was stirred for 4 hours at room temperature. After distilling pyridine off in vacuum, 100 ml of water was added to the solution. The resulting precipitate was filtered off and dried thoroughly. The dry product was washed three times with a total of 450 ml of hexane (150 ml each) and dried thoroughly. The dry product was then dissolved in 150 ml of chloroform, and after adding 330 mg of p-toluenesulfonic acid, the solution was stirred for 2 hours. To the solution, 100 ml of water was added to form layers. The chloroform layer was separated and dried with sodium sulfate. When the sodium sulfate was filtered off and chloroform layer concentrated, 2.10 g of the compound IIIa-1-13 was obtained.

EXAMPLE 73

Thoroughly dried AI-77-B (7.1 m mols or 3 g) was dissolved in 50 ml of pyridine, and after adding 14 m mols of benzoic anhydride at room temperature, the solution was stirred for 3 hours at room temperature. Pyridine was distilled off in vacuum, and the residue was dried thoroughly. The dry product was dissolved in 40 ml of methanol, and methanol saturated with hydrochloric acid was added to the solution to obtain a pH of 1. The acidic solution was concentrated to dryness under vacuum. The dry product was dissolved in 20 ml of methanol, and 1 N aqueous sodium hydroxide was added to the solution to obtain a pH of 5. The solution was left standing overnight at $-20°$ C., and the resulting precipitate was filtered off. The precipitate was suspended in a water-methanol solvent system (50% water and 50% methanol), and the suspension was passed through a column packed with 300 ml of Amberlite XAD-2. After washing with 1.5 liters of water, the column was eluted with a solvent system of 85% methanol and 15% water. Active fractions were combined, concentrated and dried to give 2.51 g of the compound IIIa-1-14.

EXAMPLE 74

Two millimols of thoroughly dried AI-77-B were suspended in 10 ml of chloroform. Following addition of 10 m mols of 4-cyclohexylbutyric acid and 8 m mols of dicyclohexyl carbodiimide, the solution was stirred for 4 hours at room temperature. After distilling the solvent off in vacuum, the residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.65 (UV absorption observed) were combined, placed in 200 ml of methanol, and the solution was stirred for 30 minutes. When the silica gel was filtered off and methanol concentrated, 730 mg of IIIa-1-19 resulted.

EXAMPLE 75

Two millimols of thoroughly dried AI-77-B were suspended in 10 ml of chloroform. Following the addition of 10 m mole of N-methyltetrazole carboxylic acid and 8 m mols of dicyclohexyl carbodiimide, the solution was stirred for 4 hours at room temperature. After distilling the solvent off in vacuum, the residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.51 (UV absorption observed) were combined, placed in 200 ml of methanol, and the solution was stirred for 30 minutes. When the silica gel was filtered off and methanol concentrated, 520 mg of IIIa-1-27 was obtained.

EXAMPLE 76

The compound IIIa-22-5 synthesized in Example 26 was subjected to the opening of gamma-lactone ring by the method of Example 60. One millimol of the resulting compound IIIb-22-5 was suspended in 10 ml of methylene chloride which was just distilled, and 3 m mols of triethyloxonium fluoroborate was added to the suspension. Upon stirring for one hour at room temperature, the suspension became transparent. Following overnight stirring, the solvent (methylene chloride) was distilled off in vacuum. The residue was dissolved in 10 ml of ethanol, and under cooling with ice, 2 ml of ethanol saturated with ammonia was added to the solution. After a 2-hour stirring, the temperature of the solution was returned to room temperature at which the reaction was continued for 3 days. The residue was dissolved in water, and the solution was passed through a column packed with 50 ml of Amberlite XAD-2. After washing with 100 ml of water, the column was eluted with a solvent system of 15% methanol and 85% water. Active fractions were combined and concentrated to give 310 mg of Vb-14-1.

EXAMPLE 77

The compound IIIa-18-1 synthesized in Example 34 was subjected to the opening of gamma-lactone ring by the method of Example 60. One millimol of the resulting compound IIIb-18-1 was suspended in 10 ml of methylene chloride which was just distilled, and 3 m mole of triethyloxonium fluoroborate was added to the suspension. Upon stirring for one hour at room temperature, the suspension became transparent. Following overnight stirring, the solvent (methylene chloride) was distilled off in vacuum. The residue was dissolved in 10 ml of ethanol, and under cooling with ice, 2 ml of ethanol saturated with ammonia was added to the solution. After a 2-hour stirring, the temperature of the solution was restored to room temperature at which the reaction was continued for 3 days. The residue was dissolved in water, and the solution was passed through a column packed with 50 ml of Amberlite XAD-2. After washing with 100 ml of water, the column was eluted with a solvent system of 15% methanol and 85% water. Active fractions were combined and concentrated to give 310 mg of Vb-10-1.

EXAMPLE 78

The compound IIIa-27-1 synthesized in Example 50 was subjected to the opening of gamma-lactone ring by the method of Example 60. One millimol of the resulting compound IIIb-27-1 was suspended in 10 ml of methylene chloride which was just distilled, and 3 m mole of triethyloxonium fluoroborate was added to the suspension. Upon stirring for one hour at room temperature, the suspension became transparent. Following overnight stirring, the solvent (methylene chloride) was distilled off in vacuum. The residue was dissolved in 10 ml of ethanol, and under cooling with ice, 2 ml of ethanol saturated with ammonia was added to the solution. After a 2-hour stirring, the temperature of the solution was returned to room temperature at which the reaction was continued for 3 days. The residue was dissolved in water, and the solution was passed through a column packed with 50 ml of Amberlite XAD-2. After washing with 100 ml of water, the column was eluted with a solvent system of 10% methanol and 90% water. Active fractions were combined and concentrated to give 290 mg of Vb-19-1.

EXAMPLE 79

The compound IIIa-13-2 synthesized in Example 40 was subjected to the opening of gamma-lactone ring by the method of Example 60. One millimol of the resulting compound IIIb-13-2 was suspended in 10 ml of methylene chloride which was just distilled, and 3 m mols of triethyloxonium fluoroborate was added to the suspension. Upon stirring for one hour at room temperature, the suspension became transparent. Following overnight stirring, the solvent (methylene chloride) was distilled off in vacuum. The residue was dissolved in 10 ml of ethanol, and under cooling with ice, 2 ml of ethanol saturated with ammonia was added to the solution. After a 2-hour stirring, the temperature of the solution was returned to room temperature at which the reaction was continued for 3 days. The residue was dissolved in water, and the solution was passed through a column packed with 50 ml of Amberlite XAD-2. After washing with 100 ml of water, the column was eluted with a solvent system of 15% methanol and 85% water. Active fractions were combined and concentrated to give 290 mg of Vb-5-1.

EXAMPLE 80

The compound IIIa-31-2 synthesized in Example 67 was subjected to the opening of gamma-lactone ring by the method of Example 60. One millimol of the resulting compound IIIb-31-2 was suspended in 10 ml of methylene chloride which was just distilled, and 3 m mols of triethyloxonium fluoroborate was added to the suspension. Upon stirring for one hour at room temperature, the suspension became transparent. Following overnight stirring, the solvent (methylene chloride) was distilled off in vacuum. The residue was dissolved in 10 ml of ethanol, and under cooling with ice, 2 ml of ethanol saturated with ammonia was added to the solution. After a 2-hour stirring, the temperature of the solution was returned to room temperature at which the reaction was continued for 3 days. The residue was dissolved in water, and the solution was passed through a column packed with 50 ml of Amberlite XAD-2. After washing with 100 ml of water, the column was eluted with a solvent system of 20% methanol and 80% water. Active fractions were combined and concentrated to give 310 mg of Vb-23-1.

EXAMPLE 81

Two millimols of thoroughly dried AI-77-B was suspended in 10 ml of chloroform, and after addition of 10 m mols of cyclohexanone-2-carboxylic acid and 8 m mols of dicyclohexyl carbodiimide, the suspension was stirred for 4 hours at room temperature. After distilling the solvent off in vacuum, the residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.70 (UV absorption observed) were combined, placed in 200 ml of methanol, and the solution was stirred for 30 minutes. When the silica gel was filtered off and methanol concentrated, 510 mg of IIIa-1-33 resulted.

EXAMPLE 82

Two millimols of thoroughly dried AI-77-B were suspended in 10 ml of chloroform, and after adding 10 m mols of 4-methylthiobenzoic acid and 8 m mols of dicyclohexyl carbodiimide, the suspension was stirred for 4 hours at room temperature. After distilling the solvent off in vacuum, the residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:30), portions having Rf=0.40 (UV absorption observed) were combined, placed in 200 ml of methanol, and the solution was stirred for 30 minutes. Then the silica gel was filtered off and methanol concentrated, 700 mg of IIIa-1-46 was produced.

EXAMPLE 83

One millimol of IIIa-1-13 synthesized in Example 72 was dissolved in 10 ml of methylene chloride which was just distilled. After adding 1.5 m mols of triethyloxonium fluoroborate in an argon atmosphere, the solution was stirred for 4 hours at room temperature. After distilling methylene chloride in vacuum, 10 ml of dried ethanol was added, and 2 m mols of sodium borohydride was added under cooling with ice. The mixture was stirred for 10 minutes, and thereafter, excess sodium borohydride was decomposed with ethanol saturated with hydrogen chloride gas. After the reaction mixture was evaporated to dryness in vacuum, the dry product was suspended in a water-tetrahydrofuran solvent (40% water, 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 50% tetrahydrofuran were combined and concentrated to give 210 mg of IIIa-18-13.

EXAMPLE 84

One millimol of IIIa-1-14 synthesized in Example 73 was dissolved in 10 ml of methylene chloride which was just distilled. To the solution, 1.5 m mols of triethyloxonium fluoroborate was added in an argon atmosphere, and the solution was stirred for 4 hours at room temperature. After distilling methylene chloride off in vacuum, 10 ml of dried ethanol was added, and 2 m mols of sodium borohydride was added under cooling with ice. Following a 10-minute stirring, excess sodium borohydride was decomposed with ethanol saturated with hydrogen chloride gas. After the reaction mixture was evaporated to dryness in vacuum, the dry product was suspended in a water-tetrahydrofuran solvent (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13.

Fractions were eluted with a concentration of 40% tetrahydrofuran to give 250 mg of IIIa-18-14.

EXAMPLE 85

One millimol of IIIa-1-19 synthesized in Example 74 was dissolved in 10 ml of methylene chloride which was just distilled. To the solution, 1.5 m mols of triethyloxonium fluoroborate was added in an argon atmosphere, and the solution was stirred for 4 hours at room temperature. After distilling methylene chloride off in vacuum, 10 ml of dried ethanol was added, and 2 m mols of sodium borohydride was added under cooling with ice. Following a 10-minute stirring, excess sodium borohydride was decomposed with ethanol saturated with hydrogen chloride. After the reaction mixture was evaporated to dryness in vacuum, the dry product was suspended in a water-tetrahydrofuran solvent (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 60% tetrahydrofuran were combined and concentrated to give 170 mg of IIIa-18-19.

EXAMPLE 86

One millimol of IIIa-1-59 synthesized by the method of Example 74 was dissolved in 10 ml of methylene chloride which was just distilled. To the solution, 1.5 m mols of triethyloxonium fluoroborate was added in an argon atmosphere, and the solution was stirred for 4 hours at room temperature. After methylene chloride was distilled off under vacuum, the residue was dissolved in 10 ml of dried ethanol, and under cooling with ice, 2 m mols of sodium borohydride was added to the solution, which was then stirred for 10 minutes. Excess sodium borohydride was decomposed with ethanol saturated with hydrogen chloride gas and the reaction mixture was evaporated to dryness under vacuum. The dry product was suspended in a water tetrahydrofuran solvent (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 40% tetrahydrofuran were combined and concentrated to give 190 mg of IIIa-18-53.

EXAMPLE 87

One millimol of IIIa-1-16 synthesized by the method of Example 72 was dissolved in 10 ml of methylene chloride which was just distilled. To the solution, 1.5 m mols of triethyloxonium fluoroborate was added in an argon atmosphere, and the solution was stirred at room temperature for 4 hours. After distilling methylene chloride off in vacuum, the residue was dissolved in 10 ml of dried ethanol, and under cooling with ice, 2 m mols of sodium borohydride was added to the solution, which was then stirred for 10 minutes. Excess sodium borohydride was decomposed with ethanol saturated with hydrogen chloride gas, and the reaction mixture was evaporated to dryness in vacuum. The dry product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 60% tetrahydrofuran were combined and concentrated to give 210 mg of IIIa-18-16.

EXAMPLE 88

One millimol of IIIa-1-38 synthesized by the method of Example 73 was dissolved in 10 ml of methylene chloride which was just distilled. To the solution, 1.5 m mols of triethyloxonium fluoroborate was added in an argon atmosphere, and the solution was stirred for 4 hours at room temperature. After distilling methylene chloride off in vacuum, the residue was dissolved in 10 ml of dried ethanol, and under cooling with ice, 2 m mols of sodium borohydride was added to the solution which was then stirred for 10 minutes. Excess sodium borohydride was decomposed with ethanol saturated with hydrogen chloride gas, and the reaction mixture was evaporated to dryness in vacuum. The dry product was suspended in a water-tetrahydrofuran solvent (40% water and 60% tetrahydrofuran) and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 40% tetrahydrofuran were combined and concentrated to give 260 mg of IIIa-18-32.

EXAMPLE 89

One millimol of IIIa-5-14 synthesized by the method of Example 21 was dissolved in 10 ml of methylene chloride which was just distilled. To the solution, 1.5 m mols of triethyloxonium fluoroborate was added, and the solution was stirred for 4 hours at room temperature. After distilling methylene chloride off in vacuum, the residue was dissolved in 10 ml of dried ethanol, and under cooling with ice, 2 m mols of sodium borohydride was added to the solution, which was then stirred for 10 minutes. Excess sodium borohydride was decomposed with ethanol saturated with hydrogen chloride gas, and the reaction mixture was evaporated to dryness under vacuum. The dry product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 60% tetrahydrofuran were combined and concentrated to give 220 mg of IIIa-22-14.

EXAMPLE 90

One millimol of IIIa-5-16 synthesized by the method of Example 21 was dissolved in 10 ml of methylene chloride which was just distilled. To the solution, 1.5 m mols of triethyloxonium fluoroborate was added in an argon atmosphere, and the solution was stirred for 4 hours at room temperature. After distilling methylene chloride off under vacuum, the residue was dissolved in 10 ml of dried ethanol, and under cooling with ice, 2 m mols of sodium borohydride was added to the solution, which was stirred for 10 minutes. Excess sodium borohydride was decomposed with ethanol saturated with hydrogen chloride gas, and the reaction mixture was evaporated to dryness under vacuum. The dry product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 50% tetrahydrofuran were combined and concentrated to give 240 mg of IIIa-22-15.

EXAMPLE 91

One millimol of IIIa-5-23 synthesized by the method of Example 21 was dissolved in 10 ml of methylene chloride which was just distilled. To the solution, 1.5 m mols of triethyloxonium fluoroborate was added in an argon atmosphere, and the solution was stirred at room temperature for 4 hours. After distilling methylene chloride off in vacuum, the residue was dissolved in 10 ml of dried ethanol, and under cooling with ice, 2 m mols of sodium borohydride was added to the solution, which was then stirred for 10 minutes. Excess sodium borohydride was decomposed with ethanol saturated with hydrogen chloride gas, and the reaction mixture was evaporated to dryness in vacuum. The dry product was suspended in a water-tetrahydrofuran solvent system (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 50% tetrahydrofuran were combined and concentrated to give 200 mg of IIIa-22-22.

EXAMPLE 92

One millimol of IIIa-5-19 synthesized by the method of Example 21 was dissolved in 10 ml of methylene chloride which was just distilled. To the solution, 1.5 m mols of triethyloxonium fluoroborate was added, and the solution was stirred for 4 hours at room temperature. After distilling methylene chloride off in vacuum, the residue was dissolved in 10 ml of dried ethanol, and under cooling with ice, 2 m mols of sodium borohydride was added to the solution, which was then stirred for 10 minutes. Excess sodium borohydride was decomposed with ethanol saturated with hydrogen chloride gas, and the reaction mixture was evaporated to dryness in vacuum. The dry product was suspended in a water-tetrahydrofuran solvent (40% water and 60% tetrahydrofuran), and the suspension was passed through a column packed with 70 ml of Amberlite XAD-2. After washing with 500 ml of water, the column was eluted using a tetrahydrofuran-water solvent system in the same manner as in Example 13. Fractions eluted with a concentration of 70% tetrahydrofuran were combined and concentrated to give 190 mg of IIIa-22-18.

EXAMPLE 93

One millimol of IIIa-5-123 synthesized in Example 22 was suspended in a solvent comprising 2 ml of methanol and 4 ml of water, and 1 N aqueous sodium hydroxide was added to the suspension until the pH reached 12. When the suspension was stirred at room temperature, its pH became lower than 12, so that the same alkali was further added to obtain a pH of 12. When the pH no longer dropped below 12, 1 N hydrochloric acid was used to adjust the pH of the suspension to 7. The so treated suspension was passed through a column packed with 30 ml of Amberlite XAD-2. After washing with 500 ml of water, the column was eluted using a methanol-water solvent system in the same manner as in Example 22. Fractions eluted with a concentration of 80% methanol were combined and concentrated. The concentrate was dissolved in 10 ml of methanol saturated with hydrogen chloride, and the solution was stirred for 30 minutes under cooling with ice. The solvent was distilled off and the residue was dried thoroughly to give 380 mg of IIIa-13-8.

EXAMPLE 94

One millimol of IIIa-5-7 synthesized by the method of Example 22 was suspended in a solvent comprising 2 ml of methanol and 4 ml of water, and 1 N aqueous sodium hydroxide was added to the suspension until the pH reached 12. When the suspension was stirred at room temperature, its pH become lower than 12, so that the same alkali was further added to obtain a pH of 12. When the pH no longer dropped below 12, 1 N hydrochloric acid was used to adjust the pH to 7. The so treated suspension was passed through a column packed with 30 ml of Amberlite XAD-2. After washing with 500 ml of water, the column was eluted using a methanol-water solvent system in the same manner as in Example 22. Fractions eluted with a concentration of 50% methanol were combined and concentrated. The concentrate was dissolved in 10 ml of methanol saturated with hydrogen chloride, and the solution was stirred for 30 minutes under cooling with ice. The solvent was distilled off in vacuum and the residue was dried thoroughly to give 350 mg of IIIa-13-1.

EXAMPLE 95

One millimol of IIIa-5-124 synthesized by the method of Example 22 was suspended in a solvent comprising 2 ml of methanol and 4 ml of water, and 1 N aqueous sodium hydroxide was added until the pH of the suspension reached 12. When the suspension was stirred at room temperature, the pH became lower than 12, so that the same alkali was further added to obtain a pH of 12. When the pH no longer dropped below 12, 1 N hydrochloric acid was used to adjust the pH to 7. The so treated suspension was passed through a column packed with 30 ml of Amberlite XAD-2. After washing with 500 ml of water, the column was eluted using a methanol-water solvent system in the same manner as in Example 22. Fractions eluted with a concentration of 60% methanol were combined and concentrated. The concentrate was dissolved in 10 ml of methanol saturated with hydrogen chloride, and the solution was stirred for 30 minutes under cooling with ice. The solvent was distilled off in vacuum and the residue was dried thoroughly to give 300 mg of IIIa-13-33.

EXAMPLE 96

One millimol of IIIa-5-125 synthesized in Example 22 was suspended in a solvent comprising 2 ml of methanol and 4 ml of water, and 1 N aqueous sodium hydroxide was added to the suspension until its pH reached 12. When the suspension was stirred at room temperature, the pH became lower than 12, so that the same alkali was added to the suspension to obtain a pH of 12. When the pH no longer dropped below 12, 1 N hydrochloric acid was added to adjust the pH to 7. The so treated suspension was passed through a column packed with 30 ml of Amberlite XAD-2. After washing with 500 ml of water, the column was eluted using a methanol-water solvent system in the same manner as in Example 22.

Fractions eluted with a concentration of 60% methanol were combined and concentrated. The concentrate was dissolved in 10 ml of methanol saturated with hydrogen chloride and the solution was stirred for 30 minutes under cooling with ice. The solvent was distilled off under vacuum and the residue was dried thoroughly to give 280 mg of IIIa-13-20.

EXAMPLE 97

Two millimols of IIIa-13-1 synthesized in Example 94 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertiplatten KIESELGEL 60F-254 of Merck & Co., Inc., Art. 5717, 20 cm×20 cm×2 mm), developed with a solvent system of methanol and chloroform (1:15), portions having Rf=0.40 (UV absorption observed, purplish red in Ninhydrin reaction) were combined, placed in 200 ml of methanol, and the solution was stirred for 30 minutes. When the silica gel was filtered off and methanol concentrated, 70 mg of IIIa-31-1 resulted.

EXAMPLE 98

Two millimols of IIIa-13-8 synthesized in Example 93 were placed in a 50-ml glass pressure container, and 10 ml of N,N-dimethylformamide was added to dissolve the compound. After adding 10 m mols of methyl iodide, the container was closed and shaken vigorously for one hour at room temperature. Another 10 m mols of methyl iodide was added, and a reaction was performed in the same manner. Methyl iodide was again added in an amount of 10 m mols, and after vigorous shaking of the container for 24 hours, the solvent (N,N-dimethylformamide) and unreacted methyl iodide were distilled off in vacuum. The residue was dissolved in 2 ml of methanol, and spots of the solution were placed on twenty silica gel plates (TLCPSC-Fertigplatten KIESELGEL 60F-254 of Merck & Co., Inc., Art. 5717, 20 cm×20 cm×2 mm), developed with a solvent system of methanol and chloroform (1:10), portions having Rf=0.52 (UV absorption observed, purplish red in Ninhydrin reaction) were combined, placed in 200 ml of methanol, and the solution was stirred for 30 minutes. When the silica gel was filtered off and methanol concentrated, 82 mg of IIIa-31-13 was obtained.

EXAMPLE 99

Two millimols of thoroughly dried AI-77-A were placed in a pressure container, and after adding 50 m mols of ethylamine, the container was closed and the mixture was stirred for 10 minutes at 100° C. The reaction mixture was dissolved in 2 ml of methanol, and spots of the solution were placed on fifteen silica gel plates (TLCPSC-Fertigplatten KIESELGEL 60F-254 of Merck & Co., Inc., Art. 5717, 20 cm×20 cm×2 mm), developed with a solvent system of chloroform and methanol (7:1), portions having Rf=0.15 (UV absorption observed) were combined, placed in 100 ml of methanol, and the solution was stirred for 20 minutes. When the silica gel was filtered off and methanol concentrated, 200 mg of Vb-1-2 resulted.

EXAMPLE 100

Two millimols of thoroughly dried AI-77-A were placed in a pressure container, and after adding 40 m mols of isopropylamine, the container was closed and the mixture was stirred for 10 minutes at 100° C. The reaction mixture was dissolved in 2 ml of methanol, and spots of the solution were placed on fifteen silica gel plates (TLCPSC-Fertigplatten KIESELGEL 60F-254 of Merck & Co., Inc., Art. 5717, 20 cm×20 cm×2 mm), developed with a solvent system of chloroform and methanol (7:1), portions having Rf=0.30 (UV absorption observed) were combined, placed in 100 ml of methanol, and the solution was stirred for 20 minutes. When the silica gel was filtered off and methanol concentrated, 230 mg of Vb-1-41 resulted.

EXAMPLE 101

Thirty grams of AI-77-B were placed in a glass pressure container, and 150 ml of dimethylformamide was added to dissolve the compound. After adding 300 ml of methyl iodide, the solution was stirred overnight at 50° C. Dimethylformamide and excess methyl iodide were distilled off in vacuum, and the residue was dissolved in a solvent comprising 50 ml of methanol and 50 ml of water. The solution was passed through a column packed with two liters of Amberlite XAD-2. After thorough washing with a solvent comprising 50% methanol and 50% water, the column was eluted with a solvent comprising 80% methanol and 20% water (containing 10% of 1 N hydrochloric acid). When the eluates were concentrated, 20 g of AI-77-F was obtained as a white crystalline precipitate. The precipitate was dried by desiccation using phosphorus pentoxide at 50° C. overnight under vacuum. The dry solid had physicochemical properties that corresponded to the physicochemical data for AI-77-F described herein.

EXAMPLE 102

Ten millimols of thoroughly dried AI-77-B were dissolved in 100 ml of a mixture of 1 N hydrochloric acid and ethanol on an ice bath. Immediately thereafter, the solvent was removed in vacuum (bath temperature: 20°-30° C.), and then, a vacuum pump was used to dry the residue thoroughly. The dry residue was dissolved in 50 ml of a solution containing 0.5 mols of sodium bicarbonate, and it was extracted with 600 ml of ethyl acetate. After washing the ethylacetate layer with saturated aqueous sodium chloride, sodium sulfate was added to the layer which was left to stand overnight. When sodium sulfate was filtered off and ethyl acetate removed in vacuum, 3.98 g of AI-77-B-gamma-lactone (AI-77-Ba) was obtained (yield: 98%).

EXAMPLE 103

Five millimols of AI-77-Ba were dissolved in 100 ml of dried methanol, and up to 50 m mols of dried ammonia gas was bubbled through the solution on a water bath (10°-15° C.). The reaction system was closed and stirred for a period of 2 hours. The solvent was removed in vacuum, and the residue was dissolved in 50 ml of methanol. Five grams of "Hyflo-super-cel" were added to the solution, and after its stirring, the solvent was removed in vacuum, followed by the drying of the residue. The residue was divided into fine particles in a mortar, and the particles were placed on a silica gel column (200 g) filled with chloroform. First, the column was washed with 500 ml of chloroform, and then it was eluted with 500 ml of a solvent system of chloroform and methanol (3:1). Fractions 51 through 150 were combined and concentrated to dryness. A small amount of methanol was added to the residue and the mixture was left standing until a white precipitate was formed. The precipitate was washed with ethyl acetate and the solvent distilled off under vacuum to give 0.51 g of the end compound VII-1-1.

EXAMPLE 104

Five millimols of AI-77-Ba were dissolved in 100 ml of dried methanol. Dried nitrogen gas was bubbled through 70 ml of monomethylamine (40% aqueous solution), and the displaced monomethylamine was captured in a trap cooled with Dry Ice. The trapped monomethylamine was vaporized on a water bath (10°–20° C.), dried through a tube filled with caustic soda, and bubbled through the previously prepared solution of AI-77-Ba in methanol. Reaction was performed on a water bath (10°–15° C.) for 3 hours, and the reaction mixture was evaporated to dryness in vacuum. The residue was dissolved in 20 ml of chloroform and placed on a silica gel column (100 g) filled with chloroform. After washing with 500 ml of chloroform, the column was eluted with 2 liters of a solvent system of chloroform and methanol (4:1). Upon evaporating the active fractions to dryness under vacuum, 1.3 g of the end compound VII-1-2 was obtained.

EXAMPLE 105

Five millimols of AI-77-Ba were dissolved in 100 ml of dried methanol, and after adding 50 m mole of n-butylamine, the reaction system was closed and stirred for 5 hours on a water bath (10°–15° C.). After the reaction, the solvent and excess n-butylamine were evaporated and concentrated to dryness in vacuum. The resulting residue was dissolved in 10 ml of chloroform, and the solution was placed on a silica gel column (100 g) filled with chloroform. After washing with 200 ml of chloroform, the column was eluted with 2.5 liters of a solvent system of chloroform and methanol (7:1). When active fractions were concentrated to dryness in vacuum, 1.2 g of the end compound VII-1-4 were obtained.

EXAMPLE 106

Five millimols of AI-77-Ba were dissolved in 100 ml of dried methanol, and after adding 50 m mols of octadecylamine, the reaction system was closed and stirred for 20 hours at room temperature. After the reaction, the solvent was removed under vacuum. The resulting residue was dissolved in 50 ml of chloroform, and the solution was placed on a silica gel column (300 g) filled with chloroform. The column was eluted with 4 liters of a chloroform-methanol solvent system (50:1). By concentrating the active fractions to dryness, 0.45 g of the end compound VII-1-6 were obtained.

EXAMPLE 107

Five millimols of AI-77-Ba were dissolved in 100 ml of dried methanol, and after adding 50 m mols of tetrahydrofurfurylamine, the reaction system was closed and stirred for 15 hours at room temperature. After the solvent was removed in vacuum, a high-vacuum pump was used to remove tetrahydrofurfurylamine. The resulting residue was dissolved in chloroform, and the solution was placed on a silica gel column (100 g) filled with chloroform. After washing with 200 ml of chloroform, the column was eluted with 2 liters of a chloroform-methanol solvent (9:1). Upon concentrating the eluates to dryness, 0.63 g of the end compound VII-1-15 was obtained.

EXAMPLE 108

Five millimols of AI-77-BA were dissolved in 100 ml of dried ethanol, and after adding 50 millimols of oleylamine, the reaction system was closed and stirred for 20 hours at room temperature. After the reaction, the solvent was removed in vacuum. The resulting residue was dissolved in 50 ml of chloroform, and the solution was placed on a silica gel column (300 g) filted with chloroform. The column was eluted with 5 liters of a chloroform-methanol solvent system (50:1), and the eluates were concentrated to dryness to give 0.38 g of the end compound VII-1-8.

EXAMPLE 109

Five millimols of AI-77-Ba were dissolved in 100 ml of dried methanol, and after adding 50 m mols of benzylamine, the reaction system was closed and stirred for 10 hours at room temperature. After the reaction, the solvent was removed in vacuum, and a high-vacuum pump was used to remove benzylamine. The resulting residue was dissolved in chloroform, and the solution was placed on a silica gel column (100 g) filled with chloroform. After washing with 200 ml of chloroform, the column was eluted with 2 liters of a chloroform-methanol solvent system (15:1). Upon concentrating the eluates to dryness, 0.71 g of the compound VII-1-10 was obtained.

EXAMPLE 110

Five millimols of AI-77-Ba were dissolved in 100 ml of dried methanol, and after adding 50 m mols of furylamine, the reaction system was closed and stirred for 16 hours at room temperature. After the reaction, the solvent was removed in vacuum, and a high-vacuum pump was used to remove furylamine. The resulting residue was dissolved in chloroform, and the solution was placed on a silica gel column (100 g) filled with chloroform. After washing with 200 ml of chloroform, the column was eluted with 2 liters of a chloroform-methanol solvent system (12:1), and upon concentrating the eluates to dryness, 0.55 g of the compound VII-1-14 was obtained.

EXAMPLE 111

Five millimols of AI-77-Ba were dissolved in 100 ml of dried methanol, and after adding 50 m mols of 2-aminoethyltetrahydropyran, the reaction system was closed and stirred for 13 hours at room temperature. After the reaction, the solvent was removed in vacuum, and a high-vacuum pump was used to remove 2-aminoethyl tetrahydropyran. The resulting residue was dissolved in chloroform, and the solution was placed on a silica gel column (100 g) filled with chloroform. After washing with 200 ml of chloroform, the column was eluted with a solvent system comprising a mixture of chloroform and methanol (9:1). Upon concentrating the eluates to dryness, 0.67 g of the compound VII-1-16 was obtained.

EXAMPLE 112

Five millimols of AI-77-Ba were dissolved in 100 ml of dried ethanol, and after adding 50 m mols of 2-naphthalenemethylamine, the reaction system was closed and stirred for 48 hours at room temperature. After the reaction, the solvent was removed under vacuum. The resulting residue was dissolved in 50 ml of chloroform, and the solution was placed on a silica gel column (300 g) filled with chloroform. The column was eluted with 7 liters of a solvent system comprising a mixture of chloroform and methanol (60:1). Concentrating the eluates to dryness gave 1.08 g of the compound VII-1-18.

EXAMPLE 113

Five millimols of AI-77-Ba were dissolved in 100 ml of dried methanol, and after adding 50 m mols of 3-methoxybutylamine, the reaction system was closed and stirred for 12 hours at room temperature. After the reaction, the solvent was removed under vacuum, and a high-vacuum pump was used to remove 3-methoxybutylamine. The resulting residue was dissolved in chloroform, and the solution was placed on a silica gel column (100 g) filled with chloroform. After washing with 200 ml of chloroform, the column was eluted with 2 liters of a solvent system comprising a mixture of chloroform and methanol (8:1). Upon concentrating the eluates to dryness, 1.14 g of the compound VII-1-26 was obtained.

EXAMPLE 114

Five millimols of AI-77-Ba were dissolved in 100 ml of dried methanol, and after adding 50 m mols of geranylamine, the reaction system was closed and stirred for 20 hours at room temperature. After the reaction, the solvent was removed under vacuum, and a high-vacuum pump was used to remove geranylamine. The resulting residue was dissolved in chloroform, and the solution was placed on a silica gel column (100 g) filled with chloroform. After washing with 200 ml of chloroform, the column was eluted with 2 liters of a solvent system of chloroform and methanol (30:1). Upon concentrating the eluates to dryness, 0.58 g of the compound VII-1-30 was obtained.

EXAMPLE 115

Five millimols of AI-77-Ba were dissolved in 100 ml of dried methanol, and after adding 50 m mols of p-toluidine, the reaction system was closed and stirred for 48 hours at room temperature. After the reaction, the solvent was removed in vacuum. The resulting dry residue was dissolved in 50 ml of chloroform, and the solution was placed on a silica gel column (300 g) filled with chloroform. The column was eluted with 5 liters of a solvent system of chloroform and methanol (20:1). When the eluates were concentrated to dryness, 1.03 g of the end compound VII-1-43 was obtained.

EXAMPLE 116

Five millimols of AI-77-Ba were dissolved in 100 ml of dried methanol, and after adding 50 m mols of N-(2-aminoethyl)-piperidine, the reaction system was closed and stirred for 15 hours at room temperature. After the reaction, the solvent was removed under vacuum, and a high-vacuum pump was used to remove N-(2-aminoethyl)-piperidine. The resulting residue was dissolved in chloroform, and the solution was placed on a silica gel column (100 g) filled with chloroform. After washing with 200 ml of chloroform, the column was eluted with 2 liters of a solvent system of chloroform and methanol (12:1). When the eluates were concentrated to dryness, 0.53 g of the compound VII-1-46 resulted.

EXAMPLE 117

Five millimols of IIIa-10-1 synthesized in Example 47 were dissolved in 50 ml of dried dimethylformamide, and up to 6.5 m mols of dried ammonia gas was bubbled through the solution on a water path (10°–15° C.). The reaction system was closed and the reaction was carried out for a period of 48 hours. Immediately after the reaction, the solvent was removed under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (10:1). When the eluates were concentrated to dryness in vacuum, 0.19 g of the compound VII-2-1 resulted.

EXAMPLE 118

Five millimols of IIIa-11-6 synthesized in Example 48 were dissolved in 30 ml of dried dimethylformamide, and up to 7.0 m mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (15:1). By concentrating the eluates to dryness under vacuum, 0.27 g of the compound VII-3-2 were obtained.

EXAMPLE 119

Five millimols of IIIa-12-1 synthesized in Example 43 were dissolved in 30 ml of dried dimethylformamide, and up to 7.0 m mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (10:1). When the eluates were concentrated to dryness in vacuum, 0.26 g of the compound VII-4-1 was formed.

EXAMPLE 120

Five millimols of IIIa-13-2 obtained in Example 40 were dissolved in 30 ml of dried methanol, and after adding 50 m mols of butylamine, the reaction system was closed and stirred for 5 hours on a water bath (10°–15° C.). After the reaction, the solvent and butylamine were removed in vacuum. The resulting residue was dissolved in 10 ml of chloroform, and the solution was placed on a silica gel column (100 g) filled with chloroform. After washing with 150 ml of chloroform, the column was eluted with 2 liters to a solvent system of chloroform and methanol (30:1). By concentrating the eluates to dryness, 1.41 g of the compound VII-5-3 was formed.

EXAMPLE 121

To 5 m mols of IIIa-13-2 (hydrochloride) prepared in Example 40, 100 ml of 0.5 M aqueous sodium bicarbonate was added, and the mixture was extracted with 300 ml of ethyl acetate in three steps. After washing the ethyl acetate layer with saturated aqueous sodium chloride, the layer was dried with sodium sulfate. By filtering sodium sulfate off and removing ethyl acetate in vacuum, 2.3 g of IIIa-13-2 (free of hydrochloric acid) was formed. The residue was dissolved in 100 ml of dried methanol, and after adding 50 m mols of p-toluidine, the reaction system was closed and stirred for 3 days at room temperature. After the reaction, the solvent was removed under vacuum, and the residue was dissolved in 50 ml of chloroform, and the solution was placed on a silica gel column (400 g) filled with chloroform. The column was eluted with 5 liters of a solvent system of chloroform and methanol (30:1). By concentrating the eluates to dryness under vacuum, 1.4 g of the compound VII-5-4 was obtained.

EXAMPLE 122

Five millimols of IIIa-14-9 synthesized in Example 41 were dissolved in 30 ml of dried dimethylformamide, and up to 6 m mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (30:1). By concentrating the eluates to dryness under vacuum, 0.31 g of the compound VII-6-3 was obtained.

EXAMPLE 123

Five millimols of IIIa-15-8 prepared in Example 39 were dissolved in 100 ml of dried methanol, and after adding 50 m mols of butylamine, the reaction system was closed and stirred for 5 hours on a water bath (10°–16° C.). After the reaction, the solvent and butylamine were removed under vacuum. The resulting residue was dissolved in 10 ml of chloroform, and the solution was placed on a silica gel column (100 g) filled with chloroform. After washing with 150 ml of chloroform, the column was eluted with 3 liters of a solvent system of chloroform and methanol (25:1). By concentrating the eluates to dryness, 1.58 g of the compound VII-7-4 was formed.

EXAMPLE 124

Five millimols of IIIa-16-1 synthesized in Example 33 were dissolved in 100 ml of dried methanol, and up to 30 m mols of dried ammonia gas was bubbled through the solution on a water bath (10°–15° C.). The reaction system was closed and the reaction was carried out for a period of 2 hours. Immediately after the reaction, the solvent was removed under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (10:1). By concentrating the eluates to dryness under vacuum, 1.11 g of the compound VII-8-1 was obtained.

EXAMPLE 125

Five millimols of IIIa-18-2 synthesized in Example 35 were dissolved in 100 ml of dried methanol, and up to 50 m mols of dried ammonia gas was bubbled through the solution on a water bath (10°–15° C.). The reaction system was closed and the reaction was carried out for a period of 2 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (15:1). By concentrating the eluates to dryness under vacuum, 1.18 g of the compound VII-10-1 was obtained.

EXAMPLE 126

Five millimols of IIIa-18-6 synthesized in Example 36 were dissolved in 100 ml of dried ethanol, and up to 50 m mols of dried ammonia gas was bubbled through the solution on a water bath (10°–15° C.). The reaction system was closed and the reaction was carried out for a period of 3 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). By concentrating the eluates to dryness under vacuum, 1.21 g of the compound VII-10-2 was obtained.

EXAMPLE 127

Five millimols of IIIa-18-6 prepared in Example 36 were dissolved in 100 ml of dried methanol, and after adding 50 m mol of butylamine, the reaction system was closed and stirred for 3 hours on a water bath (10°–16° C.). After the reaction, the solvent and butylamine were removed in vacuum. The resulting residue was dissolved in 10 ml of chloroform, and the solution was placed on a silica gel column (100 g) filled with chloroform. After washing with 150 ml of chloroform, the column was eluted with 3 liters of a solvent system of chloroform and methanol (30:1). By concentrating the eluates to dryness, 1.39 g of the compound VII-10-4 was obtained.

EXAMPLE 128

Five millimols of IIIa-20-2 synthesized in Example 17 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (30:1). By concentrating the eluates to dryness under vacuum, 0.29 g of the compound VII-12-1 was obtained.

EXAMPLE 129

Five millimols of IIIa-21-9 synthesized in Example 63 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform and the solution was placed on a silica gel column (100 g) filled with chloroform. After washing with 300 ml of chloroform, the column was eluted with 2 liters of a solvent system of chloroform and methanol (15:1). Then the eluates were concentrated to dryness under vacuum, 0.18 g of the compound VII-13-3 resulted.

EXAMPLE 130

Five millimols of IIIa-22-5 synthesized in Example 26 were dissolved in 100 ml of dried methanol, and up to 50 m mols of dried ammonia gas was bubbled through the solution on a water bath (10°–15° C.). The reaction system was closed and the reaction was carried out for a period of 3 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (15:1). By concentrating the eluates to dryness under vacuum, 1.36 g of the compound VII-14-2 was obtained.

EXAMPLE 131

Five millimols of IIIa-22-15 synthesized in Example 90 were dissolved in 100 ml of dried methanol, and up to 50 m mols of dried ammonia gas was bubbled through the solution on a water bath (10°–15° C.). The reaction system was closed and the reaction was carried out for a period of 3 hours. Immediately after the reaction, the solvent was removed under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). By concentrating the eluates to dryness under vacuum, 1.38 g of the end compound VII-14-5 was obtained.

EXAMPLE 132

Five millimols of IIIa-23-11 prepared in Example 19 were dissolved in 30 ml of dried dimethylformamide. Dried nitrogen gas was bubbled through 30 ml of monoethylamine (70% aqueous solution), and the displaced monoethylamine was captured in a trap cooled with Dry Ice. The trapped monoethylamine was vaporized on a lukewarm water bath (20°–30° C.), dried through a tube filled with caustic soda, and up to 7 m mols of such monoethylamine was bubbled through the previously prepared solution of IIIa-23-11 in dimethylformamide. The reaction system was closed and stirred for 48 hours. After the reaction, the solvent was distilled off in vacuum. The resulting residue was dissolved in 30 ml of chloroform, and the solution was placed on a silica gel column (100 g) filled with chloroform. The column was eluted with 3 liters of a solvent system of chloroform and methanol (20:1). By concentrating the eluates to dryness, 0.35 g of the compound VII-15-4 was obtained.

EXAMPLE 133

Five millimols of IIIa-24-16 prepared in Example 25 were dissolved in 100 ml of dried methanol. Dried nitrogen gas was bubbled through 30 ml of monoethylamine (70% aqueous solution), and the displaced monoethylamine was captured in a trap cooled with Dry Ice. The trapped monoethylamine was vaporized on a lukewarm waterbath (20°–30° C.), dried through a tube filled with caustic soda, and up to 50 m mols of such monoethylamine was bubbled through the previously prepared solution of IIIa-24-16 in methanol. The reaction system was closed and stirred for 3 hours. Thereafter, the solvent was removed under vacuum, and the resulting residue was dissolved in 30 ml of chloroform, and the solution was placed on a silica gel column (100 g) filled with chloroform. The column was eluted with 3 liters of a solvent system of chloroform and methanol (30:1). By concentrating the eluates to dryness, 1.51 g of the compound VII-16-4 was obtained.

EXAMPLE 134

Five millimols of IIIa-25-9 synthesized in Example 31 were dissolved in 100 ml of dried methanol, and up to 50 m mols of dried ammonia gas was bubbled through the solution on a water bath (10°–20° C.). The reaction system was closed and the reaction was carried out for a period of 2 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (15:1). By concentrating the eluates to dryness under vacuum, 1.25 g of the end compound VII-17-3 was obtained.

EXAMPLE 135

Five millimols of IIIa-26-9 synthesized in Example 30 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was removed under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). By concentrating the eluates to dryness under vacuum, 0.22 g of the compound VII-18-3 was obtained.

EXAMPLE 136

Five millimols of IIIa-27-1 synthesized in Example 50 were dissolved in 100 ml of dried methanol, and up to 50 m mols of dried ammonia gas was bubbled through the solution on a water bath (10°–15° C.). The reaction system was closed and the reaction was carried out for a period of 2 hours. Immediately after the reaction, the solvent was removed under vacuum. The resulting dry residue was dissolved in 10 ml of chloroform and the solution was placed on a silica gel column (100 g) filled with chloroform. After washing with 300 ml of chloroform, the column was eluted with 2 liters of a solvent system of chloroform and methanol (10:1). By concentrating the eluates to dryness under vacuum, 1.57 g of the compound VII-19-1 was obtained.

EXAMPLE 137

Five millimols of IIIa-28-1 synthesized in Example 64 were dissolved in 30 ml of dried dimethylformamide, and up to 7 m mols of dried ammonia gas was bubbled through the solution on a water bath (10°–15° C.). The reaction system was closed and the reaction was carried out for a period of 40 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (12:1). By concentrating the eluates to dryness under vacuum, 0.19 g of the compound VII-20-1 was obtained.

EXAMPLE 138

Five millimols of IIIa-29-1 synthesized in Example 65 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was distilled off. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (15:1). By concentrating the eluate to dryness under vacuum, 0.23 g of the compound VII-21-1 was obtained.

EXAMPLE 139

Five millimols of IIIa-30-1 synthesized in Example 66 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was removed under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (15:1). By concentrating the eluates to dryness under vacuum, 0.18 g of the compound VII-22-1 was obtained.

EXAMPLE 140

Five millimols of IIIa-31-2 prepared in Example 67 were dissolved in 100 ml of dried methanol, and after adding 50 m mols butylamine, the reaction system was closed and stirred for 3 hours on a water bath (10°–15° C.). After the reaction, the solvent and butylamine were removed under vacuum. The resulting residue was dissolved in 100 ml of chloroform, and the solution was placed on a silica gel column (100 g) filled with chloroform. After washing with 150 ml of chloroform, the column was eluted with 4 liters of a solvent system of chloroform and methanol (20:1). By concentrating the eluates to dryness, 1.48 g of the compound VII-23-2 was obtained.

EXAMPLE 141

Five millimols of IIIa-31-1 synthesized in Example 97 were dissolved in 100 ml of dried methanol, and up to 50 m mols of dried ammonia was bubbled through the solution on a water bath (10°–15° C.). The reaction system was closed and the reaction was carried out for a period of 2 hours. Immediately after the reaction, the solvent was distilled off under vacuum. The resulting dry residue was dissolved in 10 ml of chloroform and the solution was placed on a silica gel column (100 g) filled with chloroform. After washing with 300 ml of chloroform, the column was eluted with 2 liters of a solvent system of chloroform and methanol (10:1). By concentrating the eluates to dryness under vacuum, 1.29 g of the compound VII-23-5 was obtained.

EXAMPLE 142

Five millimols of IIIa-32-1 synthesized in Example 68 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was distilled off in vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (15:1). By concentrating the eluates to dryness under vacuum, 0.30 g of the compound VII-24-1 was obtained.

EXAMPLE 143

Five millimols of IIIa-33-1 synthesized in Example 69 were dissolved in 100 ml of dried methanol, and up to 50 m mols of dried ammonia gas was bubbled through the solution on a water bath (10°–15° C.). The reaction system was closed and the reaction was carried out for a period of 2 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). By concentrating the eluates to dryness under vacuum, 1.27 g of the compound VII-25-1 was obtained.

EXAMPLE 144

Five millimols of IIIa-34-1 synthesized in Example 70 were dissolved in 100 ml of dried methanol, and up to 50 m mols of dried ammonia gas was bubbled through the solution on a water bath (10°–15° C.). The reaction system was closed and the reaction was carried out for a period of 2 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (9:1). By concentrating the elates to dryness under vacuum, 1.11 g of the compound VII-26-1 was obtained.

EXAMPLE 145

Five millimols of IIIa-35-1 synthesized in Example 71 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was removed under vacuum. The resulting dry residue was dissolved in 10 ml of chloroform, and the solution was placed on a silica gel column (100 g) filled with chloroform. After washing with 300 ml of chloroform, the column was eluted with 2 liters of a solvent system of chloroform and methanol (15:1). By concentrating the eluates to dryness under vacuum, 0.16 g of the compound VII-27-1 was obtained.

EXAMPLE 146

Five millimols of IIIa-1-4 synthesized in Example 11 were dissolved in 30 ml of dried dimethylformamide, and up to 7 m mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (15:1). By concentrating the eluates to dryness under vacuum, 0.34 g of the compound VII-28-2 was obtained.

EXAMPLE 147

Five millimols of IIIa-1-11 prepared in Example 10 were dissolved in 100 ml of dried ethanol. Dried nitrogen gas was bubbled into 30 ml of monoethylamine (70% aqueous solution), and the displaced monoethylamine was captured in a trap cooled with Dry Ice. The trapped monoethylamine was vaporized on a lukewarm water bath (20°–30° C.), dried through a tube filled with caustic soda, and bubbled into the solution of IIIa-1-11 in ethanol. The reaction system was closed and the reaction was carried out with stirring for 3 hours. After the reaction, the solvent was distilled off under vacuum. The resulting residue was dissolved in 30 ml of chloroform, and the solution was placed on a silica gel column (100 g) filled with chloroform. The column was eluted with 3 liters of a solvent system of chloroform and methanol (50:1). By concentrating the eluates to dryness, 0.9 g of the compound VII-28-4 was obtained.

EXAMPLE 148

Five millimols of IIIa-2-10 prepared in Example 13 were dissolved in 30 ml of dried dimethylformamide. Dried nitrogen gas was bubbled into monomethylamine (40% aqueous solution), and the displaced monomethylamine was captured in a trap cooled with Dry Ice. The trapped monomethylamine was vaporized on a lukewarm water bath (20°–30° C.), dried through a tube filled with caustic soda, and up to 7 m mols of the dried monomethylamine was bubbled into the solution of IIIa-2-10 in dimethylformamide. The reaction system was closed and the reaction was carried out with stirring for 48 hours. After the reaction, the solvent was removed under vacuum. The resulting residue was dissolved in 30 ml of chloroform, and the solution was placed on a silica gel column (100 g) filled with chloroform. The column was eluted with 3 liters of a solvent system of chloroform and methanol (20:1). When the eluates were concentrated to dryness, 0.35 g of the compound VII-29-2 resulted.

EXAMPLE 149

Five millimols of IIIa-4-1 synthesized in Example 32 were dissolved in 30 ml of dried dimethylformamide, and up to 7 m mols of dried ammonia gas was bubbled into the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (15:1). By concentrating the eluates to dryness under vacuum, 0.17 g of the compound VII-31-1 was obtained.

EXAMPLE 150

Five millimols of IIIa-5-3 prepared in Example 21 were dissolved in 100 ml of dried methanol. Dried nitrogen gas was bubbled into 30 ml of monoethylamine (70% aqueous solution), and the displaced monoethylamine was captured in a trap cooled with dry Ice. The trapped monoethylamine was vaporized on a lukewarm water bath (20°–30° C.), dried through a tube filled with caustic soda, and bubbled into the solution of IIIa-5-3 in methanol. The reaction system was closed and the reaction was carried out for a period of 3 hours. After the reaction, the solvent was removed under vacuum. The resulting residue was dissolved in 20 ml of chloroform, and the solution was placed on a silica gel column (100 g) filled with chloroform. The column was eluted with 2 liters of a solvent system of chloroform and methanol (8:1). When the eluates were concentrated to dryness, 1.1 g of the compound VII-32-1 resulted.

EXAMPLE 151

Five millimols of IIIa-6-12 synthesized in Example 18 were dissolved in 30 ml of dried dimethylformamide, and up to 7 m mols of dried ammonia gas was bubbled into the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). When the eluates were concentrated to dryness under vacuum, 0.26 of the compound VII-33-1 resulted.

EXAMPLE 152

Five millimols of IIIa-7-16 synthesized in Example 23 were dissolved in 30 ml of dried dimethylformamide, and up to 7 mols of dried ammonia gas was bubbled through the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). By concentrating the eluates to dryness under vacuum, 0.28 g of the compound VII-34-1 was obtained.

EXAMPLE 153

Five millimols of IIIa-8-9 prepared in Example 28 were dissolved in 30 ml of dried dimethylformamide. Dried nitrogen gas was bubbled into 30 ml of monoethylamine (70% aqueous solution), and the displaced monoethylamine was captured in a trap cooled with Dry Ice. The trapped monoethylamine was vaporized on a lukewarm water bath (20°–30° C.), dried through a tube filled with caustic soda, and up to 7 m mols of the dried monoethylamine was bubbled through the solution of IIIa-8-9 in dimethylformamide. The reaction system was closed and the reaction was carried out with stirring for 48 hours. After the reaction, the solvent was removed under vacuum. The resulting residue was dissolved in 30 ml of chloroform, and the solution was placed on a silica gel column (100 g) filled with chloroform. The column was eluted with 3 liters of a solvent system of chloroform and methanol (15:1). By concentrating the eluates to dryness, 0.24 g of the compound VII-35-1 was obtained.

EXAMPLE 154

Five millimols of IIIa-9-9 synthesized in Example 29 were dissolved in 30 ml of dried dimethylformamide, and up to 7 m mols of dried ammonia gas was bubbled into the solution on a water bath (10°–15° C.). The reaction system was closed and the reaction was carried out for a period of 48 hours. Immediately after the reaction, the solvent was distilled off under vacuum. The resulting dry residue was dissolved in 10 ml of chloroform, and the solution was placed on a silica gel column (100 g) filled with chloroform. After washing with 300 ml of chloroform, the column was eluted with 3 liters of a solvent system of chloroform and methanol (20:1). When the eluates were concentrated to dryness under vacuum, 0.33 g of the compound VII-36-1 was obtained.

EXAMPLE 155

Five millimols of thoroughly dried AI-77-F (Example 7) were dissolved in 100 ml of dried dimethylformamide, and after adding 7.5 m mols of benzylamine, the reaction system was closed and stirred for 3 days at room temperature. After the reaction, the solvent and benzylamine were removed under vacuum. The resulting residue was dissolved in 20 ml of chloroform, and the solution was placed on a silica gel column (100 g) filled with chloroform. After washing with 100 ml of chloroform, the column was eluted with 2.5 liters of a solvent system of chloroform and methanol (7:1). By concentrating the eluates to dryness under vacuum, 0.32 g of the compound VII-1-2 was obtained.

EXAMPLE 156

Five millimols of IIIa-3-2 prepared in Example 15 were dissolved in 30 ml of dried dimethylformamide, and after adding 7.5 m mols of benzylamine, the reaction system was closed and stirred for 2 days on a water bath (10°–16° C.). After the reaction, the solvent and benzylamine was removed in vacuum. The resulting residue was dissolved in 10 ml of chloroform, and the solution was placed on a silica gel column (100 g) filled with chloroform. After washing with 150 ml of chloroform, the column was eluted with 2 liters of a solvent system of chloroform and methanol (30:1). By concentrating the eluates to dryness, 0.27 g of the end compound VII-30-1 was obtained.

While the invention has been described in detail and with reference to specific embodiments thereof, it will be apparent to one skilled in the art that various changes and modifications can be made therein without departing from the spirit and scope thereof.

What is claimed is:

1. An AI-77 compound of the formula (I) or (II):

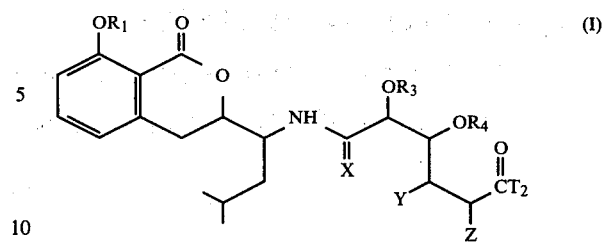

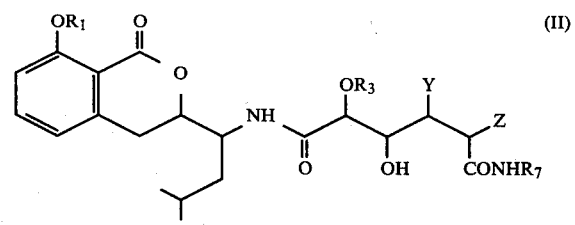

wherein:

X is $NR_6$ or O;

Y is $NHR_5$ or combines with Z to provide a link for bonding C and C;

Z is H or combines with Y to provide a link for bonding C and C;

$R_1$, $R_3$ and $R_5$ are each H, R', $-CH_2R$, or $-COR$;

$R_6$ is H or R;

$R_7$ is H, R or $CH_2R$;

R is a hydrocarbon group consisting of a straight or branched alkyl group of $C_1$ to $C_{17}$ containing from 0 to 3 double bonds or triple bonds, an aromatic group of $C_6$ to $C_{10}$, a bridged hydrocarbon group of $C_7$ to $C_{10}$, a cycloalkyl group of $C_3$ to $C_8$ and an arylaliphatic group having a $C_6$ to $C_{10}$ aromatic group on a $C_1$ to $C_5$ aliphatic group, wherein the above hydrocarbons can be substituted with halogen, oxo, carboxyl, hydroxyl, a straight or branched aliphatic group of $C_1$ to $C_5$ containing from 0 to 3 double bonds or triple bonds, an aromatic group of $C_6$ to $C_{10}$, a cycloalkyl group of $C_3$ to $C_8$, an aromatic-aliphatic group of $C_7$ to $C_{11}$, alkoxy of $C_1$ to $C_5$, thioalkoxyl or $C_1$ to $C_5$, carboalkoxy of $C_2$ to $C_6$, acyl of $C_1$ to $C_6$ or acyloxy of $C_2$ to $C_6$;

R' is the same as R exclusive of those groups wherein unsaturated carbon or tertiary carbon is directly bonded to O or N;

$R_4$ is H or combines with $T_2$ to provide a link for bonding C and O in a lactone ring; and $T_2$ is OH or combines with $R_4$ to provide a link for bonding C and O in a lactone ring;

or a pharmaceutically acceptable salt thereof with hydrohalogenic acid, phosphoric acid, sulfuric acid, oxalic acid, maleic acid or an organic sulfonic acid.

2. A compound of the formula (I) according to claim 1 wherein said compound is represented by the formula

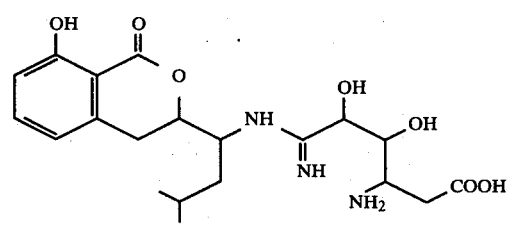

or a pharmaceutically acceptable salt thereof.

3. A compound of the formula (I) according to claim 1 wherein said compound is represented by the formula

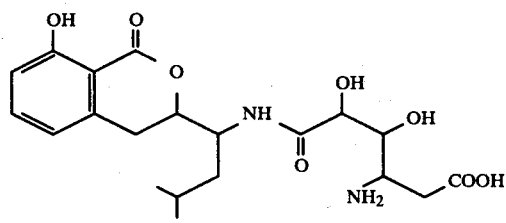

or a pharmaceutically acceptable salt thereof.

4. A compound of the formula (I) according to claim 1 wherein said compound is represented by the formula

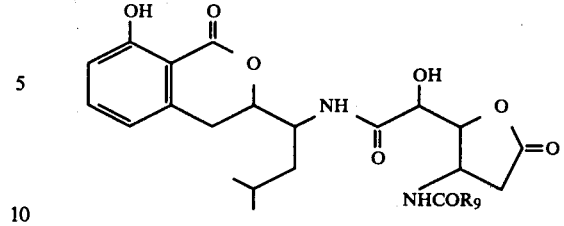

wherein $R_9$ is methyl or ethyl; or a pharmaceutically acceptable salt thereof.

5. A compound of the formula (I) according to claim 1 wherein said compound is represented by the formula

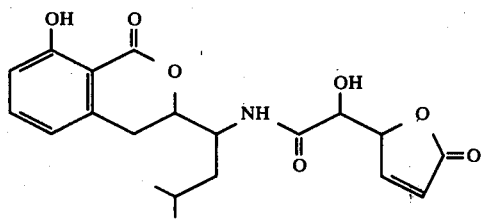

or a pharmaceutically acceptable salt thereof.

* * * * *